(12) United States Patent
Aslan et al.

(10) Patent No.: US 10,874,622 B2
(45) Date of Patent: Dec. 29, 2020

(54) DUAL ASSEMBLY NANOPARTICLES

(71) Applicant: BOARD OF REGENTS, THE UNIVERSITY OF TEXAS SYSTEM, Austin, TX (US)

(72) Inventors: Burcu Aslan, Houston, TX (US); Gabriel Lopez-Berestein, Bellaire, TX (US); Anil K. Sood, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/738,180

(22) PCT Filed: Jun. 23, 2016

(86) PCT No.: PCT/US2016/038970
§ 371 (c)(1),
(2) Date: Dec. 20, 2017

(87) PCT Pub. No.: WO2016/210098
PCT Pub. Date: Dec. 29, 2016

(65) Prior Publication Data
US 2018/0169029 A1     Jun. 21, 2018

Related U.S. Application Data

(60) Provisional application No. 62/184,014, filed on Jun. 24, 2015.

(51) Int. Cl.
| | | |
|---|---|---|
| *A61K 9/51* | (2006.01) | |
| *C12N 15/113* | (2010.01) | |
| *A61P 35/00* | (2006.01) | |
| *A61K 9/00* | (2006.01) | |
| *A61K 31/713* | (2006.01) | |
| *A61K 45/06* | (2006.01) | |
| *A61K 9/50* | (2006.01) | |

(52) U.S. Cl.
CPC .......... *A61K 9/5153* (2013.01); *A61K 9/0024* (2013.01); *A61K 9/5146* (2013.01); *A61K 9/5161* (2013.01); *A61K 31/713* (2013.01); *A61K 45/06* (2013.01); *A61P 35/00* (2018.01); *C12N 15/113* (2013.01); *A61K 9/5031* (2013.01); *A61K 2300/00* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 5,654,009 | A * | 8/1997 | Hata | A61K 9/1652 424/490 |
| 8,137,697 | B1 * | 3/2012 | Sung | A61K 9/0009 424/489 |
| 8,361,139 | B2 * | 1/2013 | Flanagan | A61L 31/088 424/423 |
| 8,647,661 | B1 | 2/2014 | Sachdeva et al. | |
| 8,865,206 | B1 | 10/2014 | Sachdeva et al. | |
| 2007/0031844 | A1 | 2/2007 | Khvorova et al. | |
| 2008/0311040 | A1 | 12/2008 | Berry et al. | |
| 2009/0163435 | A1 | 6/2009 | Bader et al. | |
| 2010/0004584 | A1 * | 1/2010 | Sen | A61N 1/327 604/20 |
| 2011/0064664 | A1 | 3/2011 | Lopez-Berestein et al. | |
| 2011/0189299 | A1 | 8/2011 | Okubo et al. | |
| 2013/0122096 | A1 | 5/2013 | Shemi et al. | |
| 2013/0274315 | A1 | 10/2013 | Birrer et al. | |
| 2014/0120170 | A1 * | 5/2014 | Mihov | C08G 69/44 424/501 |

FOREIGN PATENT DOCUMENTS

| | | |
|---|---|---|
| WO | WO 2006-105367 | 10/2006 |
| WO | WO 2007-001448 | 1/2007 |
| WO | WO 2007-076371 | 7/2007 |
| WO | WO 2009-058913 | 5/2009 |
| WO | WO 2009-065181 | 5/2009 |
| WO | WO 2010-059963 | 5/2010 |

OTHER PUBLICATIONS

Katas et al. Journal of Controlled Release 2006 115:216-225 (Year: 2006).*
Tsuritani et al. Calcified Tissue International 2010 86:47-57 (Year: 2010).*
Koukaras et al. Molecular Pharmaceutics 2012 9:2856-2862 (Year: 2012).*
Ragelle et al. Journal of Controlled Release 2014 176:54-53; available online Dec. 31, 2013 (Year: 2014).*
Rojanarata et al. Pharmaceutical Research 2008 25(12):2807-2814 (Year: 2008).*
He et al. International Journal of Pharmaceutics 1998 166:75-88 (Year: 1998).*
Palacio et al. Journal of the Brazilian Chemical Society 2011 22(12):2304-2311 (Year: 2011).*
Gan et al. Colloids and Surface B: Biointerfaces 2005 44:65-73 (Year: 2005).*

(Continued)

*Primary Examiner* — Robert A Wax
*Assistant Examiner* — Caralynne E Helm
(74) *Attorney, Agent, or Firm* — Parker Highlander PLLC

(57) ABSTRACT

Disclosed are nanoparticles for the delivery of a therapeutic agent or a diagnostic agent to a subject that include a chitosan and a polyphosphate, wherein the chitosan nanoparticles are coated with polylactic acid. Methods of delivering a therapeutic agent or a diagnostic agent to a subject for the treatment or prevention of a disease are also disclosed. For example, the treatment of ovarian cancer in a subject by inhibiting the expression of ZNF034 is disclosed.

4 Claims, 32 Drawing Sheets
Specification includes a Sequence Listing.

(56) References Cited

OTHER PUBLICATIONS

Dehousse et al. International Journal of Biological Macromolecules 2010 46:342-349 (Year: 2010).*

Serra "Investigating Cancer Molecular Genetics using Genome-wide RNA Interference Screens: A Dissertation" 2013 287 pages (Year: 2013).*

Babu et al., "Chitosan Coated Polylactic Acid Nanoparticle-Mediated Combinatorial Delivery of Cisplatin and siRNA/Plasmid DNA Chemosensitizes Cisplatin-Resistant Human Ovarian Cancers and Viral Infections," *Mol. Pharm.,* 11:2720-2733, 2014.

Draz et al., "Nanoparticle-Mediated Systemic Delivery of siRNA for Treatment of Cancers and Viral Infections," *theranostics,* 4:872-892, 2014.

International Preliminary Report on Patentability issued in corresponding PCT Application No. PCT/US2016/038970, dated Sep. 30, 2016.

International Search Report and Written Opinion issued in corresponding PCT Application No. PCT/US2016/038970, dated Sep. 30, 2016.

* cited by examiner

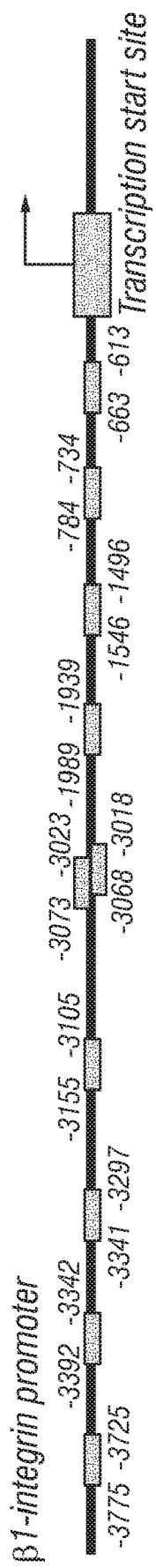
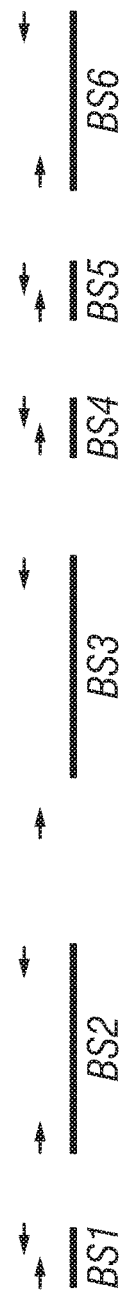
FIG. 3B
FIG. 3C

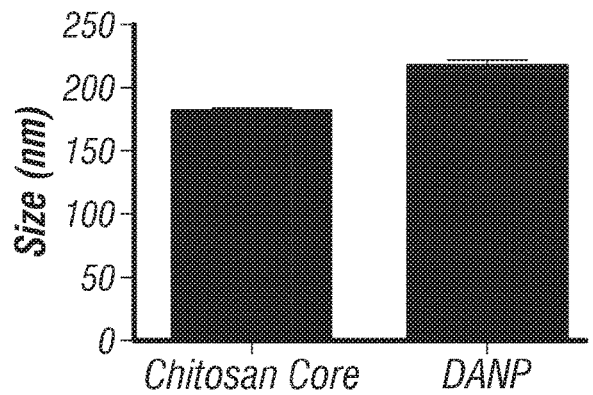
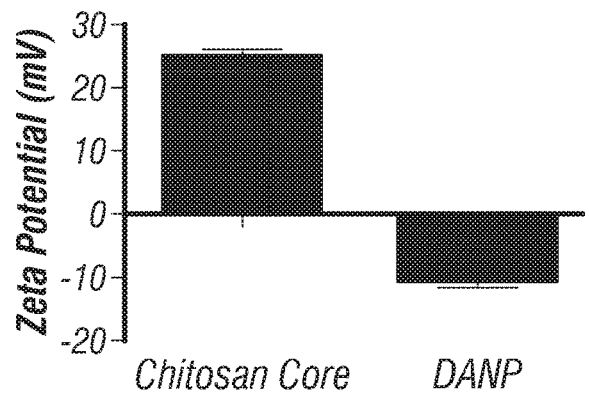
FIG. 5A
FIG. 5B
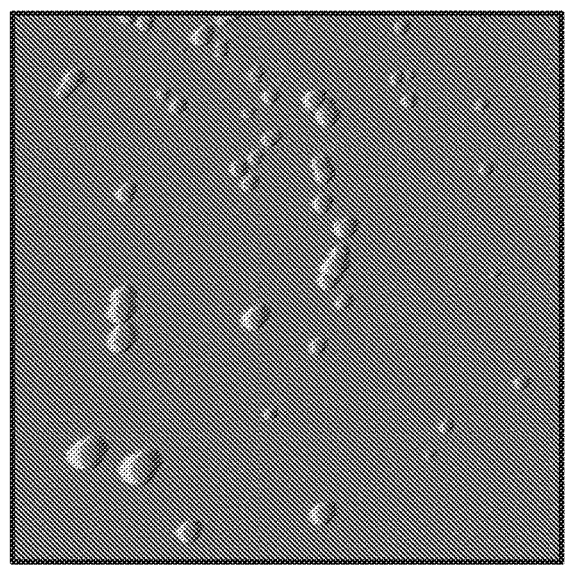
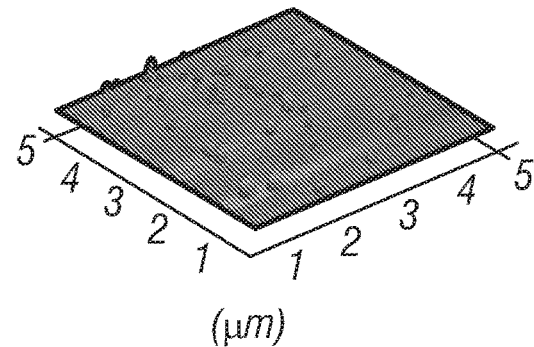
FIG. 5C

1. Control siRNA + Empty vector
2. Control siRNA + ZNF304 Overexpressing Vector
3. Control siRNA + ZNF304 Mutant Vector (insensitive for ZNF304 siRNA)
4. ZNF304 siRNA + Empty vector
5. ZNF304 siRNA + ZNF304 Overexpressing Vector
6. ZNF304 siRNA + ZNF304 Mutant Vector (insensitive for ZNF304 siRNA)

DUAL ASSEMBLY NANOPARTICLES

The present application is a national phase application under 35 U.S.C. § 371 of International application number PCT/US2016/038970, filed Jun. 23, 2016, which claims the priority benefit of U.S. provisional application No. 62/184,014, filed Jun. 24, 2015, the entire contents of each of which is incorporated herein by reference.

This invention was made with government support under Grant No. 5U54CA151668-04 awarded by the National Cancer Institute. The government has certain rights in the invention.

Pursuant to 37 C.F.R. 1.821(c), a sequence listing is submitted herewith as an ASCII compliant text file named "UTSCP1270US_ST25.txt", created on Dec. 5, 2017 and having a size of 14 kilobytes. The content of the aforementioned file is hereby incorporated by reference in its entirety.

BACKGROUND OF THE INVENTION

1. Field of the Invention

The present invention relates generally to the fields of molecular biology, pharmaceuticals, and oncology. More particularly, it concerns dual assembly nanoparticles comprising an inner aqueous polymer coated with a hydrophobic component.

2. Description of Related Art

Ovarian carcinoma (OC) has the highest mortality rate among gynecologic malignancies. In the United States in 2014, over 21,000 patients will be diagnosed with OC, and more than 14,000 will die (Siegel et al., 2014). The most common histological subtype is high-grade serous ovarian carcinoma (HGSOC), which is associated with poor survival most likely due to the advanced stage of disease and widespread metastases at presentation, related to lack of early symptoms and detection. The rapid spread of HGSOC is based on its propensity to seed the peritoneal cavity, leading to ascites formation (Naora and Montell, 2005; Kipps et al., 2013); this highlights the need for a deeper understanding of the molecular mechanisms that regulate ovarian carcinoma growth and progression. The Cancer Genome Atlas (TCGA) is paving the way for new target identification that may influence pathophysiology and patient outcome. This dataset provides a comprehensive genomic, epigenomic and a number other analysis, which will assist in the detection of biological and clinically relevant information on HGSOC samples (Vaughan et al., 2011).

SUMMARY OF THE INVENTION

In a first embodiment there is provided a dual assembly nanoparticle comprising an inner core comprising an aqueous polymer and an outer coat comprising polylactic acid. In some aspects, a particle of the embodiments may be used for delivery of therapeutics and may be used for sustained release of payload molecules. For example, in some aspects, a RNA such as a non-coding RNA (e.g., a miRNA or siRNA) can be incorporated in the inner core of a particle of the embodiments. In still further aspects, the outer coat of a particle can comprise hydrophobic compounds (e.g., therapeutic or imaging agents).

In a first embodiment, a nanoparticle is provided, comprising (a) an inner core comprising a chitosan; and (b) an outer coat comprising polylactic acid. In a further embodiment, a nanoparticle is provided comprising at least one therapeutic agent or diagnostic agent. In further aspects, the inner core of a particle of the embodiments comprises chitosan and a polyphosphate anion.

In some aspects, a nanoparticle of the embodiments comprises at least a first therapeutic or diagnostic agent. In certain aspects, the therapeutic or diagnostic agent is a small molecule, a peptide, a polypeptide, a protein, an antibody, an antibody fragment, or a nucleic acid molecule (e.g., a DNA or RNA). In some aspects, a therapeutic agent or diagnostic agent is comprised in the inner core of a particle. In further aspects, a therapeutic agent or diagnostic agent is comprised in the outer coat of a particle. In further aspects, at least one therapeutic agent or diagnostic agent is comprised in the inner core and at least one therapeutic agent or diagnostic agent is comprised in the outer coat.

In particular embodiments, the nanoparticle of the embodiments comprises at least a first therapeutic agent. For example, the therapeutic agent is can be a nucleic acid molecule, such as a RNA. In certain aspects, the RNA is a small interfering RNA (siRNA), a short hairpin RNA (shRNA) or a micro RNA (miRNA). In further aspects, the RNA is comprised in the inner core of a nanoparticle, such as a core comprising chitosan and a polyphosphate anion. In further aspects, the nanoparticle comprises a nucleic acid molecule in the inner core (e.g., a RNA) and at least one therapeutic agent or diagnostic agent in the outer coat. In particular aspects, a RNA for use according to the embodiments is a RNA that inhibits the expression of a gene that encodes ZNF304, CNTFR, MAGED1, or NR2F2. Thus, in some aspects, a nanoparticle is provided comprising an inner core comprising chitosan, a polyphosphate anion and RNA that inhibits expression of ZNF304, CNTFR, MAGED1, or NR2F2.

In certain aspects, a particle of the embodiments comprises an inner core comprising chitosan that is ionically or covalently bonded to the polyphosphate anion. For example, the polyphosphate anion can comprise tripolyphosphate. In some aspects, the weight ratio of the chitosan to the polyphosphate anion is about 2 to about 10. For example, the weight ratio of the chitosan to the polyphosphate anion can be between about 2-8, 2-7, 2-6, 2-5, 2-4, 2.5-4 or 2.5-3.5. In specific aspects, the weight ratio of the chitosan to the polyphosphate is about 3.

In a further embodiment, a method is provided for delivering a therapeutic agent and/or diagnostic agent to a subject comprising administering to the subject a pharmaceutical composition comprising the nanoparticle of the embodiments. In some aspects, the subject is a mammalian subject, such a companion animal (e.g., a dog or cat), a livestock animal or a primate (e.g., a human).

In certain preferred aspects, a subject for treatment according to embodiments has or is diagnosed with a disease. In certain aspects, the disease is an autoimmune disease, an infectious disease or a cancer. For example, the cancer is breast cancer, lung cancer, prostate cancer, ovarian cancer, brain cancer cell, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, intestinal cancer, lymphoma, or leukemia.

Thus, in certain embodiments there is provided a method of treating a disease, such as an autoimmune disease, an infectious disease or a cancer, in a subject comprising administering an effective amount nanoparticles according to the embodiments to the subject.

In certain specific aspects, the cancer is an ovarian cancer and a nanoparticle of the embodiments comprises a therapeutic agent including a nucleic acid that inhibits the expression of a gene that encodes ZNF304. For example, the nucleic acid can be a siRNA, shRNA or a nucleic acid encoding a siRNA or shRNA. In certain aspects, the nucleic acid an inhibitory nucleic acid comprising about or at least about 18, 19, 20, 21, 22 or 23 contiguous nucleotides that are complimentary to a ZNF304-coding mRNA (see, e.g., NCBI accession no. NM_001290318.1, which is incorporated herein by reference). In certain aspects, the siRNA comprises a sequence at least about 90% or 95% identical to SEQ ID NO: 12 or SEQ ID NO: 14.

Further aspects of the embodiments concern administering an additional anti-cancer therapy to the subject. For example, the additional anticancer therapy is chemotherapy, radiation therapy, surgical therapy, immunotherapy, gene therapy, or a combination thereof. For example, in some cases, the additional anti-cancer therapy can be a chemotherapy, which is administered before, after or essentially concomitantly with a nanoparticle composition of the embodiments. In particular aspects, the additional anticancer therapy is taxane, paxlitaxel, or cisplatin. In still further aspects, a further chemotherapeutic agent may be incorporated into a nanoparticle according to the embodiments.

In certain aspects, a nanoparticle composition of the embodiments is administered intravenously, intradermally, intraarterially, intraperitoneally, intralesionally, intracranially, intraarticularly, intraprostaticaly, intrapleurally, intratracheally, intravitreally, intravaginally, intrarectally, intratumorally, intramuscularly, intraperitoneally, subcutaneously, subconjunctival, intravesicularlly, mucosally, intrapericardially, intraumbilically, intraocularally, intrathecally, locally, by injection, by infusion, by continuous infusion, by localized perfusion bathing target cells directly, via a catheter, or via a lavage. For example, the composition may be administered by injection or infusion.

In yet still a further embodiment there is provided a composition comprising a population of particles in accordance with the embodiments. In certain aspects, the composition comprises $10^3$ to $10^{16}$, $10^4$ to $10^{15}$, $10^5$ to $10^{14}$, $10^6$ to $10^{14}$, $10^6$ to $10^{15}$ or $10^6$ to $10^{16}$ particles. In some aspects, the particles are comprised in a pharmaceutically acceptable carrier. In still further aspects, the particles may, themselves be encapsulated in a coating, such as a pill or capsule. In certain aspects, a coating for use in encapsulating particles is a dissolvable coating.

In one embodiment, a nanoparticle is provided for use in delivering a therapeutic agent or diagnostic agent to a subject in need thereof. In some aspects, the subject is a human. In some aspects, the subject has a disease. In some aspects, the disease is a cancer, such as, for example, breast cancer, lung cancer, prostate cancer, ovarian cancer, brain cancer cell, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, intestinal cancer, lymphoma, or leukemia. In some aspects, the cancer is ovarian cancer and the therapeutic agent comprises a nucleic acid that inhibits the expression of a gene that encodes ZNF304. In some aspects, the nucleic acid is a siRNA or a nucleic acid encoding a siRNA. In some aspects, the siRNA comprises the sequence of SEQ ID NO: 12 or SEQ ID NO: 14. In some aspects, the nanoparticle is formulated for intravenous administration, intraperitoneal administration, intratracheal administration, intratumoral administration, intramuscular administration, endoscopical administration, intralesional administration, percutaneous administration, subcutaneous administration, regional administration, or for direct injection or perfusion.

In one embodiment, the use of a nanoparticle comprising a therapeutic agent in the manufacture of a medicament for the treatment of a disease in a subject is provided. In some aspects, the subject is a human. In some aspects, the disease is a cancer. In some aspects, the cancer is breast cancer, lung cancer, prostate cancer, ovarian cancer, brain cancer cell, liver cancer, cervical cancer, colon cancer, renal cancer, skin cancer, head and neck cancer, bone cancer, esophageal cancer, bladder cancer, uterine cancer, lymphatic cancer, stomach cancer, pancreatic cancer, testicular cancer, intestinal cancer, lymphoma, or leukemia. In some aspects, the cancer is ovarian cancer and the therapeutic agent comprises a nucleic acid that inhibits the expression of a gene that encodes ZNF304. In some aspects, the nucleic acid is a siRNA or a nucleic acid encoding a siRNA. In some aspects, the siRNA comprises the sequence of SEQ ID NO: 12 or SEQ ID NO: 14.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-G. ZNF304 associates with ITGB1 promoter and regulates β1 integrin expression. (A) Western blot analysis of basal protein expression levels of ZNF304 and β1 integrin in HIO180 (non-transformed ovarian cell line) and seven ovarian carcinoma cell lines. (B) The 10 predicted binding sites of ZNF304 in the ITGB1 promoter on the basis of support vector machine scores using an online tool, which is available on the world wide web at compbio.cs.princeton.edu/zf/. Sequences of the 10 predicted binding sites are provided as SEQ ID NOs: 2-11. (C) ITGB1 promoter with 10 predicted binding sites and six primer sets that were designed for the 10 predicted binding sites. (D) Chromatin immunoprecipitation (ChIP) analyses with ZNF304 antibody in HeyA8 cells. Relevant sequences were quantified by polymerase chain reaction with six pre-designed primers subsequent to ChIP assay. (E) Densitometric analysis of ChIP data. Sequence and antibody specificity controls were included. Left columns are ZNF304; right columns are IgG. Data are presented as percentage of input. (F) Luciferase activity in control siRNA (black) or ZNF304 siRNA (grey) treated HeyA8 cells. Fold of induction was calculated after normalization with empty vector. Data are presented as mean±s.e.m. of n≥3 experimental groups. *P≥0.05, P≥0.01, *P≥0.001 (Student's t-test). Luciferase activity was inhibited after control siRNA treatment or ZNF304 siRNA treatment in BS1-vector-transfected cells, in BS2-vector-transfected cells, and in BS-3-vector-transfected cells. (G) Luciferase activity increased after transfection of ZNF304-expressing vector into BS1-, BS2-, and BS3-vector-transfected HeyA8 cells. Data are presented as mean±s.e.m. of n≥3 experimental groups. *P≥0.05, P≥0.01, *P≥0.001 (Student's t-test).

FIGS. 5A-F. Sustained in vivo ZNF304 gene silencing. (A) Size and (B) zeta potential of DANP determined by Zeta Sizer. (C) Atomic Force Microscopy images of DANP showing the morphology and size distribution of particles. (D) Biodistribution of rhodamine 6G labeled DANP in vivo. Tumor and the major organs were removed 24 h after a single administration of rhodamine 6G labeled DANP. The nanoparticles were monitored using fluorescent microscopy and representative images were taken at 20× (left) and 40× magnification (center). Scale Bar, 100 μm. Number of nanoparticles was counted at 5 fields per slide (right). Data are presented as means±standard error of the mean (SEM). (E) Sustained in vivo ZNF304 silencing in HeyA8 orthotopic model of OC. Tumors were removed and analyzed by immunoblotting at 3, 7, and 14 days after a single administration of ZNF304 siRNA-DANP. (F) Effect of DANP, DANP-Control siRNA and DANP-ZNF304 siRNA on cytokine levels in plasma at 72 h, after a single intravenous administration. Inflammatory Cytokine responses were assessed in the serum of C57 black mice. Mice were treated with single i.v. injections of DANP alone (n=6), DANP-Control siRNA (n=6), and DANP-ZNF304 siRNA (n=6) and no treatment (n=2) and serum was collected after 72 h using cardiac puncture. A Luminex assay designed to detect 12 pro-inflammatory cytokines was used. In order from front to back, columns for each data point are DANP-ZNF304 siRNA, DANP-Control siRNA, DANP, and No Treatment.

DESCRIPTION OF ILLUSTRATIVE EMBODIMENTS

Figure 1A:
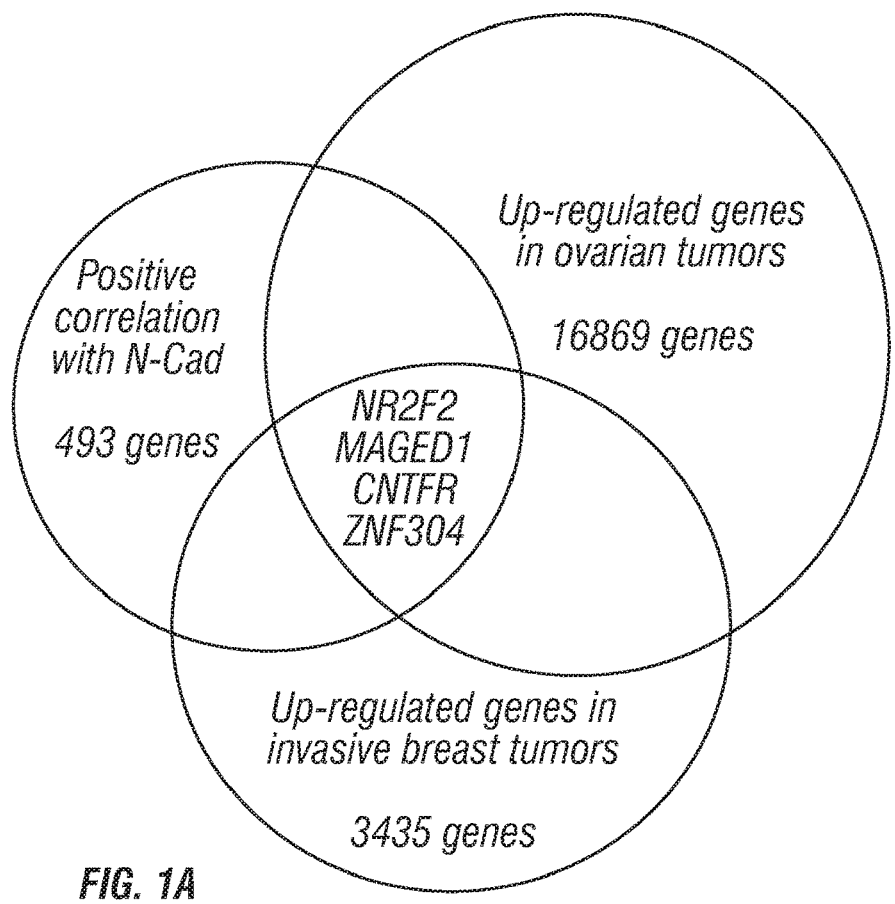
FIGS. 1A-E. Significance of zinc finger protein 304 expression in human ovarian carcinoma. (A) Graphical representation of computational analysis using The Cancer Genome Atlas (TCGA) high-grade serous ovarian carcinoma dataset. (B) The probability of survival in ovarian carcinoma patients analyzed in the training set (2/3 of cases) (P<0.05, Log-rank test) and (C) in the validation set (1/3 of cases) (P<0.05, Log-rank test). Kaplan-Meier curves indicate that high ZNF304 expression is a predictor of poor overall survival in patients with ovarian carcinoma (n=88, P=0.03, Log-rank test). Top lines are "low" and bottom lines are "high." (D) Western Blot analysis of ZNF304 protein expression and (E) RT-PCR analysis of ZNF304 mRNA levels in seven ovarian cell lines.

RNA interference is a highly effective method for gene silencing owing to its sequence specificity. Synthetic siRNAs can strongly inhibit the expression of a target protein and hold great promise as therapeutic tools for targeted gene silencing in cancer therapy. However, the use of siRNAs has been hampered due to their rapid degradation by serum nucleases, poor cellular uptake, and rapid renal clearance following systemic administration. As such, safe and non-toxic nanocarriers for siRNA are needed.

Chitosan nanoparticles have been previously developed and characterized for systemic delivery of siRNA (Lu et al., 2010; Han et al., 2010), and chitosan-based carriers are one of the non-viral vectors that have gained increasing interest as a safe and cost-effective system for siRNA delivery. Although chitosan nanoparticles are an efficient RNA interference delivery system, weekly administration is required since the target downregulation lasts only for seven days after a single administration.

Polylactic acid (PLA) is a biodegradable polymeric material with low toxicity and high biocompatibility and bioabsorbability in vivo. The low hydrophilicity and high crystallinity of PLA reduces its degradation rate. In the studies described herein, PLA was used to coat siRNA-incorporated chitosan nanoparticles to generate dual assembly nanoparticles (DANP) to maintain a constant siRNA level over an extended period of time with minimal side effects.

ZNF304, a novel zinc finger protein whose elevated expression correlates with a poor prognosis, was used as an exemplary target protein that has a strong impact on overall survival and progression free survival in patients. A single administration of ZNF304 siRNA-loaded DANP led to two-week silencing of ZNF304 protein, along with increased anoikis and reduced tumor growth, in an in vivo model of ovarian carcinoma.

I. Chitosan and Analogs Thereof

The nanoparticles of the present invention include chitosan as a component. Generally, chitosans are a family of cationic, binary hetero-polysaccharides composed of (1→4)-linked 2-acetamido-2-deoxy-β-D-glucose (GlcNAc, A-unit) and 2-amino-2-deoxy-β-D-glucose, (GlcN; D-unit) (Varum et al., 1991). The chitosan has a positive charge, stemming from the de-acetylated amino group (—NH$_3^+$). Chitosan, chitosan derivatives, or salts (e.g., nitrate, phosphate, sulphate, hydrochloride, glutamate, lactate or acetate salts) of chitosan may be used and are included within the meaning of the term "chitosan." As used herein, the term "chitosan derivatives" is intended to include ester, ether, or other derivatives formed by bonding of acyl and/or alkyl groups with —OH groups, but not the NH$_2$ groups, of chitosan. Examples are O-alkyl ethers of chitosan and O-acyl esters of chitosan. Modified chitosans, particularly those conjugated to polyethylene glycol, are also considered "chitosan derivatives." Many chitosans and their salts and derivatives are commercially available (e.g., SigmaAldrich, Milwaukee, Wis.).

Methods of preparing chitosans and their derivatives and salts are also knowm, such as boiling chitin in concentrated alkali (50% w/v) for several hours. This produces chitosan wherein 70%-75% of the N-acetyl groups have been removed. A non-limiting example of a chitosan, wherein all of the N-acetyl groups have been removed, is shown below:

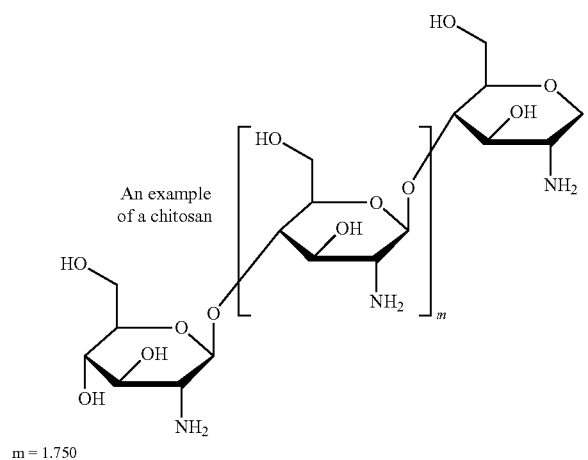

An example of a chitosan m = 1,750

Chitosans may be obtained from any source known to those of ordinary skill in the art. For example, chitosans may be obtained from commercial sources. Chitosans may be obtained from chitin, the second most abundant biopolymer in nature. Chitosan is prepared by N-deacetylation of chitin. Chitosan is commercially available in a wide variety of molecular weight (e.g., 10-1000 kDa) and usually has a degree of deacetylation ranging between 70%-90%.

The chitosan (or chitosan derivative or salt) used preferably has a molecular weight of 4,000 Dalton or more, preferably in the range 25,000 to 2,000,000 Dalton, and most preferably about 50,000 to 300,000 Dalton. Chitosans of different molecular weights can be prepared by enzymatic degradation of high molecular weight chitosan using chitosanase or by the addition of nitrous acid. Both procedures are well known to those skilled in the art and are described in various publications (Li et al., 1995; Allan and Peyron, 1995; Domard and Cartier, 1989). The chitosan is water-soluble and may be produced from chitin by deacetylation to a degree of greater than 40%, preferably between 50% and 98%, and more preferably between 70% and 90%.

Some methods of producing chitosan involve recovery from microbial biomass, such as the methods taught by U.S. Pat. No. 4,806,474 and U.S. Patent Application No. 2005/0042735, herein incorporated by reference. Another method, taught by U.S. Pat. No. 4,282,351, teaches only how to create a chitosan-beta-glucan complex.

The chitosan, chitosan derivative, or salt used in the present invention is water soluble. Chitosan glutamate is water soluble. By "water soluble" it is meant that that the chitosan, chitosan derivative, or salt dissolves in water at an amount of at least 10 mg/ml at room temperature and atmospheric pressure. The chitosan, chitosan derivative, or salt used in the present invention has a positive charge.

Additional information regarding chitosan and chitosan derivatives can be found in U.S. Patent App. Pub. Nos. 2007/0167400, 2007/0116767, 2007/0311468, 2006/0277632, 2006/0189573, 2006/0094666, 2005/0245482, 2005/0226938, 2004/0247632, and 2003/0129730, each of which is herein specifically incorporated by reference.

II. Methods of Making LPA-Coated Chitosan Nanoparticles

Preparation of Chitosan Solution

For the preparation of chitosan nanoparticles, several techniques are available, such as emulsion, ionotropic gelation, reverse micellar, solvent evaporation, spray drying, and coacervation. Chitosan (such as a powder of chitosan or a derivative thereof or a salt of chitosan or a salt of a derivative of chitosan) is dissolved in a suitable solvent to form a solution. For example, the solvent may be water, acetic acid, or hydrochloric acid. The chitosan-containing solution that is formed may optionally be centrifuged to remove contaminants, although removal of all contaminants is not required.

The pH of the chitosan solution may then be adjusted such that the pH is in a range of about 3.5 to about 5.5. In more particular embodiments, the pH of the chitosan solution is adjusted so that it is in the range of about 4.0 to about 5.0. In still further particular embodiments, the pH of the chitosan solution is adjusted so that it is in the range of about 4.4 to about 5. In a particular embodiment, the pH of the chitosan solution is adjusted such that the pH is about 4.6. The pH can be adjusted by any method known to those of ordinary skill in the art. For example, the pH may be adjusted by the addition of NaOH, such as 10 N NaOH.

One or more additional components can optionally be added to the chitosan solution. Examples of such components include a therapeutic or diagnostic agent, such as any of those agents discussed below.

Preparation of Polyphosphate Solution

Polyphosphates are phosphate polymers linked between hydroxyl groups and hydrogen atoms. A polyphosphate anion as used herein refers to a compound of the formula:

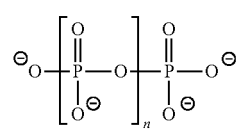

wherein n is an integer ranging from 2-10.

A "polyphosphate" as used herein refers to a compound of formula (II):

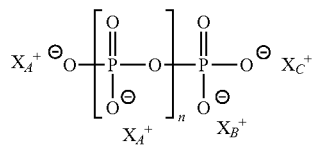

wherein n is an integer ranging from 2-10; and $X_A$, $X_B$, $X_C$ and $X_n$ are each independently any monovalent cation (e.g., $H^+$, $Na^+$, $K^+$, $Cs^+$, $NH_4^+$).

In particular embodiments of the present invention, n=3, and the polyphosphate is a tripolyphosphate. In more particular embodiments, n=3 and X is Nat, and the polyphosphate is sodium tripolyphosphate.

In particular embodiments of the present invention, sodium tripolyphosphate is utilized in the nanoparticles and methods set forth herein. Sodium tripolyphosphate (STPP, pentasodium triphosphate, or sodium triphosphate), with formula $Na_5P_3O_{10}$, is a polyphosphate of sodium. It is the sodium salt of triphosphoric acid. Tripolyphosphates have a wide variety of applications, including as automatic dishwasher detergents, laundry detergents, cleaners, ceramics, food, and beverages.

Tripolyphosphates can be obtained from natural or commercial sources, or can be chemically synthesized. Information regarding the synthesis of sodium tripolyphosphate can be found in U.S. Patent Pub. No. 2002/0170849, herein specifically incorporated by reference.

In particular embodiments, the polyphosphate is a tripolyphosphate (TPP). The solvent may be any solvent, such as any of those solvents set forth elsewhere in this specification. For example, the concentration of TPP in the solution may be about 0.01% to about 1.00%. In more particular embodiments, the concentration is about 0.1% to about 0.9%. In more particular embodiments, the concentration is about 0.1% to about 0.5%. In even more particular embodiments, the concentration is about 0.2% to about 0.3%. In a particular embodiment, the concentration of TPP is about 0.25%.

In some embodiments, a therapeutic or diagnostic agent is added to the polyphosphate solution. For example, the agent may be a therapeutic agent, such as siRNA.

C. Mixing of Chitosan and Polyphosphate Solutions

The chitosan solution may be added to the polyphosphate solution. As discussed above, the polyphosphate solution optionally includes one or more therapeutic or diagnostic agents. In particular embodiments, the mixture is allowed to incubate at 4° C. for a period of time, such as one hour. This step assists with stabilization of the particles. Mixing of the chitosan solution and the polyphosphate solution results in the formation of nanoparticles. The nanoparticles are composed of chitosan, polyphosphate, and any therapeutic or diagnostic agent(s) that were included.

D. Coating of Chitosan Nanoparticles with PLA

The biodegradable PLA useful in the present invention has a weight average molecular weight preferably in the range of 30,000-800,000, more preferably in the range of 40,000-400,000, and particularly preferably in the range of 70,000-12,000. The PLA suitable in the present invention includes, but is not limited to, poly-L-lactic acid (PLLA), poly-D-lactic acid (PDLA), poly-D,L-lactic acid (PDLLA), and a mixture thereof.

After preparation of chitosan nanoparticles, different amounts of PLA and different organic solvents, such as acetone, dichloromethane, chloroform can be used to coat the nanoparticles with PLA. One or more additional components can optionally be added to the PLA solution. Examples of such components include a therapeutic or diagnostic agent, such as any of those agents discussed below.

E. Purification of Formed Nanoparticles

The nanoparticles can be purified using any method known to those of ordinary skill in the art. In particular embodiments, the nanoparticles may be purified by centrifugation and removal of supernatant. For example, centrifugation may be at 12000 rpm for about 30 min to about 60 min. Centrifugation may be repeated once or more than once. In particular embodiments, centrifugation is repeated three times.

F. Analysis of Formed Nanoparticles

Nanoparticles that are formed by the present methods can be analyzed using any method and technique known to those of ordinary skill in the art. For example, particle size may be measured by dynamic light scattering, chemical characterization may be measured by nuclear magnetic resonance (NMR), surface characteristics may be measured by atomic force microscopy (AFM), and morphological properties may be measured by scanning electron microscopy (SEM).

The nanoparticles that are formed can be of any size. For example, the particles may be of a size in the range of about 10 nm to about 1000 nm in size or greater. In some embodiments, the particles are of a size in the range of about 1 μm to 1000 μm in size. In some embodiments, particle size is heterogeneous and poorly defined. If desired, particle size may be reduced using any method known to those of ordinary skill in the art. The particle size can be controlled using standard techniques, such as sieving.

G. Storage of Formed Nanoparticles

The nanoparticles may be stored using any method known to those of ordinary skill in the art. The nanoparticles may be stored at 4° C. until ready for use.

H. Optional Ingredients

The particles of the present invention may optionally include one or more additional ingredients. Examples of additional ingredients include, but are not limited to, sugars, such as sucrose and trehalose; polyols, such as mannitol and sorbitol; surfactants, such as polysorbates; amino acids, such as glycine; and polyethylene glycol. The total amount of additional ingredients may be up to a total of about 10% by weight of the nanoparticle.

III. Therapeutic and Diagnostic Agents

A "therapeutic agent" as used herein refers to any agent that can be administered to a subject for the purpose of obtaining a therapeutic benefit of a disease or health-related condition. For example, nanoparticles that include a therapeutic agent may be administered to a subject for the purpose of reducing the size of a tumor, reducing or inhibiting local invasiveness of a tumor, or reducing the risk of development of metastases.

A "diagnostic agent" as used herein refers to any agent that can be administered to a subject for the purpose of diagnosing a disease or health-related condition in a subject. Diagnosis may involve determining whether a disease is present, whether a disease has progressed, or any change in disease state.

The therapeutic or diagnostic agent may be a small molecule, a peptide, a protein, a polypeptide, an antibody, an antibody fragment, a DNA, or an RNA. In particular embodiments, the therapeutic or diagnostic agent is a siRNA.

The therapeutic agent or diagnostic agent can be any such agent known to those of ordinary skill in the art. For example, the therapeutic agent may be an anti-inflammatory agent, an anti-infective agent, an agent that can be applied in the treatment of a hyperproliferative disease, such as cancer, an agent that can be applied in the treatment of a degenerative disease, and so forth.

Other examples of therapeutic agents include, but are not limited to, agents for the prevention of restenosis, agents for treating renal disease, agents used for intermittent claudication, agents used in the treatment of hypotension and shock, angiotensin converting enzyme inhibitors, antianginal agents, anti-arrhythmics, anti-hypertensive agents, antiotensin ii receptor antagonists, antiplatelet drugs, b-blockers b1 selective, beta blocking agents, botanical product for cardiovascular indication, calcium channel blockers, cardiovascular/diagnostics, central alpha-2 agonists, coronary vasodilators, diuretics and renal tubule inhibitors, neutral endopeptidase/angiotensin converting enzyme inhibitors, peripheral vasodilators, potassium channel openers, potassium salts, anticonvulsants, antiemetics, antinauseants, antiparkinson agents, antispasticity agents, cerebral stimulants, agents that can be applied in the treatment of trauma, agents that can be applied in the treatment of Alzheimer disease or dementia, agents that can be applied in the treatment of migraine, agents that can be applied in the treatment of neurodegenerative diseases, agents that can be applied in the treatment of kaposi's sarcoma, agents that can be applied in the treatment of AIDS, cancer chemotherapeutic agents, agents that can be applied in the treatment of immune disorders, agents that can be applied in the treatment of psychiatric disorders, analgesics, epidural and intrathecal anesthetic agents, general, local, regional neuromuscular blocking agents sedatives, preanesthetic adrenal/acth, anabolic steroids, agents that can be applied in the treatment of diabetes, dopamine agonists, growth hormone and analogs, hyperglycemic agents, hypoglycemic agents, oral insulins, largevolume parenterals (lvps), lipid-altering agents, metabolic studies and inborn errors of metabolism, nutrients/amino acids, nutritional lvps, obesity drugs (anorectics), somatostatin, thyroid agents, vasopressin, vitamins, corticosteroids, mucolytic agents, pulmonary anti-inflammatory agents, pulmonary surfactants, antacids, anticholinergics, antidiarrheals, antiemetics, cholelitholytic agents, inflammatory bowel disease agents, irritable bowel syndrome agents, liver agents, metal chelators, miscellaneous gastric secretory agents, pancreatitis agents, pancreatic enzymes, prostaglandins, prostaglandins, proton pump inhibitors, sclerosing agents, sucralfate, anti-progestins, contraceptives, oral contraceptives, not oral dopamine agonists, estrogens, gonadotropins, GNRH agonists, GHRH antagonists, oxytocics, progestins, uterine-acting agents, anti-anemia drugs, anticoagulants, antifibrinolytics, antiplatelet agents, antithrombin drugs, coagulants, fibrinolytics, hematology, heparin inhibitors, metal chelators, prostaglandins, vitamin K, anti-androgens, aminoglycosides, antibacterial agents, sulfonamides, cephalosporins, clindamycins, dermatologics, detergents, erythromycins, anthelmintic agents, antifungal agents, antimalarials, antimycobacterial agents, antiparasitic agents, antiprotozoal agents, antitrichomonads, antituberculosis agents, immunomodulators, immunostimulatory agents, macrolides, antiparasitic agents, corticosteroids, cyclooxygenase inhibitors, enzyme blockers, immunomodulators for rheumatic diseases, metalloproteinase inhibitors, nonsteroidal anti-inflammatory agents, analgesics, antipyretics, alpha adrenergic agonists/blockers, antibiotics, antivirals, beta adrenergic blockers, carbonic anhydrase inhibitors, corticosteroids, immune system regulators, mast cell inhibitors, nonsteroidal anti-inflammatory agents, prostaglandins, and proteolytic enzymes.

Examples of diagnostic agents include, but are not limited to, magnetic resonance image enhancement agents, positron emission tomography products, radioactive diagnostic agents, radioactive therapeutic agents, radio-opaque contrast agents, radiopharmaceuticals, ultrasound imaging agents, and angiographic diagnostic agents.

In particular embodiments, the therapeutic agent is a chemotherapeutic agent. A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A); bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In particular embodiments, as discussed above, the therapeutic agent is a siRNA. Examples of such siRNA are discussed in greater detail below.

IV. Inhibitions of Gene Expression and siRNA siNA (e.g., siRNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary. In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90, 100, 150, 200, 250, 300, 350, 400, 450, 500 or more contiguous nucleobases, including all ranges therein. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

Agents of the present invention useful for practicing the methods of the present invention include, but are not limited to siRNAs. Typically, introduction of double-stranded RNA (dsRNA), which may alternatively be referred to herein as small interfering RNA (siRNA), induces potent and specific gene silencing, a phenomena called RNA interference or RNAi. This phenomenon has been extensively documented in the nematode *C. elegans* (Fire et al., 1998), but is widespread in other organisms, ranging from trypanosomes to humans. Depending on the organism being discussed, RNA interference has been referred to as "cosuppression," "post-transcriptional gene silencing," "sense suppression," and "quelling." RNAi is an attractive biotechnological tool because it provides a means for knocking out the activity of specific genes.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition, the size of the siRNA is an important consideration. In some embodiments, the present invention relates to siRNA molecules that include at least about 19-25 nucleotides and are able to modulate gene expression. In the context of the present invention, the siRNA is preferably less than 500, 200, 100, 50, or 25 nucleotides in length. More preferably, the siRNA is from about 19 nucleotides to about 25 nucleotides in length.

A target gene generally means a polynucleotide comprising a region that encodes a polypeptide, or a polynucleotide region that regulates replication, transcription, or translation or other processes important to expression of the polypeptide, or a polynucleotide comprising both a region that encodes a polypeptide and a region operably linked thereto that regulates expression. The targeted gene can be chromosomal (genomic) or extrachromosomal. It may be endogenous to the cell, or it may be a foreign gene (a transgene). The foreign gene can be integrated into the host genome or it may be present on an extrachromosomal genetic construct such as a plasmid or a cosmid. The targeted gene can also be derived from a pathogen, such as a virus, bacterium, fungus, or protozoan, which is capable of infecting an organism or cell. Target genes may be viral and pro-viral genes that do not elicit the interferon response, such as retroviral genes. The target gene may be a protein-coding gene or a non-protein coding gene, such as a gene that codes for ribosomal RNAs, spliceosomal RNA, tRNAs, etc.

Any gene being expressed in a cell can be targeted. Preferably, a target gene is one involved in or associated with the progression of cellular activities important to disease or of particular interest as a research object. Thus, by way of example, the following are classes of possible target genes that may be used in the methods of the present invention to modulate or attenuate target gene expression: developmental genes (e.g., adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), tumor suppressor genes (e.g., APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zacl, ras, MMAC1, FCC, MCC, FUS1, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide), pro-apoptotic genes (e.g., CD95, caspase-3, Bax, Bag-1, CRADD, TSSC3, bax, hid, Bak, MKP-7, PARP, bad, bcl-2, MST1, bbc3, Sax, BIK, and BID), cytokines (e.g., GM-CSF, G-CSF, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 IFN-α, IFN-β, IFN-γ, MIP-1α, MIP-1β, TGF-β, TNF-α, TNF-β, PDGF, and mda7), oncogenes (e.g., ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), and enzymes (e.g., ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, nucleases, pectinesterases, peroxidases, phosphatases, phospholipases, phosphorylases, polygalacturonases, proteinases and peptideases, pullanases, recombinases, reverse transcriptases, topoisomerases, xylanases).

siRNA can be obtained from commercial sources, natural sources, or can be synthesized using any of a number of techniques well-known to those of ordinary skill in the art. For example, one commercial source of predesigned siRNA is Ambion®, Austin, Tex. Another is Qiagen® (Valencia, Calif.). An inhibitory nucleic acid that can be applied in the compositions and methods of the present invention may be any nucleic acid sequence that has been found by any source to be a validated downregulator of a protein of interest.

In one aspect, the invention generally features an isolated siRNA molecule of at least 19 nucleotides, having at least one strand that is substantially complementary to at least ten but no more than thirty consecutive nucleotides of a nucleic acid that encodes a ZNF304 protein (SEQ ID NO: 1), and that reduces the expression of the ZNF304 protein. In a particular embodiment of the present invention, the siRNA molecule has at least one strand that is substantially complementary to at least ten but no more than thirty consecutive nucleotides of the mRNA that encodes ZNF304.

In another particular embodiment, the siRNA molecule is at least 75%, 80%, 85%, or 90% homologous, preferably 95%, 99%, or 100% homologous, to at least 10 contiguous nucleotides of any of the nucleic acid sequences encoding a full-length ZNF304 protein, such as the sequence of NM_020657.3 (GI:594140531), NM_001290318.1 (GI:594140539), or NM_001290319.1 (GI:594140525). Without undue experimentation and using the disclosure of this invention, it is understood that additional siRNAs can be designed and used to practice the methods of the invention.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 2004/0019001 and U.S. Pat. No. 6,673,611 (each of which is incorporated by reference in its entirety). Collectively, all such altered nucleic acids or RNAs described above are referred to as modified siRNAs.

Preferably, RNAi is capable of decreasing the expression of a protein, such as ZNF304, by at least 10%, 20%, 30%, or 40%, more preferably by at least 50%, 60%, or 70%, and most preferably by at least 75%, 80%, 90%, 95% or more.

Certain embodiments of the present invention pertain to methods of inhibiting expression of a gene encoding a protein in a cell. In a specific embodiment, the protein is ZNF304. Introduction of siRNA into cells can be achieved by methods known in the art, including for example, microinjection, electroporation, or transfection of a vector comprising a nucleic acid from which the siRNA can be transcribed. Alternatively, a siRNA can be directly introduced into a cell in a form that is capable of binding to target mRNA transcripts. To increase durability and membrane-permeability the siRNA may be combined or modified with liposomes, poly-L-lysine, lipids, cholesterol, lipofectine or derivatives thereof. In certain aspects cholesterol-conjugated siRNA can be used (see, Song et al., 2003).

V. Methods of Treatment

A. Definitions

"Treatment" and "treating" as used herein refer to administration or application of a therapeutic agent to a subject or performance of a procedure or modality on a subject for the purpose of obtaining a therapeutic benefit of a disease or health-related condition. For example, nanoparticles that include a therapeutic agent may be administered to a subject for the purpose of reducing the size of a tumor, reducing or inhibiting local invasiveness of a tumor, or reducing the risk of development of metastases.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, reduction in the size of a tumor.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

For example, a subject at risk of developing cancer may be administered an effective amount of a composition comprising nanoparticles of the present invention to reduce the risk of development of the cancer compared to the risk in a subject that did not receive nanoparticles.

"Determining prognosis" as used herein refers to predicting the likelihood that a subject with have a certain course or outcome of a disease. For example, in some embodiments determining prognosis involves determining likelihood of reduced survival or likelihood of tumor growth.

Diseases to be Treated or Prevented

Certain embodiments of the present invention concern methods of treating or preventing disease in a subject involving administration of nanoparticles of the present invention. The disease may be any disease that can affect a subject. For example, the disease may be a hyperproliferative disease, an inflammatory disease, or an infectious disease. In particular embodiments, the disease is a hyperproliferative disease. In more particular embodiments, the disease is cancer.

The cancer can be any cancer. For example, the cancer may be a solid tumor, metastatic cancer, or non-metastatic cancer. In certain embodiments, the cancer may originate in the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In certain embodiments, the cancer is human ovarian cancer. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neuro genic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, and/or a neurodegenerative disease).

VI. Pharmaceutical Preparations

Certain of the methods set forth herein pertain to methods involving the administration of a pharmaceutically effective amount of a composition comprising nanoparticles of the present invention.

A. Compositions

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it need to be sterile for such routes of administration as injection.

The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, general safety and purity standards as required by FDA Office of Biologics standards.

The compositions comprising nanoparticles may be extensively dialyzed to remove undesired small molecular weight molecules and/or lyophilized for more ready formulation into a desired vehicle, where appropriate. The active compounds will then generally be formulated for administration by any known route, such as parenteral administration. Methods of administration are discussed in greater detail below.

The present invention contemplates methods using compositions that are sterile solutions for intravascular injection or for application by any other route as discussed in greater detail below. A person of ordinary skill in the art would be familiar with techniques for generating sterile solutions for injection or application by any other route. Sterile injectable solutions are prepared by incorporating the active compounds in the required amount in the appropriate solvent with various of the other ingredients familiar to a person of skill in the art.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, formulations for administration via an implantable drug delivery device, and any other form. One may also use nasal solutions or sprays, aerosols or inhalants in the present invention.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. A person of ordinary skill in the art would be familiar with well-known techniques for preparation of oral formulations.

In certain embodiments, a pharmaceutical composition includes at least about 0.1% by weight of the active agent. The composition may include, for example, about 0.01%. In other embodiments, the pharmaceutical composition includes about 2% to about 75% of the weight of the composition, or between about 25% to about 60% by weight of the composition, for example, and any range derivable therein.

The pharmaceutical composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition must be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, one may use nasal solutions or sprays, aerosols or inhalants in the present invention. Nasal solutions are usually aqueous solutions designed to be administered to the nasal passages in drops or sprays.

Sterile injectable solutions are prepared by incorporating the nanoparticles in the required amount in the appropriate solvent with various of the other ingredients enumerated above, as required, followed by sterilization.

B. Routes of Administration

Upon formulation, nanoparticles will be administered in a manner compatible with the dosage formulation and in such amount as is therapeutically effective.

The nanoparticles can be administered to the subject using any method known to those of ordinary skill in the art. For example, a pharmaceutically effective amount of a composition comprising nanoparticles may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990). In particular embodiments, the composition is administered to a subject using a drug delivery device.

C. Dosage

A pharmaceutically effective amount of the nanoparticles is determined based on the intended goal, for example inhibition of cell division or tumor growth. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

For example, a dose of the therapeutic agent may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

VII. Combination Treatments

Certain embodiments of the present invention provide for the administration or application of one or more secondary forms of therapy for the treatment or prevention of a disease. For example, the disease may be a hyperproliferative disease, such as cancer. The secondary form of therapy may be administration of one or more secondary pharmacological agents that can be applied in the treatment or prevention of cancer.

If the secondary therapy is a pharmacological agent, it may be administered prior to, concurrently, or following administration of the nanoparticles. The interval between the administration of the nanoparticles and the secondary therapy may be any interval as determined by those of ordinary skill in the art. For example, the interval may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations. In some embodiments, the timing of administration of a secondary therapeutic agent is determined based on the response of the subject to the nanoparticles.

Various combinations may be employed. For the example below an nanoparticle therapy is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

A. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein transferase inhibitors, transplatinum, 5-fluorouracil, vincristin, vinblastin and methotrexate and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

Radiotherapy

Other factors that cause DNA damage and have been used extensively include what are commonly known as y-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gen silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., Mycobacterium bovis, Plasmodium falciparum, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VIII. Kits and Diagnostic Agents

In various aspects of the invention, a kit is envisioned containing nanoparticles or ingredients for the formation of nanoparticles of the present invention in one or more suitable container means. A suitable container means is a container that will not react with components of the kit, such as an eppendorf tube, an assay plate, a syringe, a bottle, or a tube. The container may be made from sterilizable materials such as plastic or glass.

In some embodiments, the kit includes a composition comprising nanoparticles in one or more container means. In other embodiments, the kit includes a single container means that comprises chitosan or a solution comprising chitosan, a separate container means that comprises a polyphosphate or a solution that comprises a polyphosphate, designed for admixture prior to use, and yet another separate container means that comprises a polylactic acid solution.

In some further embodiments, the kit includes one or more therapeutic or diagnostic agents. The one or more therapeutic or diagnostic agents may be in the same container means with the polyphosphate and/or chitosan. The kit may further include an instruction sheet that outlines the procedural steps of the methods, and will follow substantially the same procedures as described herein or are known to those of ordinary skill.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Integrative computational analysis and patient data selection. Clinical and expression data (Level 3 Illumina HiSeqv2) for 260 patients were downloaded from The Cancer Genome Atlas portal and were used to analyze the relationship between expression of ZNF304 and overall survival as well as between expressions of ZNF304 and ITGB1. The Spearman's rank-order correlation test was applied to measure the strength of the association between ZNF304 and ITGB1 levels in patient samples in TCGA dataset.

Cell lines and culture. The immortalized non-transformed human ovarian surface epithelial cell line HIO-180 and the human epithelial ovarian carcinoma cell lines HeyA8, MDAH 2774, SKOV3IP1, A2780PAR, and A2780CP20 were maintained as described previously (Kamat et al., 2007; Lu et al., 2007a; Lu et al., 2007b; Sood et al., 2001; Thaker et al., 2004). Taxane resistant HeyA8MDR and SKOV3-TR cells were maintained in Roswell Park Memorial Institute 1640 medium supplemented with 10% fetal bovine serum and 0.1% gentamicin sulfate (Gemini Bio-Products) with or without paclitaxel (300 ng/ml for HeyA8-MDR; 150 ng/ml for SKOV3-TR). The A2780CP20 cell line was developed by sequential exposure of the A2780 cell line to increasing concentrations of cisplatin. All of the cell lines are routinely screened for *Mycoplasma* species (Myco-Alert™ Mycoplasma Detection Kit, Lonza). All in vitro and in vivo experiments were conducted when cells were 70% to 80% confluent.

Western blot analysis. Western blot analysis was performed as previously reported (Landen et al., 2004; Halder et al., 2006). All antibodies used in this study and vendors are listed in Table 1.

TABLE 1

Antibodies used for Western blotting, chromatin immunoprecipitation, and immunohistochemistry

| Target Protein | Source | Cat # | Applications | Dilution |
|---|---|---|---|---|
| Actin-beta | Sigma-Aldrich | A5316 | WB | 1:3500 |
| ZNF304 | Sigma-Aldrich | SAB2106472 | WB, ChIP | 1:1000 |
| B1 integrin | Cell Signaling Technology | 4706S | WB | 1:1000 |
| Akt (pS473) | Cell Signaling Technology | 4060S | WB | 1:1000 |
| Akt | Cell Signaling Technology | 9272 | WB | 1:1000 |
| FAK (pY397) | BD Biosciences | 611722 | WB | 1:1000 |
| PARP | Cell Signaling Technology | 9542 | WB | 1:1000 |
| Src (p416) | Cell Signaling Technology | 6943 | WB | 1:1000 |
| Src | Cell Signaling Technology | 2123 | WB | 1:1000 |
| Paxillin (pY118) | Cell Signaling Technology | 2541 | WB | 1:1000 |
| Paxillin (pY31) | Epitomics | 1228-1 | WB | 1:1000 |
| Paxillin | Cell Signaling Technology | 2542 | WB | 1:1000 |
| Ki67 | Thermo Scientific | RB9043-P | IHC | 1:300 |
| CD31 | BD Biosciences | 53370 | IHC | 1:200 |

Abbreviations:
WB, western blot;
ChIP, chromatin immunoprecipitation;
IHC, immunochemistry;
ZNF304, zinc finger protein 304;
FAK, focal adhesion kinase;
PARP, poly ADP ribose polymerase siRNA constructs and delivery. siRNAs were purchased from Qiagen or Sigma-Aldrich. A non-silencing siRNA that did not share sequence homology with any known human mRNA was used as a control for target siRNA. In vitro transient transfection was performed as described previously (Landen et al., 2005). The ZNF304 and control siRNA sequences are listed in Table 2.

TABLE 2 siRNA sequences used for ZNF304 transfection experiments

| Name | Target Sequence (5'→3') | SEQ ID NO | Source | Cat # |
|---|---|---|---|---|
| ZNF304 siRNA-1 | GAUCACACCUUACACAGAA | 12 | Sigma-Aldrich | SASI_HS01_00189770 |
| ZNF304 siRNA-2 | CUUAUUGAGCACUGGAGAA | 13 | Sigma-Aldrich | SASI_HS01_00189771 |
| ZNF304 siRNA-3 | GCAACAUAAUGGAGAGAAU | 14 | Sigma-Aldrich | SASI_HS01_00189772 |
| Control siRNA | UUCUCCGAACGUGUCACGUUU | 15 | Sigma-Aldrich | WD00909801 |

Invasion and migration assays. Cell migration and invasion assays have been described previously (Spannuth et al., 2009; Kim et al., 2011). For migration/invasion assays, cells were treated with either control or ZNF304 siRNA for 48 h and incubated on migration wells for 24 h. Migrated cells on the bottom of the wells were collected, fixed, stained, and counted by light microscopy. Cells were counted in 10 random fields (×200 final magnification), and the average number of migrated cells was calculated. The percentage of migration was determined by setting control siRNA-treated samples as 100% migration/invasion.

RPPA. This study was conducted in The University of Texas MD Anderson Cancer Center Institution RPPA Core Facility (Tibes et al., 2006). In brief, cellular proteins were denatured by 1% sodium dodecyl sulfate (with beta-mercaptoethanol) and were diluted in five 2-fold serial dilutions in dilution buffer (lysis buffer containing 1% sodium dodecyl sulfate). Serial diluted lysates were arrayed on nitrocellulose-coated slides (Grace Bio-Labs) with an Aushon 2470 arrayer (Aushon BioSystems). A total of 5808 array spots were arranged on each slide, including the spots corresponding to positive and negative controls prepared from mixed cell lysates or dilution buffer, respectively. Each slide was probed with a validated primary antibody plus a biotin-conjugated secondary antibody. Only antibodies with a Pearson correlation coefficient between RPPA and Western blotting of greater than 0.7 were used in the RPPA analysis. Antibodies with a single or dominant band on Western blotting were further assessed by direct comparison to RPPA using cell lines with differential protein expression or modulated with ligands/inhibitors or siRNA for phospho- or structural proteins, respectively. The signal obtained was amplified using a Dako Cytomation-catalyzed system and was visualized by diaminobenzidine colorimetric reaction. The slides were scanned, analyzed, and quantified using customized software (MicroVigene, VigeneTech Inc.) to generate spot intensities. Each dilution curve was fitted with a logistic model ("Supercurve Fitting" developed by the Department of Bioinformatics and Computational Biology at MD Anderson Cancer Center, on the world wide web at bioinformatics.mdanderson.org/OOMPA). This model fits a single curve using all the samples (i.e., dilution series) on a slide, with the signal intensity as the response variable and the dilution steps as independent variables. The fitted curve was plotted with the signal intensities—both observed and fitted—on the y-axis, and the log 2-concentration of proteins plotted on the x-axis for diagnostic purposes. The protein concentrations of each set of slides were then normalized by Tukey's median polish, which was corrected across samples by the linear expression values using the median expression levels of all antibody experiments to calculate a loading correction factor for each sample.

Cell-cycle analysis. Cells were transfected with either control siRNA or ZNF304 siRNA, trypsinized and collected 72 h post transfection. Samples were washed in phosphate-buffered saline solution (PBS) and were fixed in 75% ethanol overnight. Cells were then centrifuged and reconstituted in PBS with propidium iodide (PI; 50 µg/ml), as previously described (Landen et al., 2010). PI fluorescence was assessed by flow cytometry, and the percentage of cells in each cycle was analyzed by FlowJo software.

Chromatin immunoprecipitation assay. HeyA8 cells were cultured in 10% fetal bovine serum to ~75% confluence, and cells were cross-linked with 37% formaldehyde for 20 min and were incubated with glycine (0.125 M) as previously described (Cheema et al., 2003). Cells were lysed, and chromatin was sonicated according to the protocol provided by the kit (EZ ChIP™, Upstate Biotechnology; cat #17-371). Possible binding sites of ZNF304 in the ITGB1 promoter were predicted using an online tool (available on the world wide web at compbio.cs.princeton.edu/zf/). Six primer pair sets were designed using basic local alignment search tool software (National Center for Biotechnology Information). Primers used for amplification of the DNA in quantitative PCR are shown in Tables 3 and 4. Anti-ZNF304 antibody (Table 1) was used for the chromatin immunoprecipitation assays. The Bio-Rad DNA Engine Dyad® Thermal Cycler was used with the following cycling conditions: 2 min at 94° C., followed by 35 cycles of 30 sec at 94° C., 30 sec at 58° C., and 1 min at 68° C., followed by 1 min at 68° C.

TABLE 3

Oligonucleotide sequences for qRT-PCR

| Target Gene | Forward Sequence (5'→3') | Reverse Sequence (5'→3') |
| --- | --- | --- |
| ZNF304 Set 1 | GCACAGAGATTCCTGTACCGT (SEQ ID NO: 16) | TTTCAAGAGTGGGTCACACATC (SEQ ID NO: 17) |
| ZNF304 Set 2 | GTGTGACCCACTCTTGAAAGAC (SEQ ID NO: 18) | CCCTCTGAAGCAATTCTCTCCAT (SEQ ID NO: 19) |
| ZNF304 Set 3 | TGGAGGGGCCTCATTTGTG (SEQ ID NO: 20) | CTCCCTGCACGTAAAGGATCT (SEQ ID NO: 21) |
| ITGB1 Set 1 | CCTACTTCTGCACGATGTGATG (SEQ ID NO: 22) | CCTTTGCTACGGTTGGTTACATT (SEQ ID NO: 23) |
| ITGB1 Set 2 | GTAACCAACCGTAGCAAAGGA (SEQ ID NO: 24) | TCC CCTGATCTTAATCGCAAAAC (SEQ ID NO: 25) |
| ITGB1 Set 3 | CAAGAGAGCTGAAGACTATCCCA (SEQ ID NO: 26) | TGAAGTCCGAAGTAATCCTCCT (SEQ ID NO: 27) |
| Mutation Primer Set | GAACACCAGGGATCACACAGAA ACTGTGCACACG (SEQ ID NO: 28) | CGTGTGCACAGTTTCTGTGTGAT CCCTGGTGTTC (SEQ ID NO: 29) |

Abbreviations: ZNF304, zinc finger protein 304; ITGB1, integrin beta 1

TABLE 4

Oligonucleotide sequences for qPCR analysis of ChIP assays

| Gene | Amplicon Location | Forward Sequence (5'→3') | Reverse Sequence (5'→3') |
|---|---|---|---|
| ITGB1 | 3775-3725 | GGGTTGAGGAGAGGGA AGTA (SEQ ID NO: 30) | TGC CTTTCAGTTGCTGTCCT AA (SEQ ID NO: 31) |
| ITGB1 | 3392-3297 | AAGGCCAGCAGCATTG AAAG (SEQ ID NO: 32) | AGAACACAGAAGAGCTACA GGAC (SEQ ID NO: 33) |
| ITGB1 | 3155-3108 | TCTGTTTCTTGCCAGTGC CC (SEQ ID NO: 34) | CCTTCTGAAACCCTTGTGCC (SEQ ID NO: 35) |
| ITGB1 | 1989-1939 | TTTGCCTTGAGAAAGTC ACG (SEQ ID NO: 36) | TCCTGTAATCCCAGCTTCTCA (SEQ ID NO: 37) |
| ITGB1 | 1546-1496 | TGTGTGTGTATATGTGTG TCACCTT (SEQ ID NO: 38) | TGC GAGAAACCAACTGGTAG (SEQ ID NO: 39) |
| ITGB1 | 784-613 | TCC CAGGTTCAAGCAGTT CTC (SEQ ID NO: 40) | GCTCACGCCTGGAATCTCA (SEQ ID NO: 41) |

Abbreviations: ITGB1, integrin beta 1.

Plasmid construction and luciferase reporter assay. Fragments containing the predicted binding sites (BS1, BS2, and BS3) were amplified from HeyA8 cell genomic DNA by PCR using primers containing SacI or Hind/III restriction enzyme sites. The PCR products were purified, digested, and subsequently cloned into the same restriction site of the pGL3 control vector (Promega) downstream of the firefly luciferase reporter gene. Sequences were analyzed with a DNA BigDye® Terminator sequencing kit, version 3.1 (Life Technologies) HeyA8 cells were plated in 24-well plates (60,000 cells per well) 24 h prior to transfection with either ZNF304 siRNA or ZNF304-expressing vector (Promega). Twenty-four hours after the first transfection, cells were transfected with the luciferase reporter vectors containing BS1, BS2, or BS3 together with Renilla luciferase construct, which was used as a normalization reference. Transfections were performed with Attractene transfection reagent (Qiagen) according to the manufacturer's instructions. Cells were lysed 48 h after luciferase vector transfection, and activity was measured using a dual-luciferase reporter assay system (Promega) in the Veritas™ microplate luminometer (Turner BioSystems). Three independent experiments were performed in technical triplicates. Wild-type vectors for ZNF304 (gene ID: 57343) and ITGB1 (gene ID: 16412) were purchased from Promega (San Luis Obispo, Calif.). ZNF304 vector was used to generate mutant vector (7-bp deletion) by using the QuikChange™ Site-Directed Mutagenesis Kit (Agilent Technologies, Santa Clara, Calif.) using the primers in Table 3.

In vitro anoikis. Cells were transfected with control or ZNF304 siRNA and transferred to 6-well tissue culture plates that were coated with polyhydroxyethylmethacrylate, and cells were cultured in these plates for 72 h at 37° C. in a 5% $CO_2$ atmosphere. Cells were washed with PBS and were stained with Annexin V-FITC and PI solution (50 µg/ml) containing RNase A (25 µg/ml). After incubating the pellets for 30 min at 37° C., cell viability was analyzed by flow cytometry.

Preparation of DANP. DANPs were prepared via ionic gelation of anionic tripolyphosphate and siRNA. Briefly, predetermined tripolyphosphate (0.25% weight/volume) and siRNA (1 µg/µl) were added to chitosan solution, and the siRNA/chitosan nanoparticles spontaneously formed under constant stirring at room temperature. After incubating the nanoparticles at 4° C. for 40 min, the siRNA/DANP were collected by centrifugation (Heraus Biofuge Fresco) at 16,000 g for 40 min at 4° C. Chitosan nanoparticles were coated with polylactic acid polymer under probe sonication, and the organic solvent was evaporated. The pellet was washed in sterile water three times to isolate siRNA/DANP, which was stored at 4° C. until use. For the biodistribution study, DANPs were labeled with rhodamine 6G (Sigma-Aldrich). Rhodamine 6G (0.1% weight/volume) was added to the polymer solution (chloroform) in the simple emulsion. The particles were collected and were washed three times to eliminate any nonencapsulated marker.

Orthotopic in vivo models of ovarian carcinoma and tissue processing. Female athymic nude mice (NCr-nu) (8-12 wks old) were purchased from the National Cancer Institute-Frederick Cancer Research and Development Center (Frederick, Md.) and were maintained as previously described (Landen et al., 2005). Mice were cared for in accordance with guidelines set forth by the American Association for Accreditation of Laboratory Animal Care and the United States Public Health Service Policy on Human Care and Use of Laboratory Animals. To generate tumors, SKOV3IP1 cells ($1 \times 10^6$), HeyA8 cells ($2.5 \times 10^5$), or ($3 \times 10^6$) OVCA-432 cells were injected into the peritoneal cavity, as previously described (Lu et al., 2008). For therapy experiments, 10 mice (eight mice per group for OVCA-432 in vivo study) were assigned randomly to each group. This sample size was sufficient to provide 80% power for a test at significance level of 0.05. Treatments with control or ZNF304 siRNA incorporated in DANP were intravenously administered either weekly (150 µg/kg body weight) or biweekly (300 µg/kg body weight). Paclitaxel (100 µg/mouse for the HeyA8 model and 75 µg/mouse for the SKOV3 model) was injected intraperitoneally once weekly. Mice were euthanized 6 wks after first administration in SKOV3 model and 4 wks after first administration in HeyA8 model. After euthanasia, mouse and tumor weights, number of nodules, and distribution of tumors were recorded. Individuals who performed the necropsies were blinded to the treatment group assignments. Tissue specimens were fixed with either formalin or optimal cutting temperature medium (Miles) or were snap-frozen in liquid nitrogen. For OVCA-432 survival study, the treatment started one week after the tumor cell inoculation and the mice were monitored daily by three observers. Individual mice were euthanized on the day the core veterinarian recommended, based on moribund status.

For the biodistribution study of DANP, mice were injected peritoneally with HeyA8 cells ($2.5 \times 10^5$) for tumor inoculation. When tumors were detectable, rhodamine 6G-labeled particles that contained control siRNA (150 µg/kg) were administered intravenously. After 24 h, mice were euthanized; tumors and the major organs (brain, heart, kidney, spleen, liver, and lungs) were removed and fixed in optimal cutting temperature medium and sectioned. The organ and tumor distribution of particles were assessed by fluorescence microscopy.

In vivo anoikis. Viability of tumor cells from ascites fluid was determined by dual staining with PI and epithelial cell adhesion molecule tagged with fluorescein isothiocyanate. MDAH 2774 cells ($2 \times 10^6$) were injected intraperitoneally into nude mice, and treatments started when mice developed detectable ascites. Mice were divided into two groups (n=3/group), receiving a single administration of either DANP-control siRNA or DANP-ZNF304 siRNA (300 µg/kg). After seven days, ascites fluid was drawn from the peritoneal cavity and rapidly centrifuged at 500 g for 10 min. Pellets were washed with a red blood cell lysis buffer and reconstituted in PBS. Suspended cells were then incubated with excited state absorption-fluorescein isothiocyanate (1:30 dilution) for 30 min at room temperature. After incubation, cells were washed and stained with a PI solution (50 µg/ml). Cells were then incubated for 30 min at 37° C. and analyzed on a Gallios™ flow cytometer (Beckman Coulter).

Immunohistochemical analysis. Analyses of tumors cell proliferation and microvessel density were conducted by following procedures described previously (Lu et al., 2010; Landen et al., 2006; Langley et al., 2003). Two investigators quantified the number of positive cells in a blinded fashion. The antibodies used and the vendors are listed in Table 1.

Statistical analysis. Unless specified otherwise, all data are presented as the mean values±the standard error of the mean from at least three independent experiments. Two-sided t-tests were used to test the relationships between the means of data sets, and P values indicate the probability of the means compared, being equal with *P<0.05, P<0.01, and *P<0.001. Student's t-tests and analysis of variance were calculated with GraphPad software. Statistical analyses were performed in R (version 3.0.1) (available on the world wide web at r-project.org/), and P values less than 0.05 were considered statistically significant. For the analysis of RPPA results, the Benjamini-Hochberg multiple testing correction (Benjamini and Hochberg, 1995) was used to estimate the false discovery rate.

Example 1—ZNF304 in Human HGSOC

To identify new therapeutic targets and strategies, an integrative analysis of The Cancer Genome Atlas (TCGA) HGSOC dataset (Vaughan et al., 2011) and gene profiles of ovarian and breast tumors was carried out to identify genes that are important for cancer metastasis. Since N-cadherin has been reported to play a critical role in invasion and anoikis resistance of cancer cells (Suyama et al., 2002; Abdul Azis, 2013), gene signatures were identified for tumors with high N-cadherin expression in the TCGA HGSOC dataset. Of 16,869 genes that were upregulated in ovarian carcinoma, 493 genes had a positive correlation with tumoral N-cadherin expression (FIG. 1A). Of these 493 genes, ciliary neurotrophic factor receptor (CNTFR); melanoma antigen family D, 1 (MAGED1); nuclear receptor subfamily 2, group F, member 2 (NR2F2); and ZNF304 were upregulated in invasive ovarian and breast tumor epithelium compared with normal ovarian (Bowen et al., 2009) and breast epithelium (Casey et al., 2009), respectively.

Figure 1B:
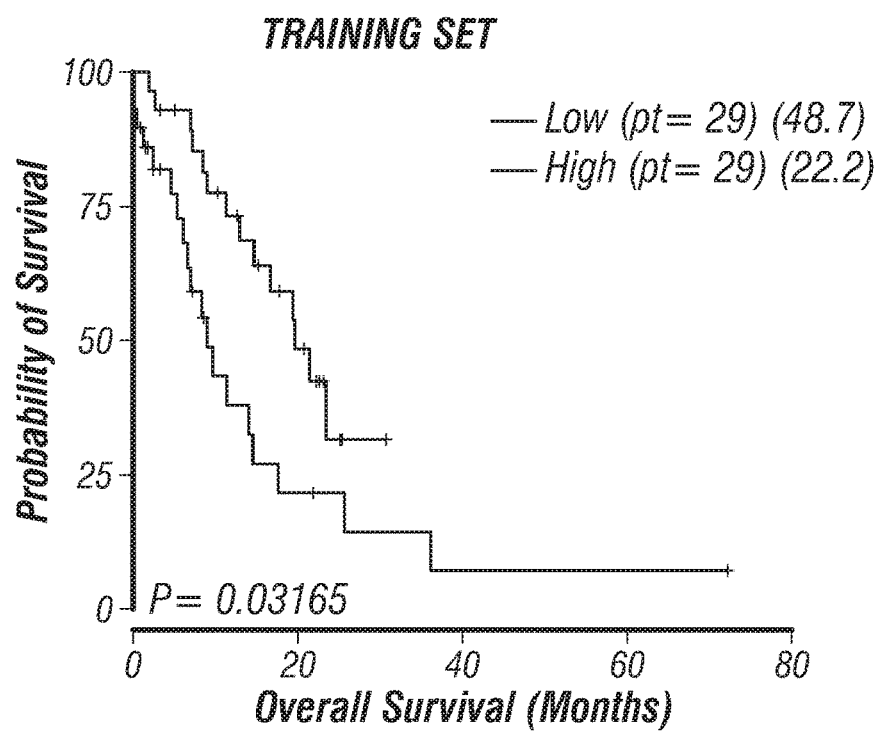
Figure 1C:
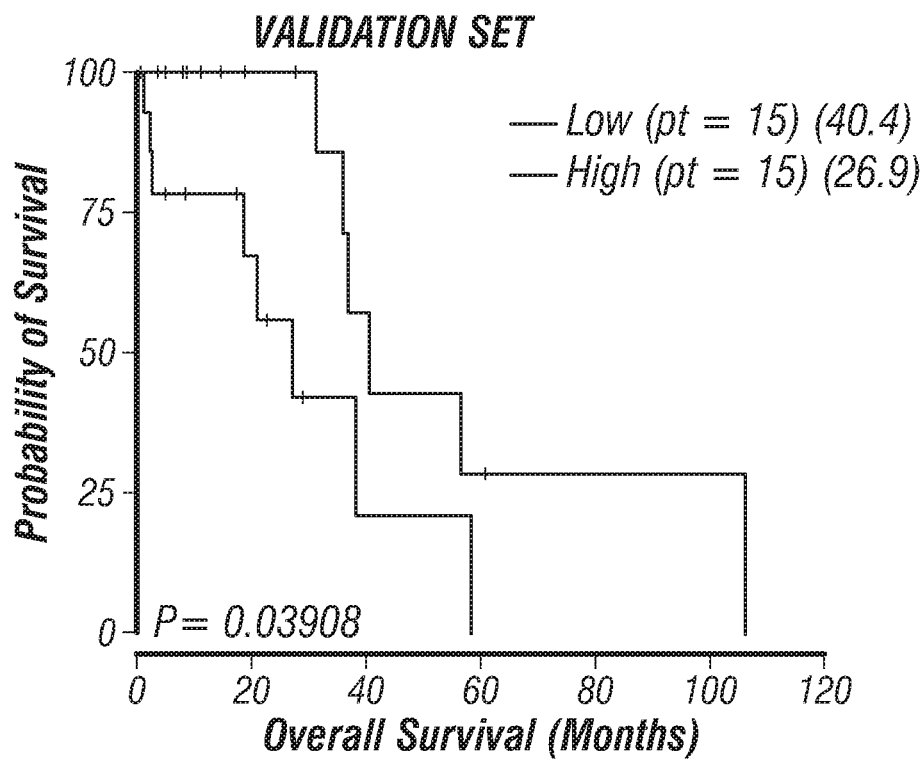
Figure 9A:
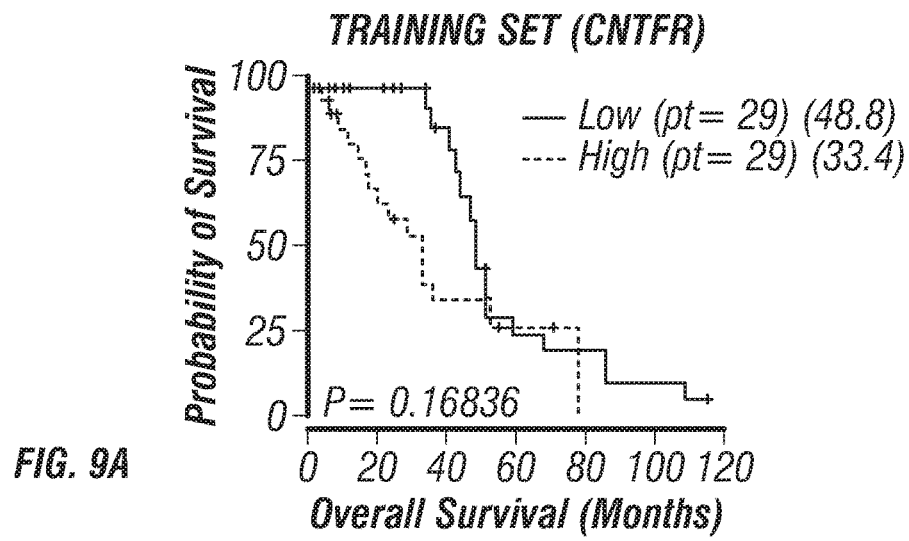
FIGS. 9A-F. Probability of survival in ovarian carcinoma patients based on candidate targets Kaplan Meier curves for ovarian carcinoma patients based on CNTFR expression in (A) Training set (at the 40 month time point, the top line is "low" and the bottom line is "high") and (B) Validation set (at 20 month time point, the top line is "low" and the bottom line is "high"); MAGED1 expression in (C) Training set (at the 30 month time point, the top line is "low" and the bottom line is "high") and (D) Validation set (at the 60 month time point, the top line is "high" and the bottom line is "low"); NR2F2 expression in (E) Training set (at the 80 month time point, the top line is "low" and the bottom line is "high") and (F) Validation set (at the 50 month time point, the top line is "high" and the bottom line is "low"). Expression levels for any of the three potential targets were not correlated with patient survival (Log-rank Test).
Figure 9B:
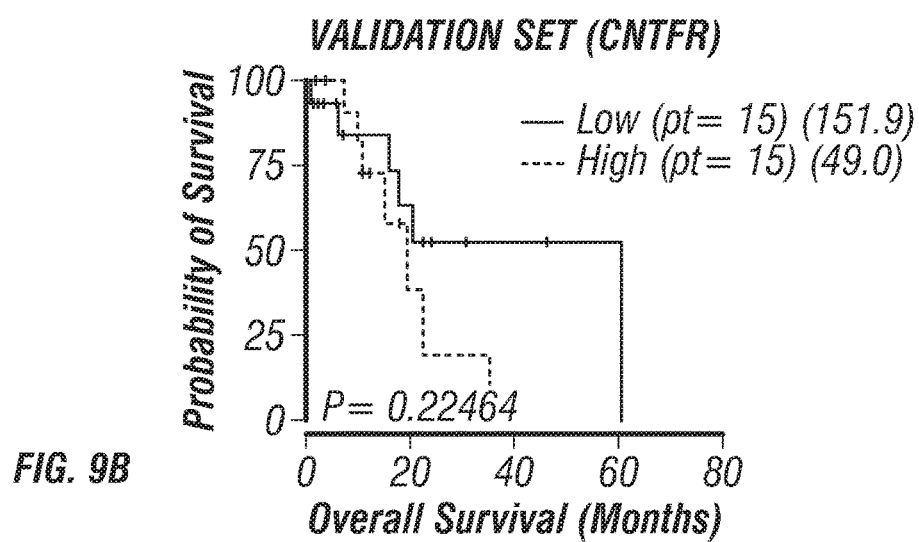
Figure 9C:
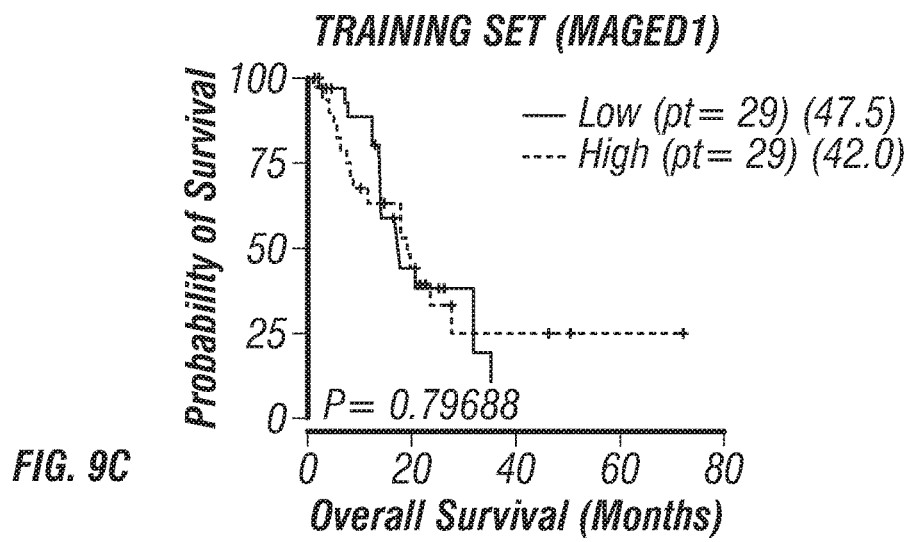
Figure 9D:
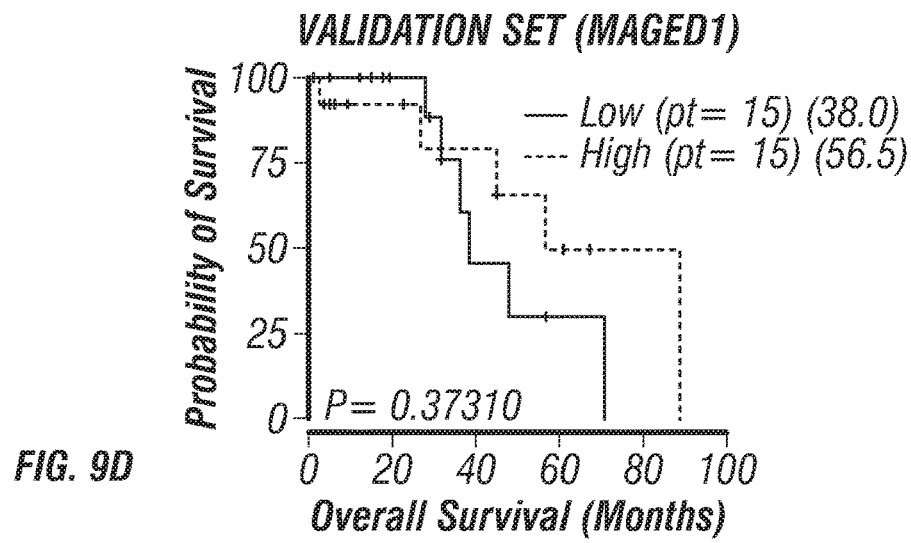
Figure 9E:
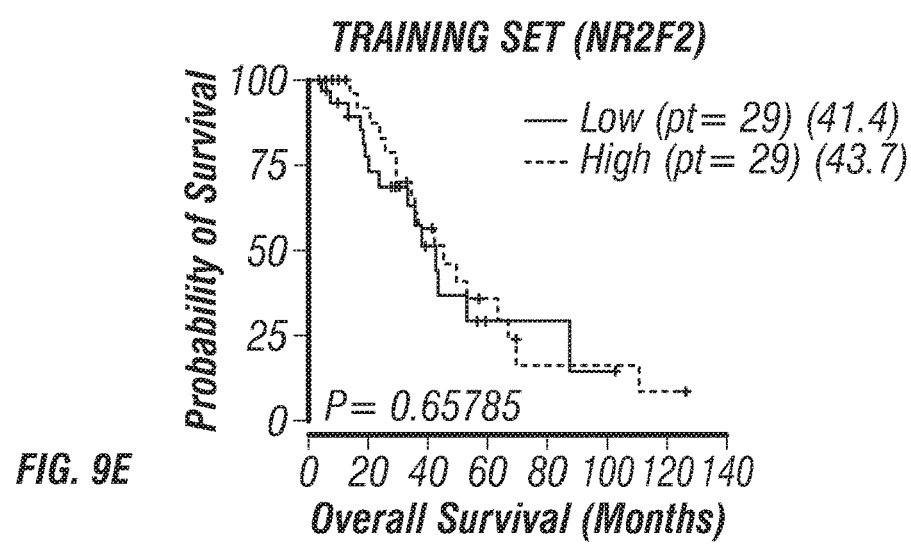
Figure 9F:
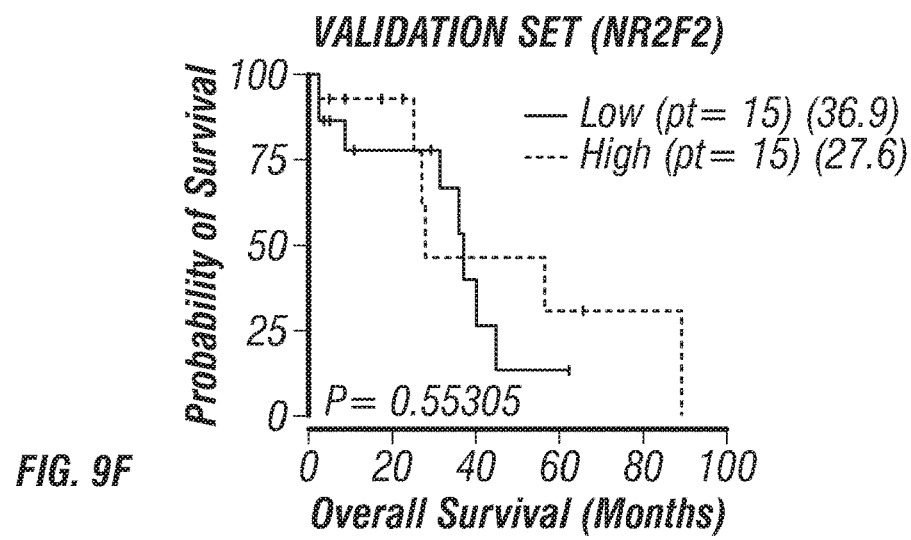

The effect of tumoral expression on patient survival was assessed for these four genes using the TCGA HGSOC dataset (FIGS. 9A-F). For each gene, the entire ovarian carcinoma patient population was randomly split into training (2/3 of cases) and validation cohorts (1/3 of cases). In both cohorts, patients were divided into sextiles according to mRNA expression, and the first and last sextiles were contrasted. Importantly, the relationships between overall survival and known prognostic factors, such as age or residual disease, were examined in both the training and the validation cohorts using a Cox proportional hazards model. Only ZNF304 was a significant factor in this analysis (FIGS. 1B and 1C). In contrast, CNTFR (Training and validation sets; FIGS. 9A and 9B, respectively), MAGED1 (Training and validation sets; FIGS. 9C and 9D, respectively), and NR2F2 (Training and validation sets; FIGS. 9E and 9F, respectively) expression levels were not correlated with patient survival. Patients with high tumoral ZNF304 expression had significantly lower median overall survival than patients with low tumoral ZNF304 expression (FIG. 1B [training set, 22.2 versus 48.7 months, P=0.031, Log-rank test]; and FIG. 1C [validation set, 40.4 versus 26.9 months, P=0.039, Log rank test]). Based on these results, ZNF304 was selected for additional studies.

Figure 1D:
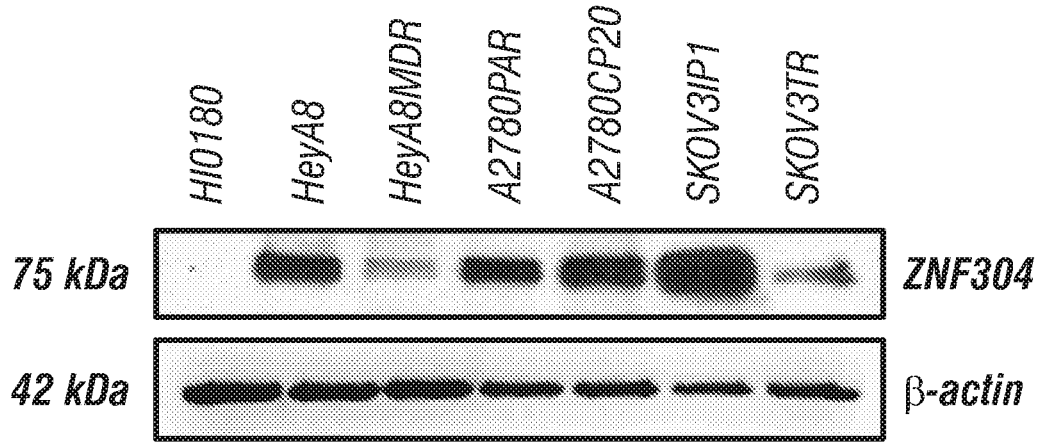
Figure 1E:
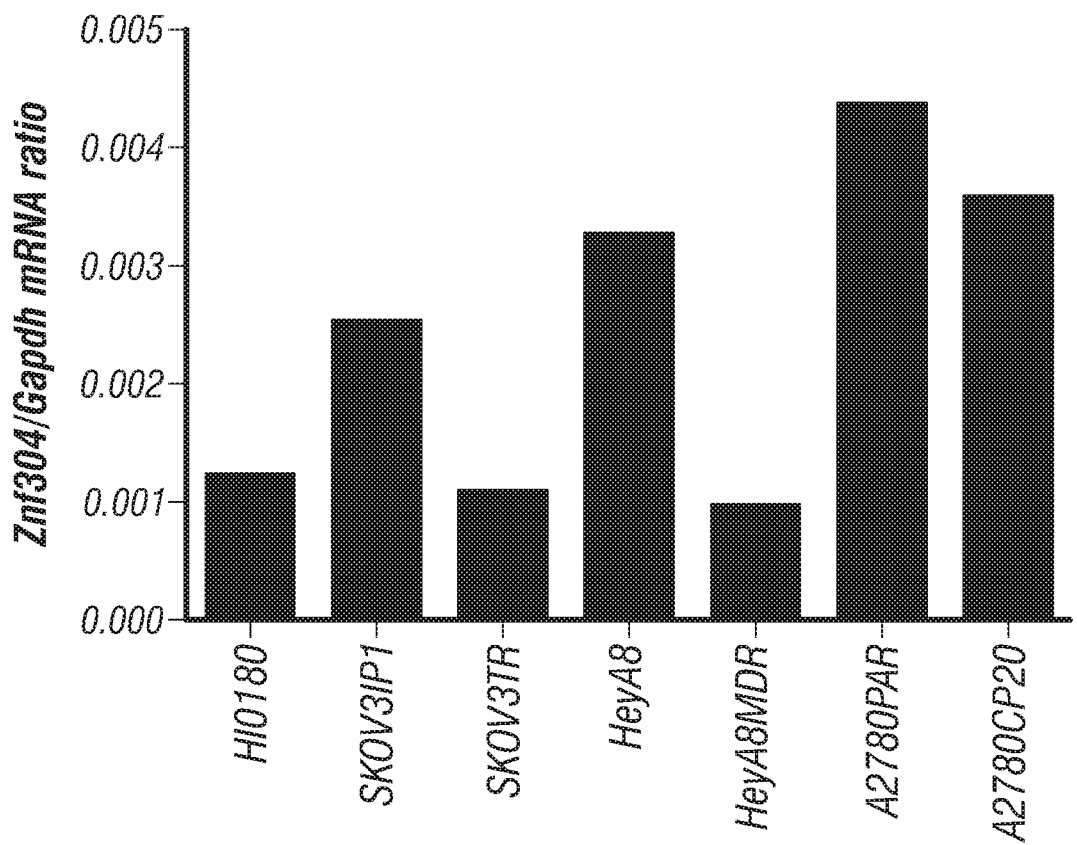
Figure 10:
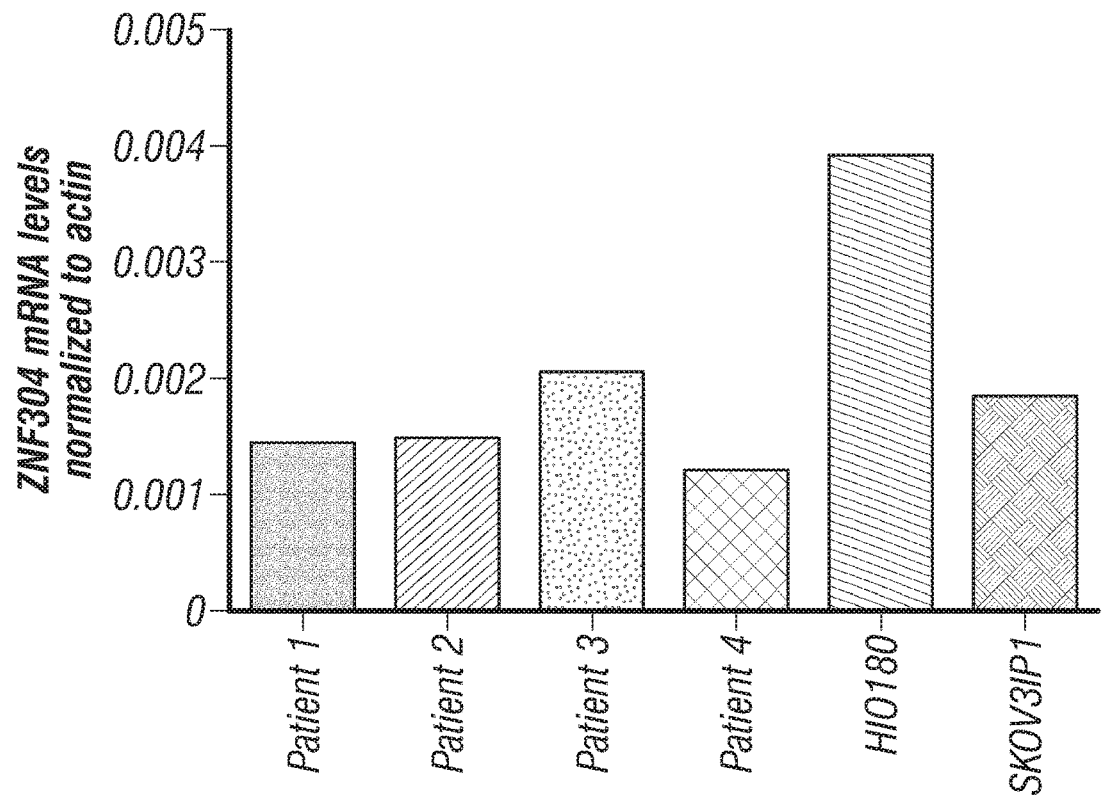
FIG. 10. ZNF304 mRNA levels in ovarian carcinoma patient samples and cell lines ZNF304 mRNA levels were determined and compared in four patient samples, in HIO180 non-transformed ovarian cell line, and SKOV3 cancer cell line by Real Time RT-PCR (Ratios were analyzed by comparing $2^{-(delta\ CT)}$ values of ZNF304 mRNA).

Next, protein expression levels of ZNF304 (75 kDa) were examined by Western blot analysis in six ovarian carcinoma tumor cell lines and in HIO180 non-transformed ovarian epithelial cells (FIG. 1D). ZNF304 protein was highly expressed in all ovarian carcinoma cells tested, but a lower expression was observed in the HIO180 cells. ZNF304 mRNA basal levels were high in four of the six ovarian carcinoma cell lines (FIG. 1E). Additionally, ZNF304 mRNA levels were analyzed in patient normal distal fallopian tubes versus HIO180 and SKOV3IP1 cancer cells (FIG. 10). ZNF304 mRNA levels were similar between fallopian tube and HIO180; however, ZNF304 levels were significantly higher in SKOV3IP1 cells.

Example 2—Silencing ZNF304 Inhibits Migration and Proliferation in Ovarian Carcinoma Cells ZNF304 is a transcription factor that belongs to the C2H2 zinc finger family. The member genes of this family represent the largest class of transcription factors in humans and, indeed, one of the largest gene families in mammals (Tadepally et al., 2008). ZNF304 can be unregulated by activated Kirsten rat sarcoma viral oncogene homolog (KRAS) in KRAS-positive colorectal cancer cells and binds at the promoters of INK4-ARF and other CpG island methylator phenotype genes in colorectal cancer cells and in human embryonic stem cells (Serra et al., 2014).

Figure 2A:
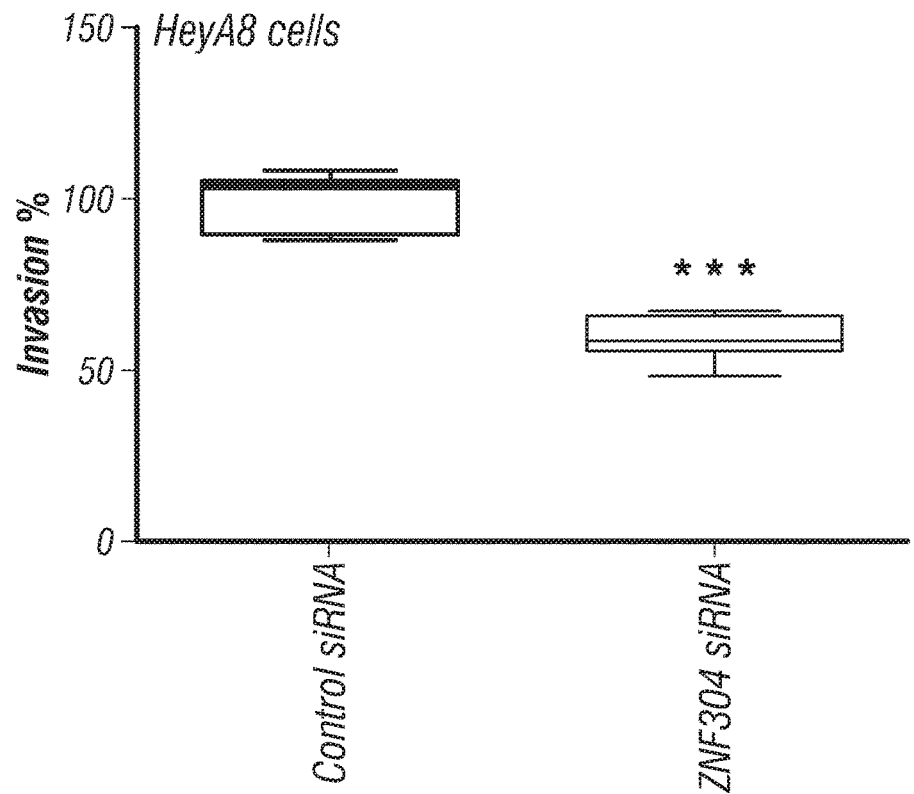
FIGS. 2A-J. Silencing ZNF304 inhibits migration and proliferation. (A-C) The effect of ZNF304 silencing on Invasion % (A), migration % (B) of HeyA8 cells, and migration % of SKOV3IP1 cells (C). Migration and invasion percentages in ZNF304 siRNA treated samples were calculated after normalization with control siRNA treated samples. Box-and-whisker plots showing median (horizontal line), interquartile range (box), and maximum/minimum range (whiskers). All images shown are representative and data are presented as mean±s.e.m. of n≥3 experimental groups. *P≥0.05, P≥0.01, and *P≥0.001 (Student's t-test). (D) Western blot analysis of ZNF304, p-Src (Y416) and total src levels 72 h post transfection with all ZNF304 siRNA sequences in HeyA8 cells. (E) Levels of focal adhesion kinase phosphorylation (Y397) after ZNF304 downregulation by all ZNF304 siRNA sequences in HeyA8 cells. (F) Immunoblotting results of β1 integrin and p-paxillin (Y31) and p-paxillin (Y118) after 72 h of ZNF304 siRNA treatment in HeyA8 cells. (G-J) Cell-cycle arrest analysis of HeyA8 cells (G), SKOV3IP1 cells (H), A2780PAR cells (I), and A2780P20 cells (J) after 72 h transfection with ZNF304 siRNA. Cells were harvested at 72 h and were fixed, stained with propidium iodide, and analyzed by fluorescence-activated cell sorting. Data are presented as the percentage of cells as mean±s.e.m.of n≥3 experimental groups. *P≥0.05, P≥0.01, *P≥0.001 (Student's t-test).
Figure 2B:
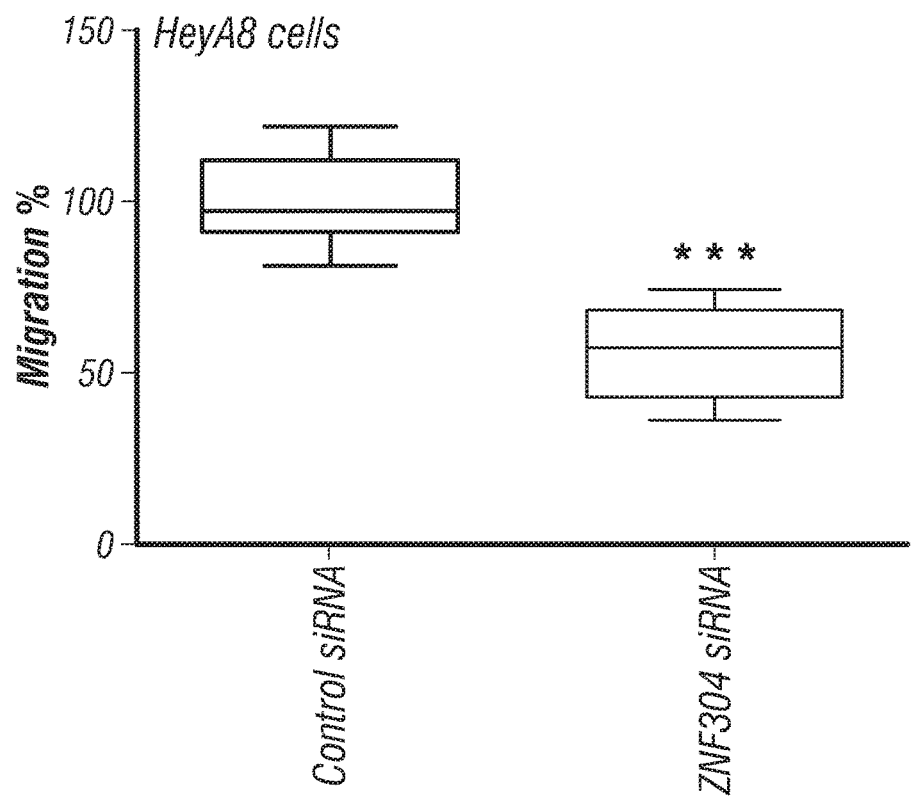
Figure 2C:
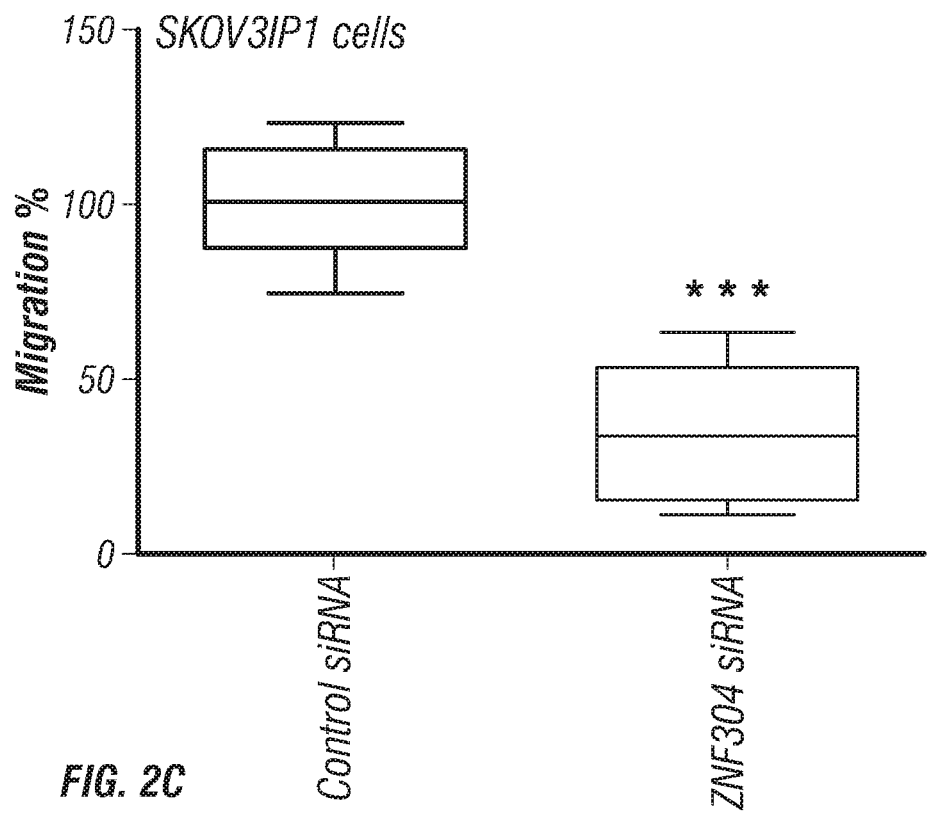
Figure 11:
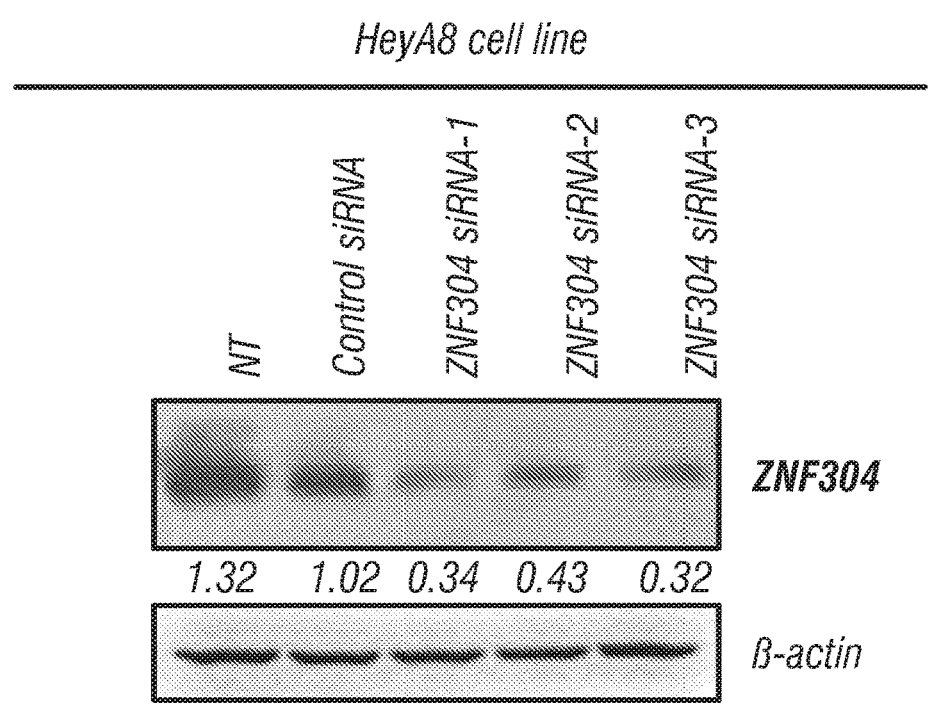
FIG. 11. ZNF304 protein levels in Control siRNA and ZNF304 siRNA sequences treated HeyA8 cells Western Blot analysis of ZNF304 protein expression 72 h after Control siRNA or three different ZNF304 siRNA sequences tested in HeyA8 cells.

Since ZNF304 was found to be the most highly associated with overall survival in HGSOC patients, whether silencing ZNF304 would affect invasion and migration was investigated. The knockdown efficiency of three siRNA sequences targeting ZNF304 were first tested in HeyA8 cells (FIG. 11). Two of the three siRNA sequences tested (ZNF304 siRNA-1 and ZNF304 siRNA-3) showed more than 65% inhibition of ZNF304 in HeyA8 cells. Therefore, these two siRNA sequences were selected for further studies. Next, invasion and migration assays were performed in HeyA8 and SKOV3IP1 cell lines with the selected siRNA sequences, resulting in 40% inhibition of invasion and 45% inhibition of migration in HeyA8 cells (FIGS. 2A and 2B, respectively) and 27% inhibition of migration in SKOV3IP1 cells (FIG. 2C).

Figure 2D:
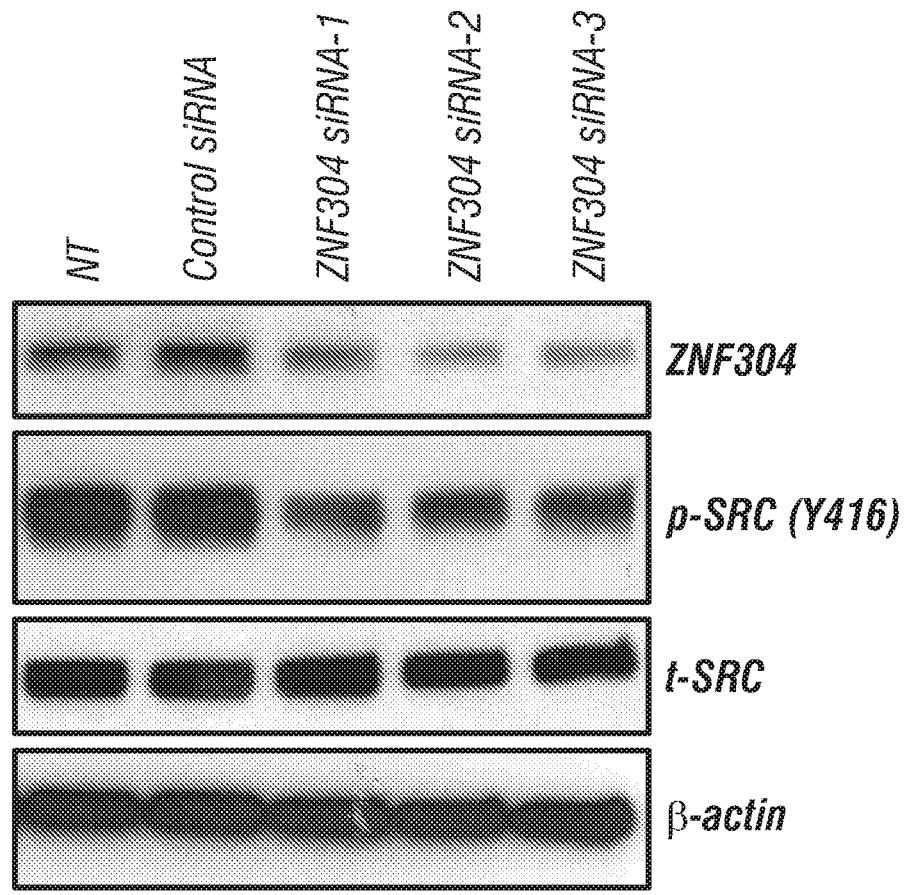
Figure 2E:
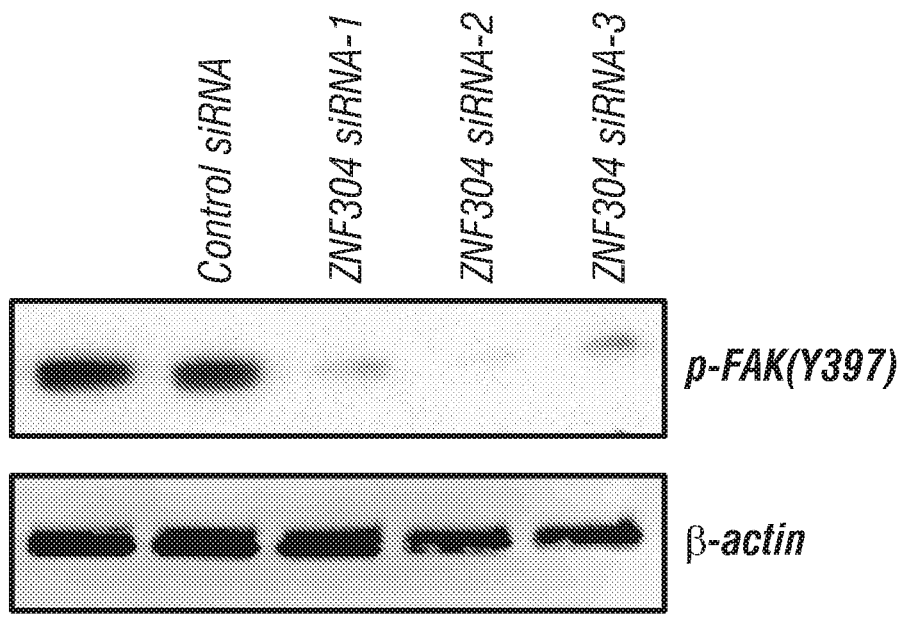
Figure 2F:
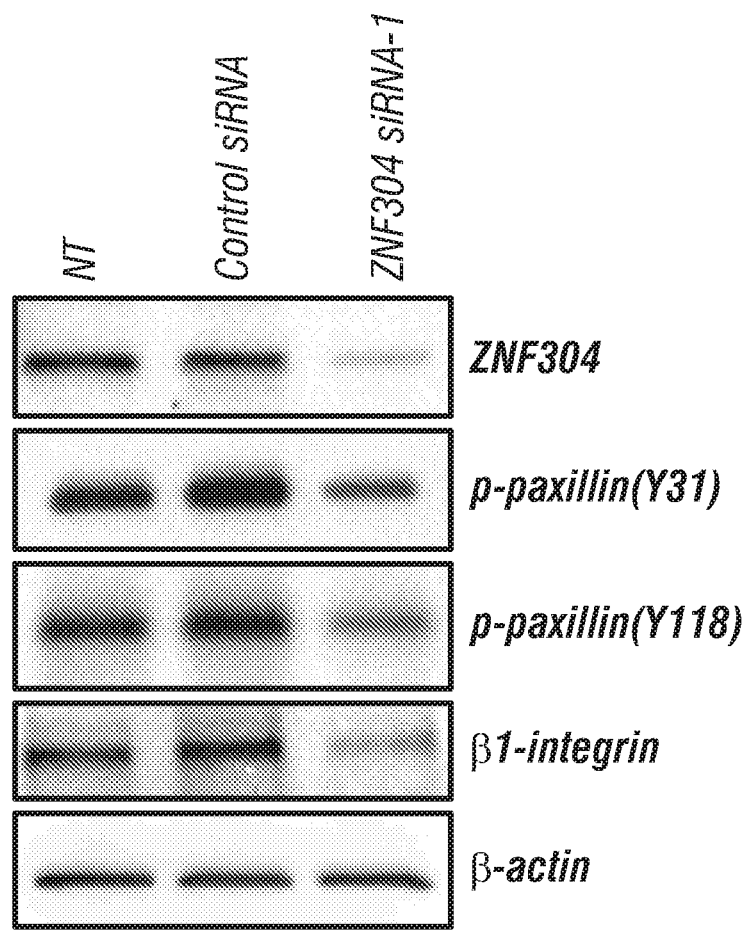
Figure 2G:
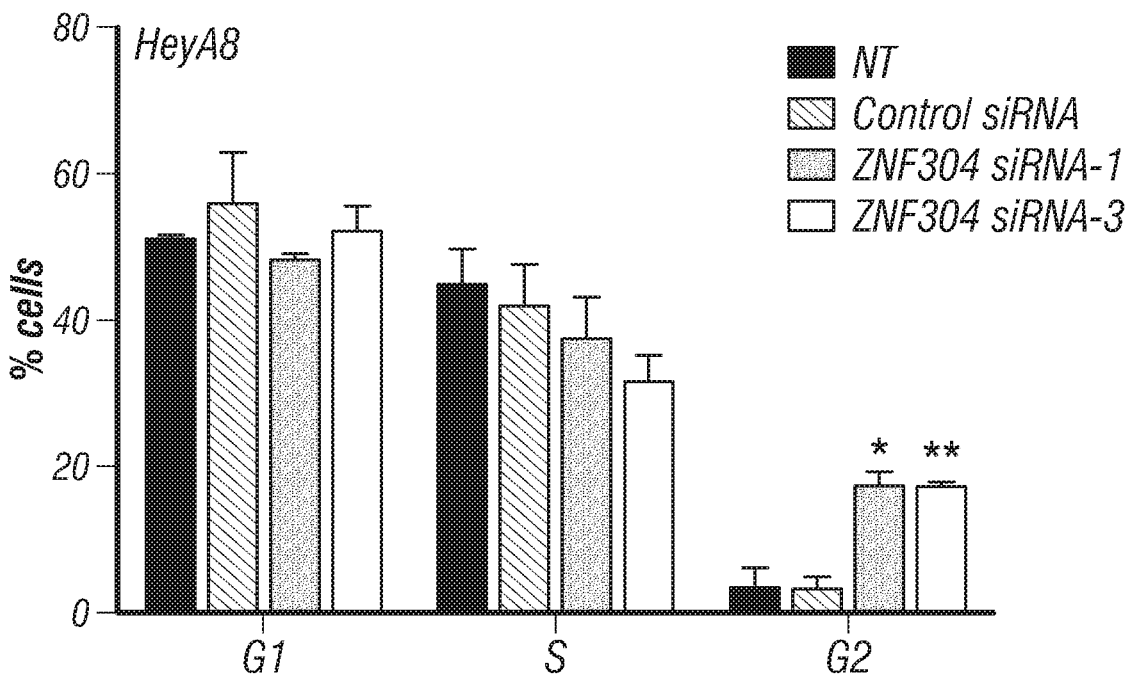
Figure 2H:
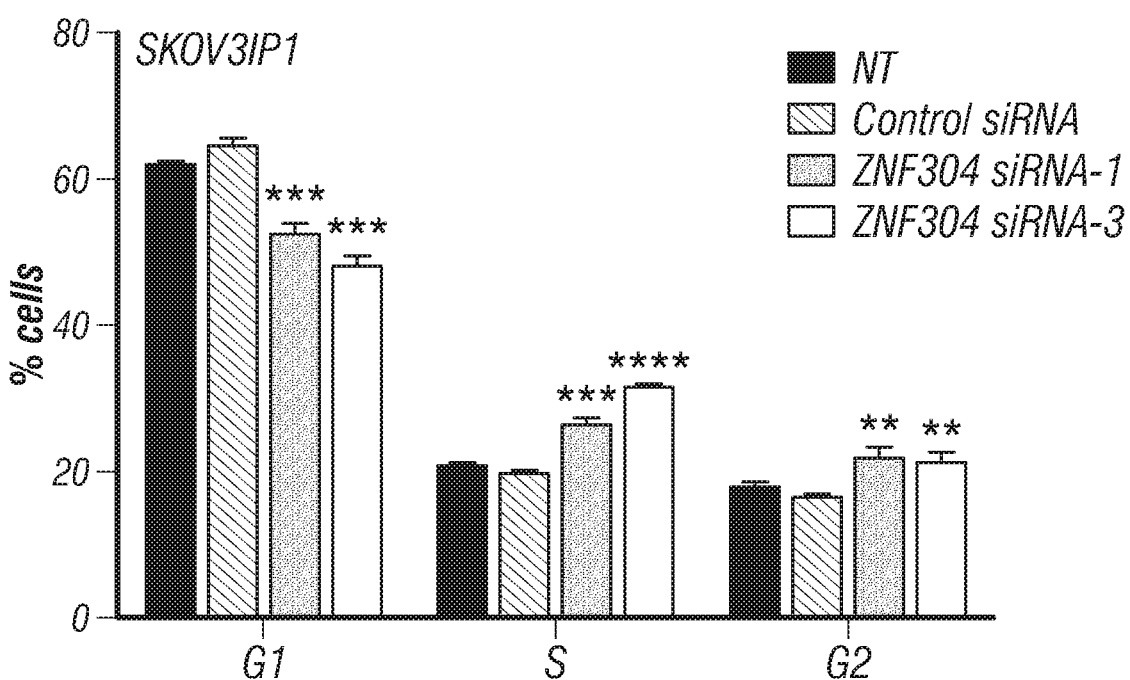
Figure 2I:
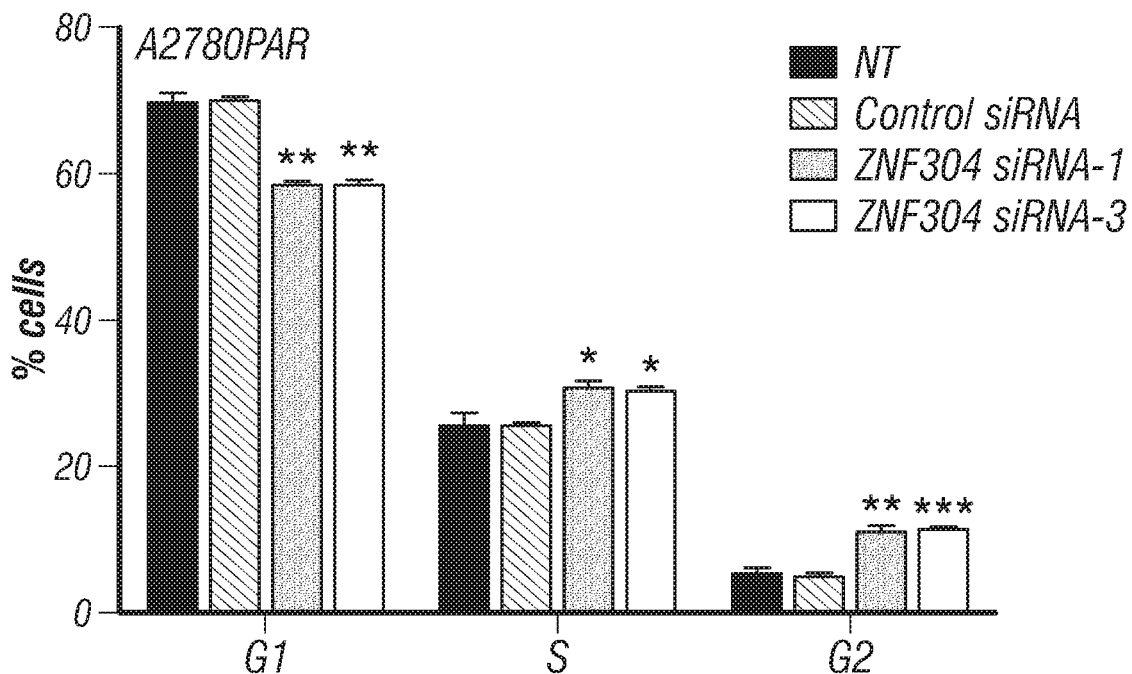
Figure 2J:
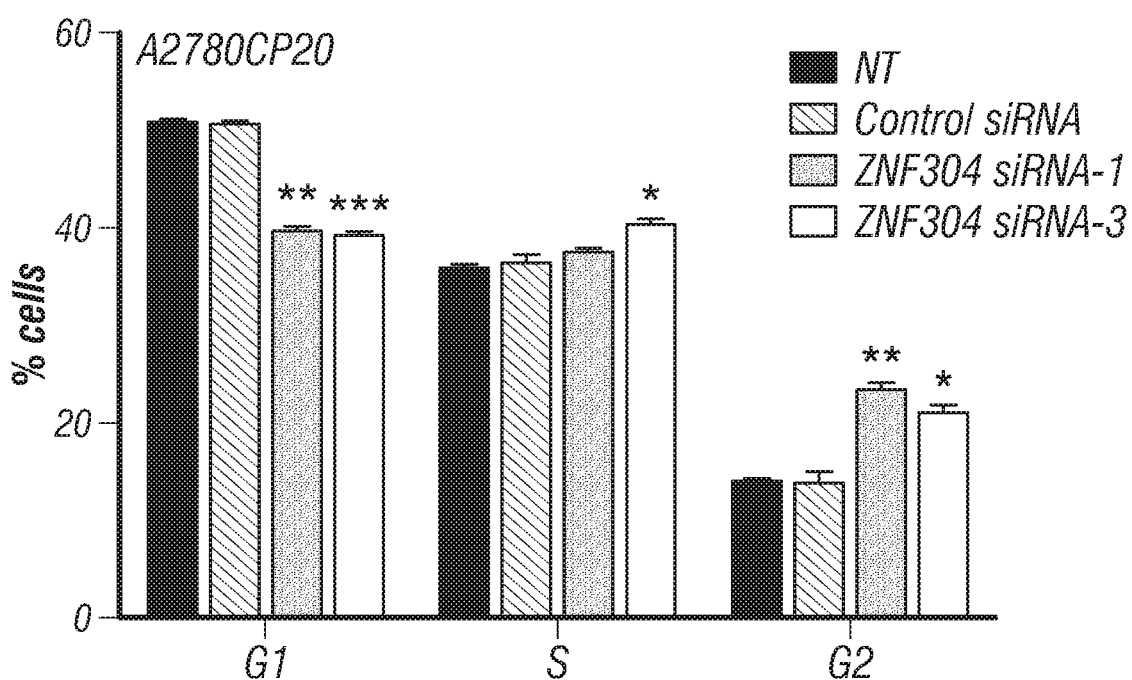

To determine the potential signaling pathways in which ZNF304 is involved, a reverse phase protein array (RPPA) analysis of control siRNA-treated and ZNF304 siRNA-treated HeyA8 cells was performed. Samples were probed with 214 validated antibodies to total proteins and their respective phospho-proteins. Silencing ZNF304 led to reduced expression of caveolin-1, fibronectin, MYH9 (myosin II), and the effectors of the Ras signaling pathway (BRAF, RAF1). This prompted further analysis of the link between ZNF304 and integrin signaling (Table 5). ZNF304 mRNA expression was highly correlated with β1 integrin expression in HGSOC samples (r=0.20, P=0.0015; Spearman's rank-order correlation test).

migration and invasion, the effects of ZNF304 silencing on paxillin and β1 integrin were investigated (FIG. 2F). ZNF304 silencing inhibited both paxillin phosphorylation at tyrosine sites 31 and 118 and β1 integrin expression in the cell lines tested.

In the RPPA results, forkhead box M1 (FOXM1) and cyclin B1 levels were also decreased in ZNF304-silenced samples, suggesting that ZNF304 might play a role in the cell cycle. To determine the effects of ZNF304 silencing on proliferation, cell-cycle analysis was performed in HeyA8, SKOV3IP1, A2780PAR, and A2780CP20 cell lines after 72 h of ZNF304 siRNA transfection (FIGS. 2G-2J, respectively). All cell lines treated with ZNF304 siRNA showed significant arrest in the G2 phase, confirming the decreases in cyclin B1 and FOXM1 levels found in the RPPA analysis.

TABLE 5

Reverse phase protein array analysis of zinc finger protein 304 (ZNF304)-silenced HeyA8 cells. The ErbB, FAK, and integrin signaling pathways were significantly deregulated in ZNF304-silenced HeyA8 cells. Integrated function and pathway analysis were performed using DAVID bioinformatics resources (on the world wide web at david.abcc.ncifcrf.gov/), and significant features were clustered. The p-value and false discovery rate presented in the table are generated by a modified Fisher Exact test. Details on DAVID Functional Annotation Tool are given on the world wide web at david.abcc.ncifcrfgov/helps/functional_annotation.html#fisher

| Database | Pathway | Count | Genes | P value | FDR |
|---|---|---|---|---|---|
| KEGG | ErbB signaling | 9 | EIF4EBP1, CDKN1B, BRAF, ERBB3, PAK4, STAT5A, RAF1, MAPK8, RPS6KB1 | 1.85E−08 | 1.93E−05 |
| KEGG | Focal adhesion | 7 | CAV1, BRAF, PAK4, MET, RAF1, ITGA2, MAPK8, FN1 | 9.72E−04 | 1.0069 |
| KEGG | Insulin signaling | 7 | EIF4EBP1, BRAF, TSC2, RAF1, MAPK8, RPS6KB1, RPS6 | 8.41E−05 | 0.0875 |
| PANTHER | PDGF signaling | 7 | BRAF, STAT5A, RAB11B, RAF1, RAB11A, MAPK8, RPS6KB1 | 0.0026 | 2.3630 |
| PANTHER | Integrin signaling | 6 | CAV1, BRAF, RAF1, ITGA2, MAPK8, FN1 | 0.0275 | 22.5233 |
| KEGG | Actin cytoskeleton | 6 | BRAF, PAK4, RAF1, ITGA2, MYH9, FN1 | 0.0069 | 6.9846 |
| PANTHER | Interleukin signaling | 6 | CDKN1B, BRAF, FOXM1, STAT5A, RAF1, FOXO3 | 0.0238 | 19.8068 |
| REACTOME | Insulin receptor signaling | 6 | EIF4EBP1, TSC2, EEF2K, RAF1, RPS6KB1, RPS6 | 4.80E−07 | 3.76E−04 |
| KEGG | p53 signaling | 6 | CCNB1, BID, CCNE1, TSC2, CASP8, TP53, CHEK1 | 1.42E−05 | 0.0148 |
| KEGG | Cell cycle | 6 | CCNB1, CCNE1, CDKN1B, SMAD4, TP53, CHEK1, RB1 | 4.35E−04 | 0.4514 |
| REACTOME | Signaling by NGF | 6 | NRAS, CDKN1B, BRAF, TSC2, RAF1, MAPK8, FOXO3 | 0.0025 | 1.9945 |

Abbreviations:
ErbB, erythroblastic leukemia viral oncogene homolog;
FAK, focal adhesion kinase;
FDR, false discovery rate;
KEGG, Kyoto Encyclopedia of Genes and Genomes;
PANTHER, protein analysis through evolutionary relationships;
PDGF, platelet-derived growth factor;
NGF, nerve growth factor.

Figure 3A:
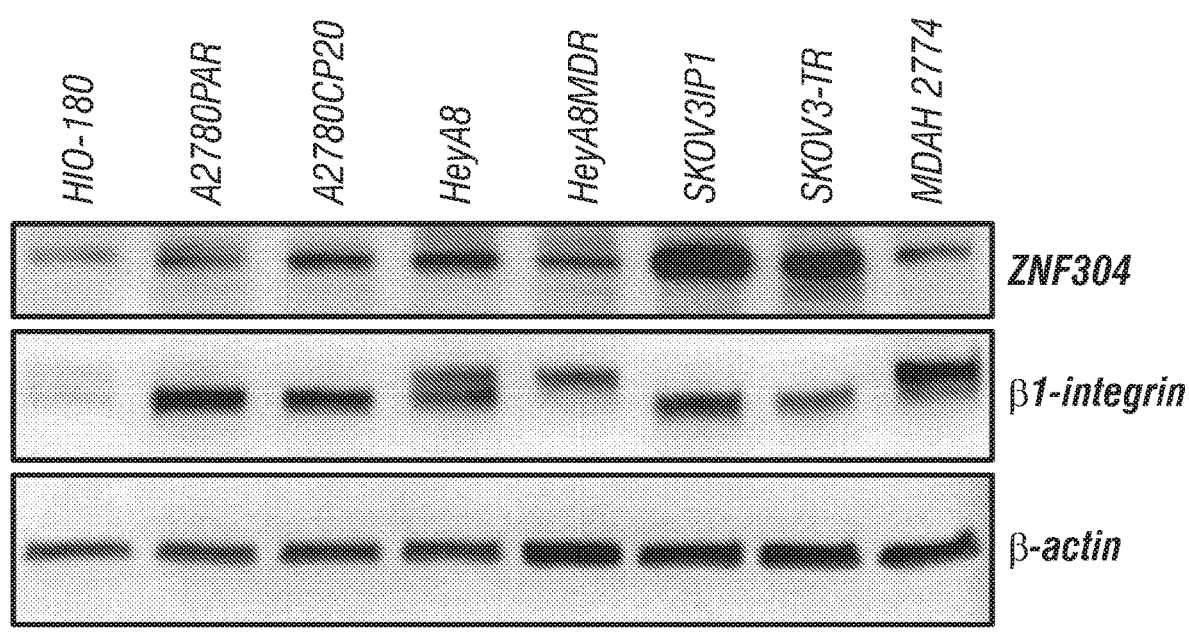
Figure 12A:
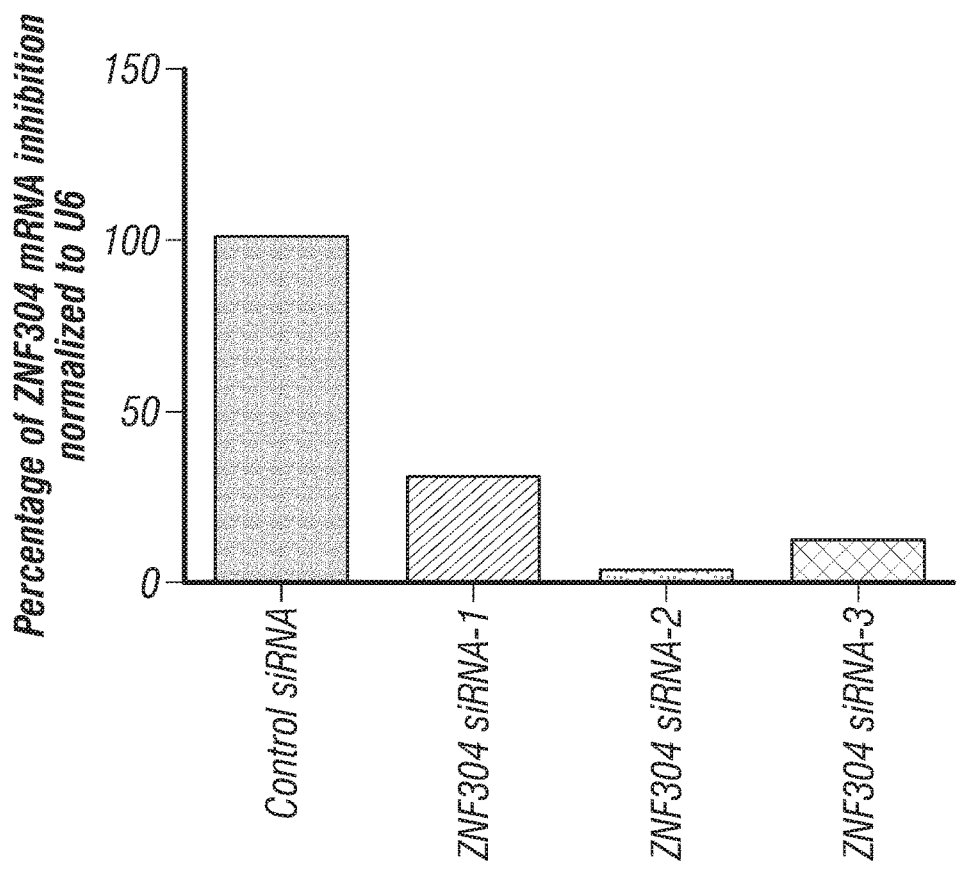
FIGS. 12A-C. ZNF304 and ITGB1 mRNA inhibition after ZNF304 silencing. (A) ZNF304 mRNA levels were determined by Real Time RT-PCR (Ratios were analyzed by comparing $2^{-(delta\ CT)}$ values of ZNF304 mRNA, (B) ITGB1 mRNA levels were determined by Real Time RT-PCR after silencing ZNF304 using ZNF304 siRNA-1 and (C) ZNF304 siRNA-3.
Figure 12B:
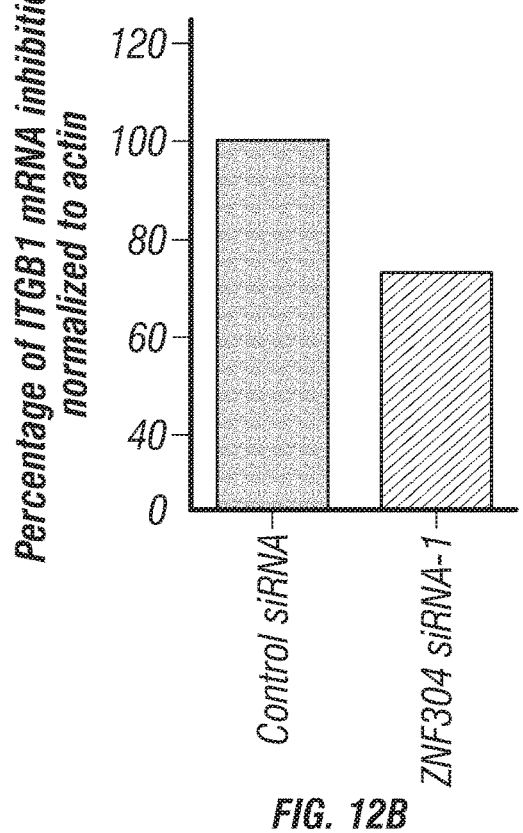
Figure 12C:
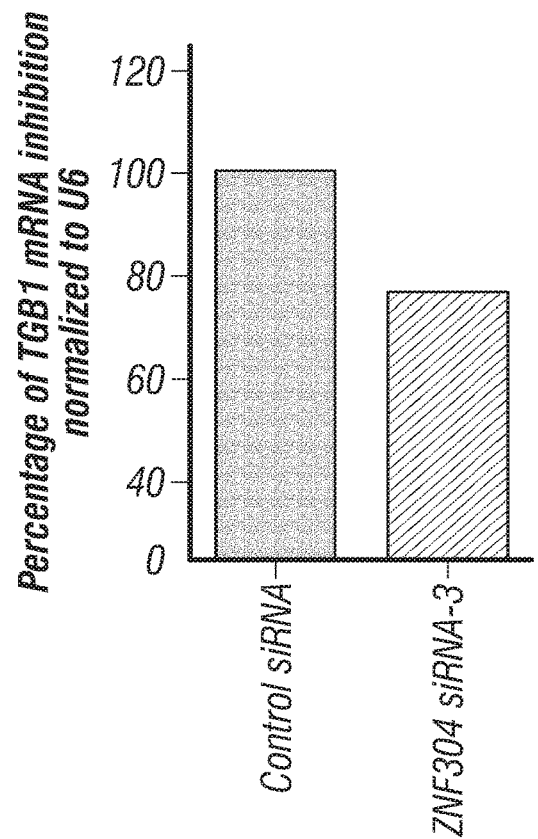

To further understand the role of ZNF304, the RPPA data were validated and the levels of focal adhesion complex members were determined after ZNF304 siRNA transfection in HeyA8 cells. Silencing ZNF304 decreased phosphorylation of Src and FAK, which are adaptor proteins of focal adhesion and major markers of cell migration (FIGS. 2D and 2E, respectively). To further analyze pathways related to Example 3—ZNF304 Transcriptionally Regulates β1 Integrin The ZNF304 gene is located at chromosome 19q13.43 (on the world wide web at genome.ucsc.edu). The ZNF304 protein (SEQ ID NO: 1) consists of a Kruppel-associated box domain (amino acids 14-88 of SEQ ID NO: 1) and 16 zinc fingers (amino acids 100-110; 128-136; 262-272; 290-300; 318-328; 346-356; 374-384; 402-412; 430-440; 458-468; 486-496; 514-524; 542-552; 570-580; 598-608; and 626-636 of SEQ ID NO: 1). To explore the mechanism by which ZNF304 silencing downregulates migration, protein and mRNA levels of β1 integrin were determined in HeyA8 and SKOV3IP1 cells following ZNF304 siRNA treatment. First, RT-PCR and real time RT-PCR were performed to determine the effects of the selected ZNF304 siRNA sequences on ZNF304 mRNA levels; the results showed the downregulation of ZNF304 mRNA in these cells (FIGS. 12A and 12B, respectively). Reduced β1 integrin mRNA levels were also detected after ZNF304 silencing using real time RT-PCR (FIGS. 12C-12D). The basal protein levels of β1 integrin were determined and it was found to be expressed in the cell lines tested (FIG. 3A).

Figure 3D:
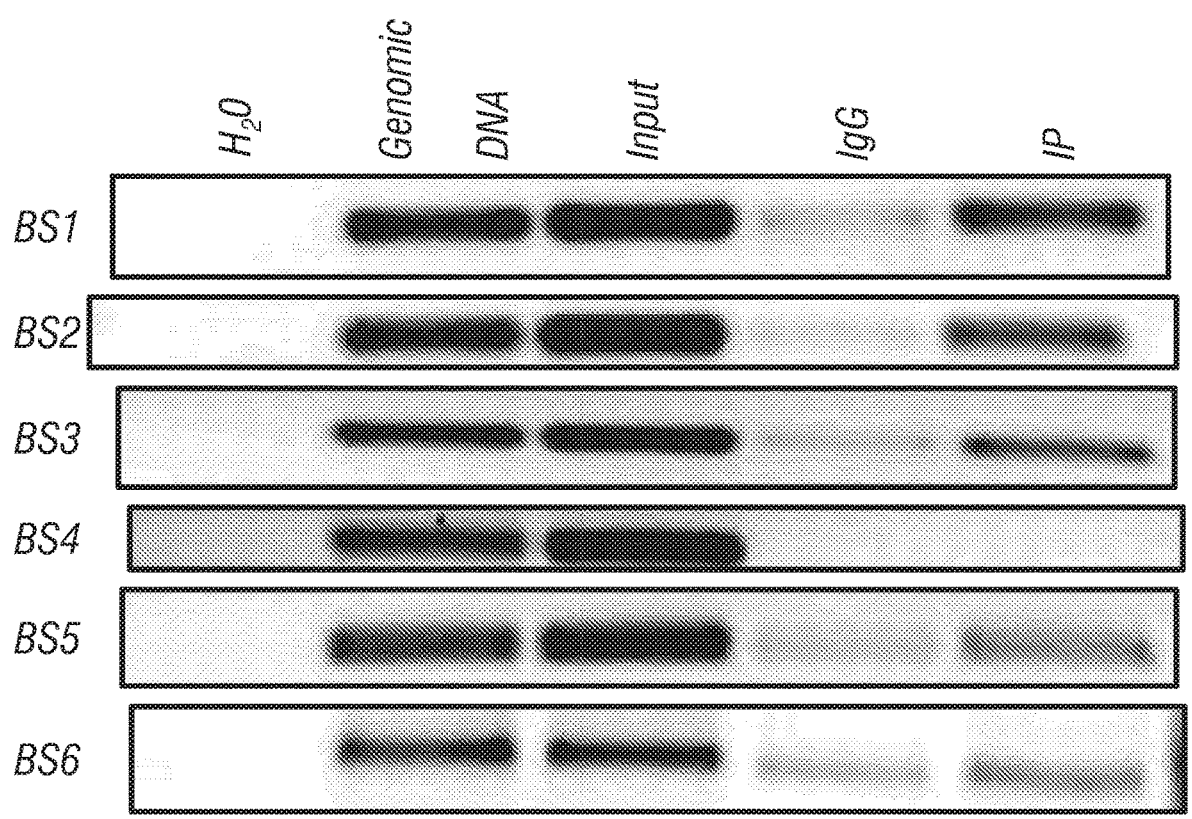
Figure 3E:
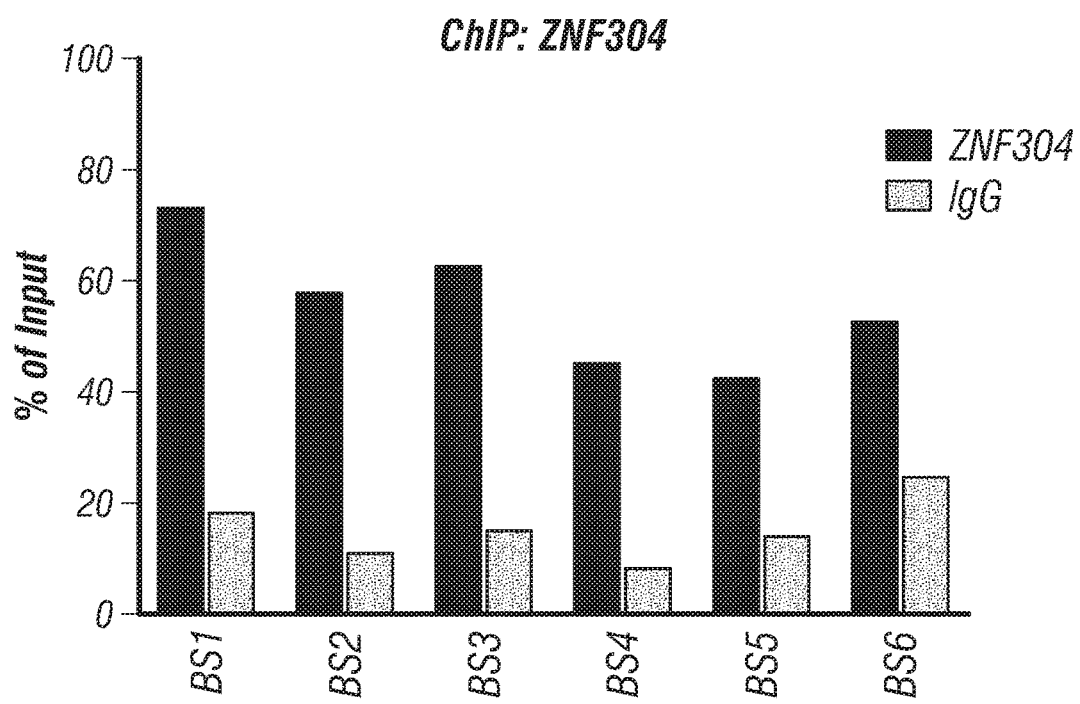

Next, it was investigated whether ZNF304 transcriptionally regulates β1 integrin. ZNF304-DNA binding sites were predicted on the basis of support vector machines (Persikov and Osada, 2009). Ten possible ZNF304 binding sites (SEQ ID NOs: 2-11) were identified in the β1 integrin promoter using support vector machine scores that ranged from 24.25 to 18.9 (scores were calculated using an online tool available on the world wide web at compbio.cs.princeton.edu/zf/). The transcription start site was predicted by the ensemble and was compared with the β1 integrin transcript sequence and the binding locations in the β1 integrin promoter region (FIG. 3B). Six primer sets containing the segments for the 10 binding sites were designed (FIG. 3C). DNA segments were amplified, cloned, sequenced, and confirmed with a standard nucleotide-nucleotide basic local alignment search tool (National Center for Biotechnology Information). To determine whether ZNF304 binds to the β1 integrin promoter, chromatin immunoprecipitation assays (ChIP) were performed in HeyA8 cells with ZNF304 antibody. Subsequent polymerase chain reaction (PCR) results confirmed the interaction of 131 integrin promoter and five of the six predicted ZNF304 binding sites (BS1, BS2, BS3, BSS, and BS6) (FIG. 3D). A densitometric analysis of the inputs and immunoprecipitation results for each binding site revealed that BS1, BS2, and BS3 had an affinity of >50% (FIG. 3E). Owing to their affinity, BS1, BS2, and BS3 were selected for further studies.

Figure 3F:
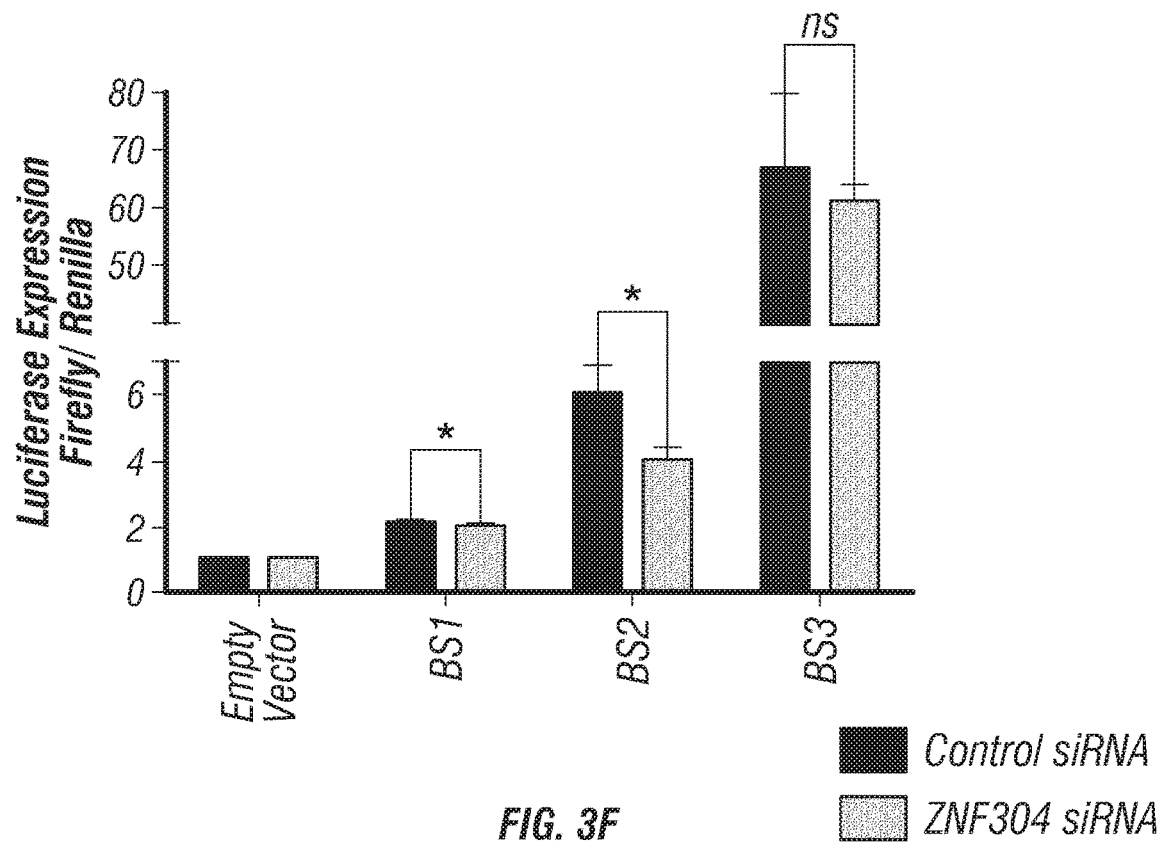
Figure 3G:
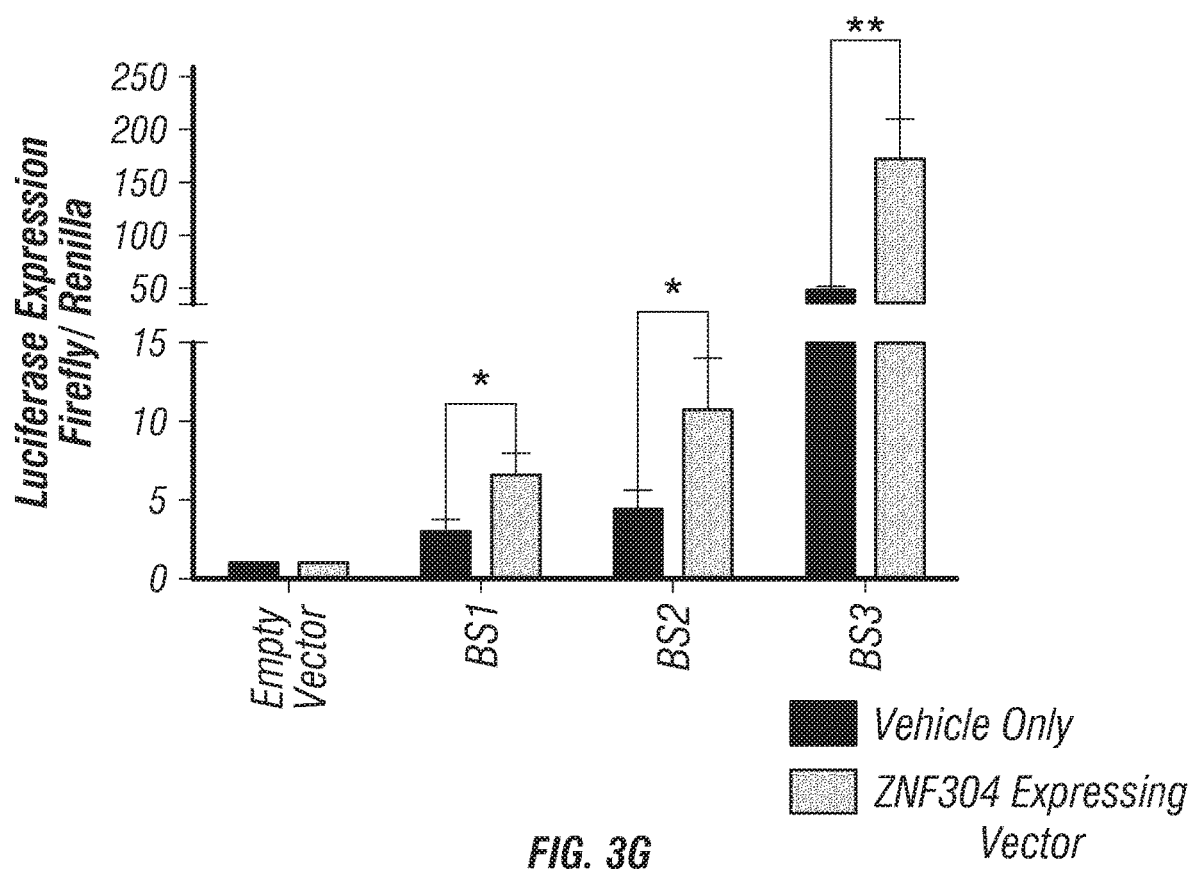

To identify the role of ZNF304 in the regulation of β1 integrin gene transcription, three constructs were developed that each contained one of the binding sites, which were inserted into the pGL3-basic vector. HeyA8 cells were transfected with the constructs, and the activity of each binding site was determined by a dual-luciferase reporter assay in cells with basal ZNF304 expression and in cells in which ZNF304 had been knocked down by siRNA. As shown in FIG. 3F, overall luciferase activity increased in cells transfected with the binding site constructs compared with cells transfected with the empty vector. Cells transfected with BS1-vector had twice as much luciferase expression as empty vector cells, whereas BS2-vector—transfected cells had 6-times more luciferase expression than did the empty vector cells. Cells transfected with BS3-vector showed the highest luciferase activity (approximately 70-times more expression than empty vector cells). ZNF304 silencing led to a decrease in luciferase activity in all three binding sites. The most significant was BS2-transfected cells, which had a 40.3% inhibition of luciferase activity (P=0.02; FIG. 3F). A 13.8% decrease in luciferase activity was found for cells transfected with BS1-vector and a 7.8% decrease was found for cells transfected with BS3-vector, compared with control cells (P=0.0173 and P=0.2630, respectively). Co-transfection of ZNF304-expressing vector significantly induced the luciferase activity of BS1-, BS2-, and BS3-vector-transfected cells (FIG. 3G). These results indicate that ZNF304 is a positive regulator of the active β1 integrin promoter and that ZNF304 increases its transcription by binding to BS2.

Figure 4A:
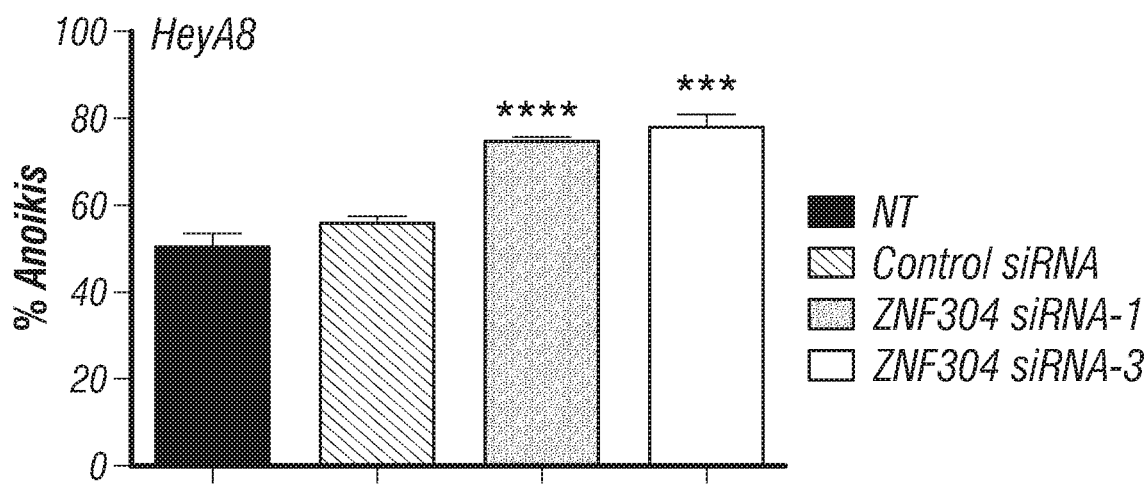
FIGS. 4A-C. ZNF304 mediated inside-out signaling. (A) The anoikis rates of HeyA8 cells at 72 hours post transfection in suspension condition. HeyA8 cells were transfected with indicated siRNAs, and incubated in anoikis plates for 72 h; cells were analysed by flow cytometry following Annexin V-FITC and propidium iodide (PI) staining. Data are presented as mean±s.e.m. of n≥3 experimental groups. *P≥0.05, P≥0.01,*P≥0.001, **P≥0.0001 (Student's t-test). (B) Immunoblotting analysis of HeyA8 cells in suspension conditions at 72 h after treatment with control siRNA or ZNF304 siRNA; followed by protein isolation and immunoblotting. Data are presented as mean±s.e.m. of n≥3 experimental groups. P≥0.01,*P≥0.001, **P≥0.0001 (Student's t-test). Poly ADP ribose polymerase cleavage indicates enhanced anoikis in ZNF304 siRNA-treated and control siRNA-treated samples in suspension conditions. (C) The anoikis rates of HeyA8 and SKOV3IP1 cells in suspension after ZNF304 silencing and β1 integrin overexpression. Cells were analysed by flow cytometry following Annexin V-FITC and PI staining. Data are presented as mean±s.e.m. of n>3 experimental groups. *P≥0.05, P≥0.01,*P≥0.001 (Student's t-test). NS, not significant.
Figure 4B:
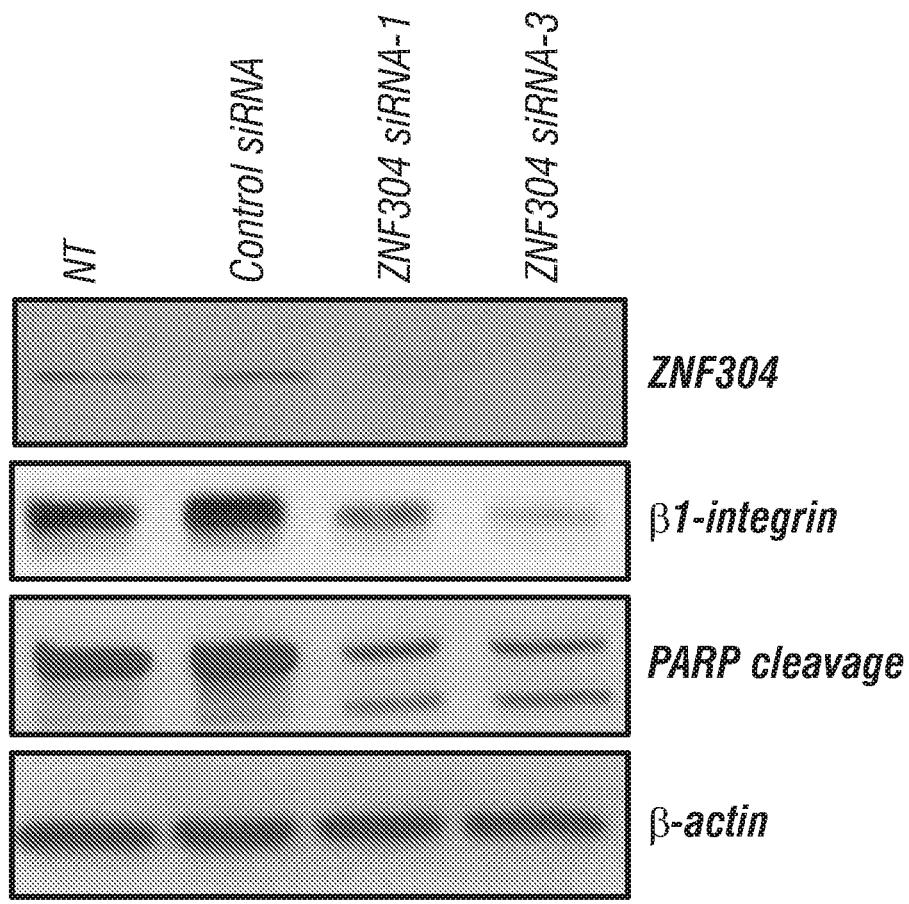
Figure 13:
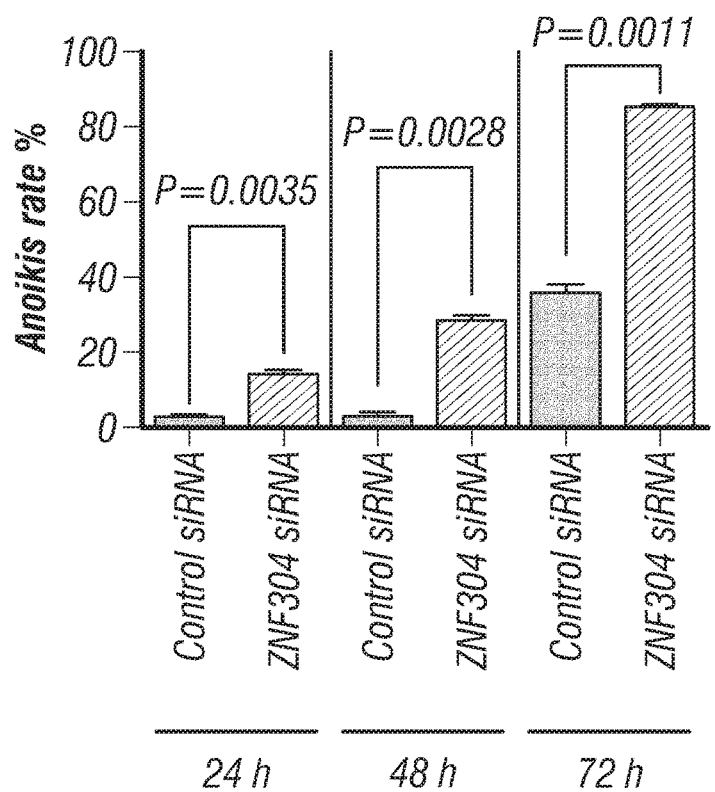
FIG. 13. Anoikis rates in HeyA8 cells at 24, 48, and 72 hours. % Anoikis rates in HeyA8 cells at 24 h (P=0.0035), 48 h (P=0.0028), and 72 h (P=0.0011) after ZNF304 silencing. Data are presented as the percentage of cells as mean±s.e.m. of n>3 experimental groups (Student's t-test).

Example 4—ZNF304 Protects Tumor Cells from Anoikis

β1 integrin confers a survival advantage to tumor cells (Vachon, 2011). As a regulator of β1 integrin, ZNF304 also inhibits anoikis through β1 integrin downregulation. Therefore, the anoikis rates were examined at 24, 48, and 72 h in detached HeyA8 cells in vitro using polyhydroxyethylmethacrylate (poly-HEMA)-coated tissue culture plates that promote anchorage-independent cell growth (Sood et al., 2010). The anoikis rates in ZNF304 siRNA-transfected cells were significantly higher than control siRNA-transfected cells at each time point tested (at 24, 48, and 72 h) (FIG. 13). The highest anoikis rate and induction of PARP cleavage were observed at 72 h; therefore all subsequent experiments were conducted at this time point. Cells transfected with the ZNF304 siRNAs for 72 h had a significantly higher ([ZNF304 siRNA-1, P<0.0001]; [ZNF304 siRNA-3, P<0.0005]) rate of anoikis (75%-80%) than control untreated or control siRNA-treated cells (60%) (FIG. 4A). Consistent with these results, immunoblotting from these samples showed that silencing ZNF304 also increased poly ADP ribose polymerase (PARP) cleavage (FIG. 4B), which supports the observation of increased anoikis in cells transfected with ZNF304 siRNA.

Figure 4C:
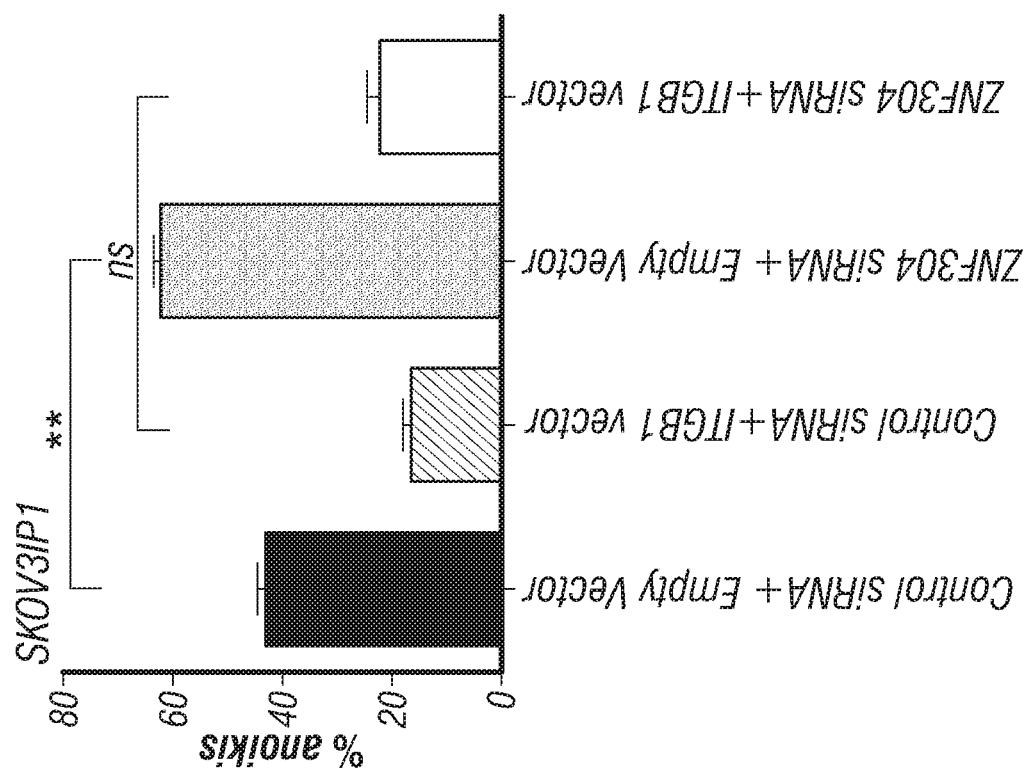
Figure 4C:
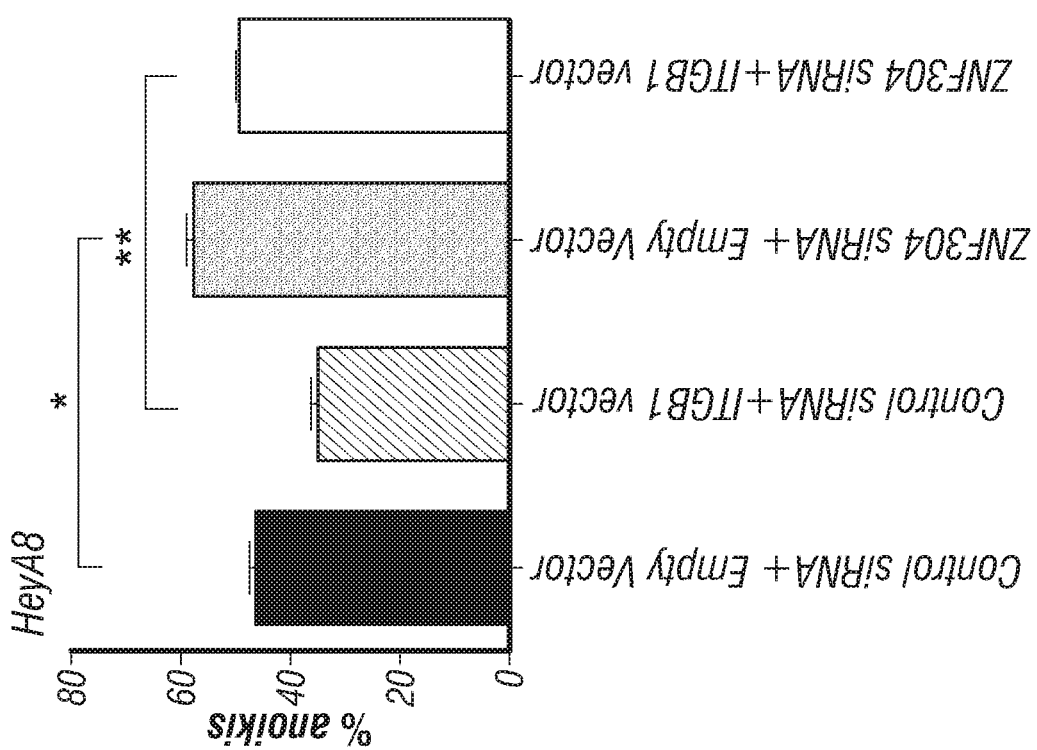
Figure 14:
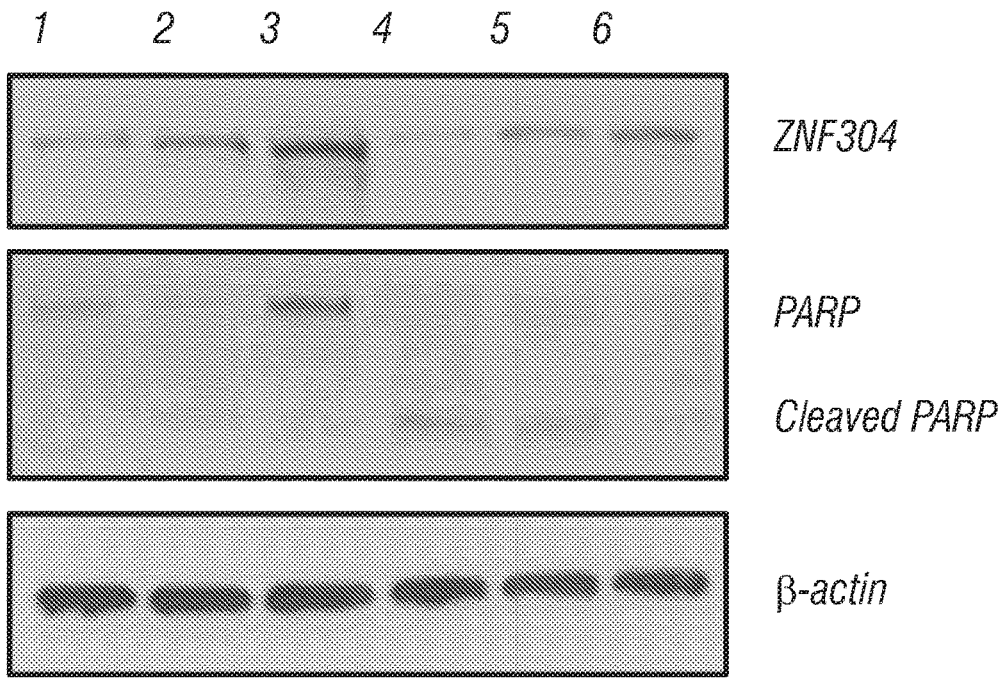
FIG. 14. ZNF304 overexpression rescues HeyA8 cells from anoikis. Western Blot analysis of ZNF304 protein expression and Poly ADP ribose polymerase cleavage (PARP) cleavage at 72 h post transfection in suspension condition. HeyA8 cells were transfected with relevant siRNA and vectors, and incubated in anoikis plates for 72 h; followed by protein isolation and immunoblotting.
Figure 15A:
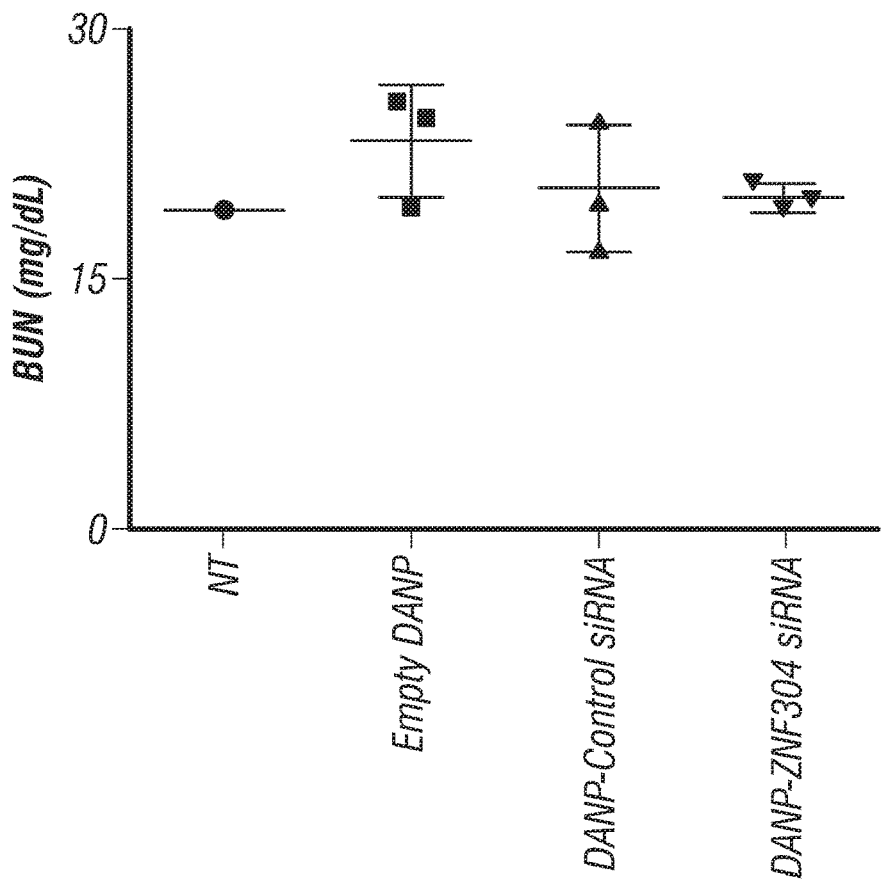
FIGS. 15A-D. DANP-siRNA treatment results in no abnormality in kidney and liver functions. (A) BUN, (B) Creatinine, (C) ALT and (D) Alkaline phosphatase levels remain in normal range at 72 h in blood after a single DANP-ZNF304 siRNA intravenous administration.
Figure 15B:
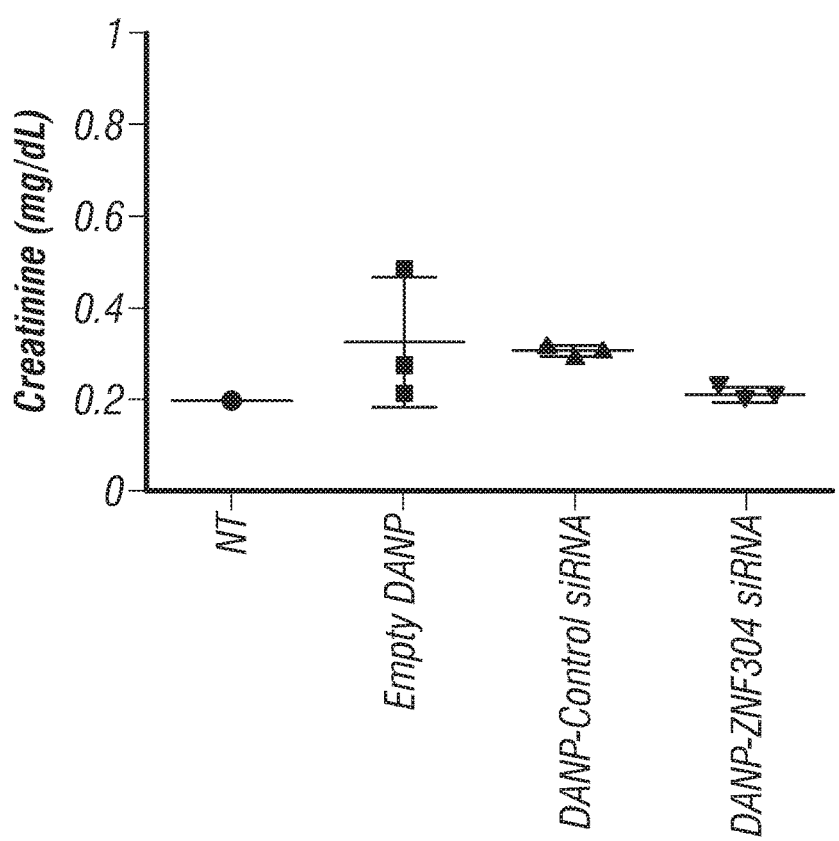
Figure 15C:
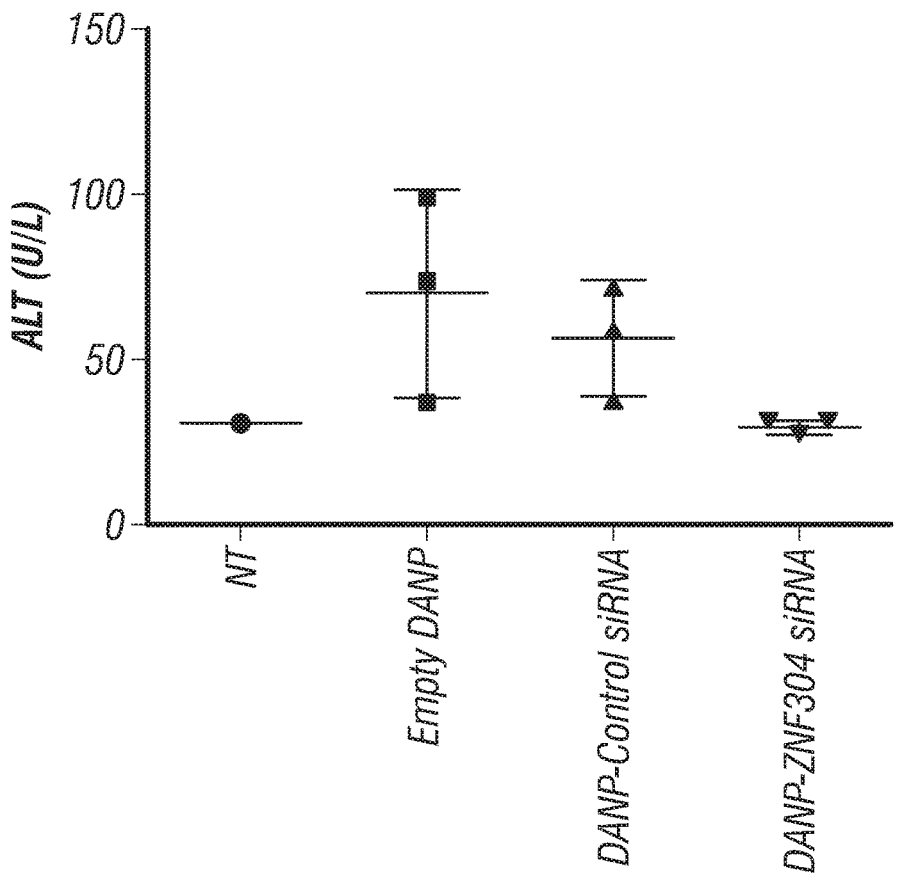
Figure 15D:
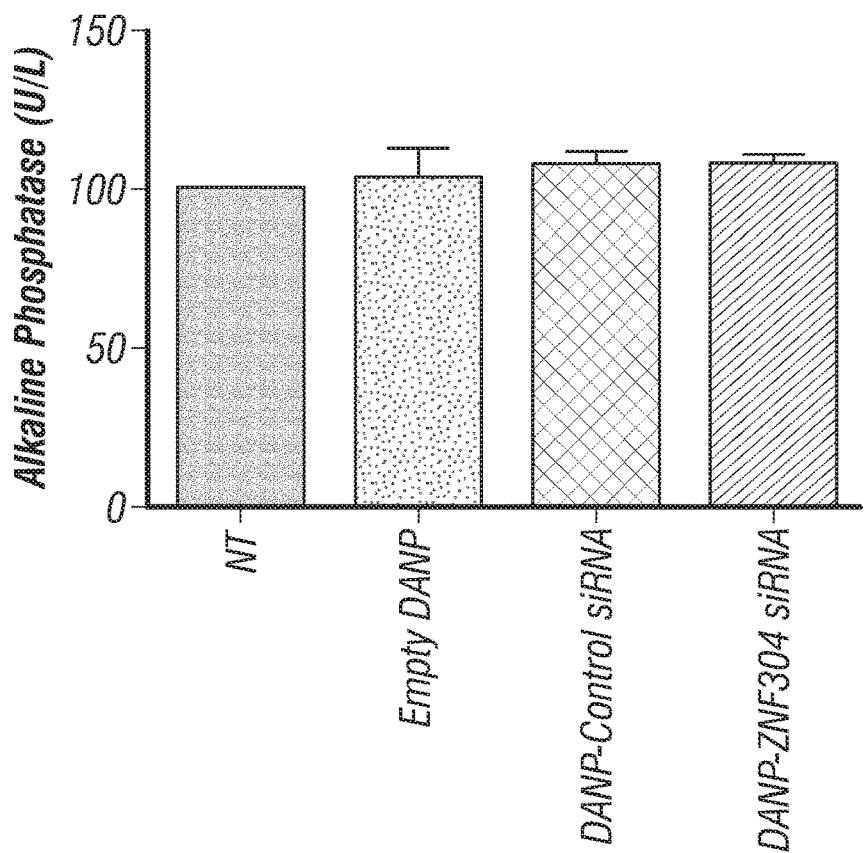

To determine the link between ZNF304-mediated β1 integrin and anoikis, a rescue experiment was performed. HeyA8 and SKOV3IP1 cells were transfected with either control siRNA or ZNF304 siRNA. Next, cells were transiently transfected with either empty vector or β1 integrin-expressing vector and transferred to anoikis plates. Both HeyA8 and SKOV3IP1 cells that were transfected with β1 integrin-expressing vector showed increased survival and decreased anoikis rates (FIG. 4C left and right, respectively). Furthermore, silencing ZNF304 increased the anoikis sensitivity and death rate of HeyA8 cells even in the presence of high β1 integrin expression. In addition, mutations (5 bp deletion on the binding site) were generated on the ZNF304 overexpressing vector that led to insensitivity for ZNF304 siRNA-1 (FIG. 14). The rescue experiment was performed using the ZNF304 overexpressing vector and mutant ZNF304 overexpressing vector. Immunoblotting showed that overexpression of mutant ZNF304 (insensitive for ZNF304 siRNA-1) led to a decrease in PARP cleavage, indicating the lack of anoikis in these cells (FIG. 14).

Example 5—Sustained in Vivo ZNF304 Gene Silencing

On the basis of the in vitro findings, whether ZNF304 gene silencing would be effective in treating orthotopic murine models of ovarian carcinoma was investigated. For the in vivo experiments, a novel delivery system designed for sustained and prolonged gene silencing was developed and characterized. Dual assembly nanoparticles (DANP) were prepared by using a chitosan core coated with poly-lactic acid (PLA). Both PLA and chitosan are non-toxic, biodegradable, and easy to manipulate.

For the preparation of chitosan particles, chitosan was mixed with tripolyphosphate (TPP) in the absence of organic solvents to allow for ionic crosslinking to occur between the amino groups of the chitosan backbone and the negatively charged phosphates of the TPP. Following preparation of the chitosan nanoparticles, different amount of PLA and different organic solvents, such as acetone, dichloromethane, chloroform, were used to identify the optimum ratio for coating the chitosan particles with PLA. The particles were chemically characterized by NMR spectroscopy and were morphologically characterized by atomic force microscopy (AFM) and scanning electron microscopy (SEM).

Figure 8A:
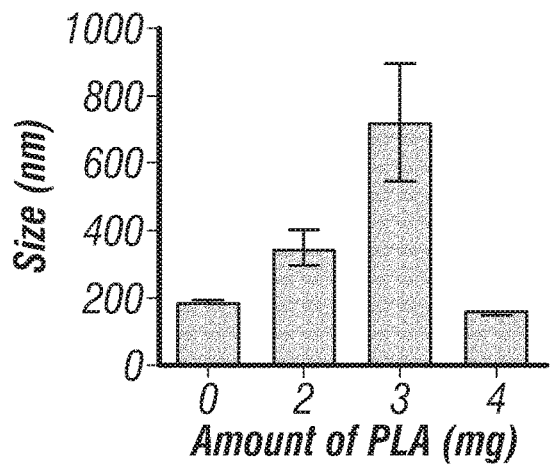
FIGS. 8A-C. Physiochemical properties of siRNA-incorporated DANP in terms of particle size and zeta potential. (A) Effect of PLA amount on nanoparticle diameter and zeta potential. All experiments were performed in triplicate and the error bars are SE. (B) Effect of PVA amount on nanoparticle diameter and zeta potential. All experiments were performed in triplicate and the error bars are SE. (C) Effect of sonication time on nanoparticle diameter. Experiments were performed in triplicate and error bars are SE.
Figure 8A:
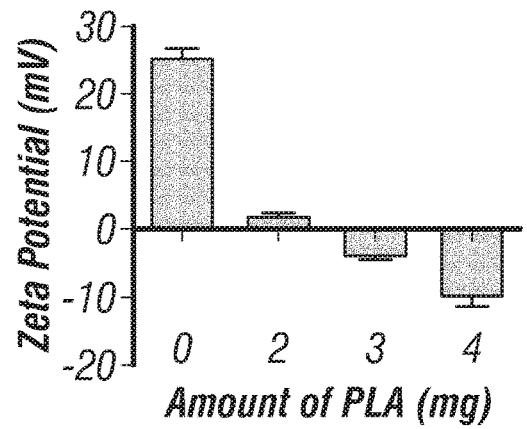
Figure 8B:
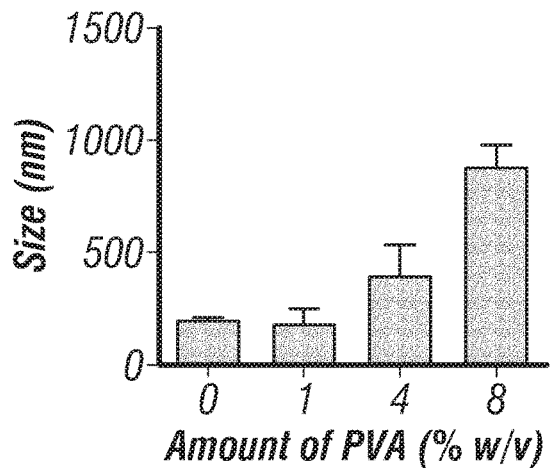
Figure 8B:
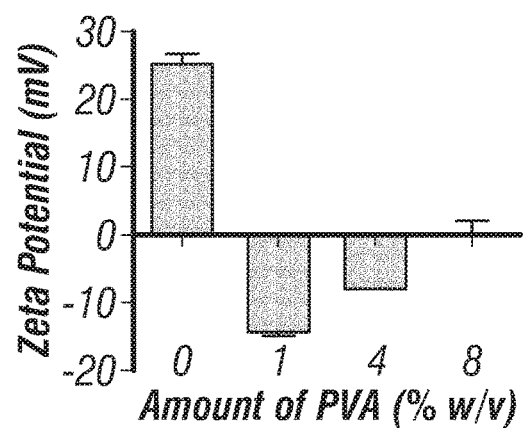
Figure 8C:
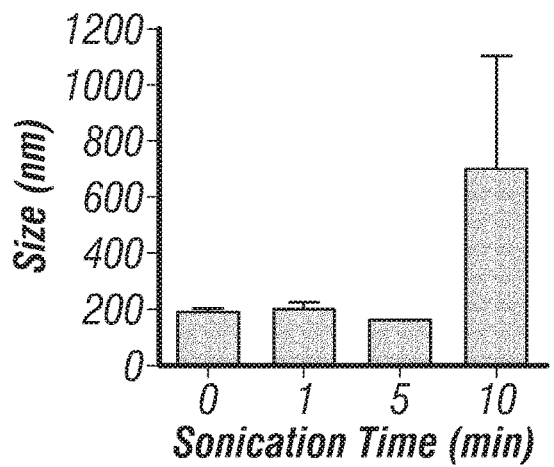

In order to optimize a viable formulation of siRNA-DANP, the physicochemical characteristics of the nanoparticles were studied. Size and zeta potential (for surface charge) properties were measured by light scattering with a particle size analyzer and Zeta Plus using different parameters, such as amount of PLA, amount of surfactant (PVA), and different sonication times (FIGS. 8A-C).

The optimized particles had a diameter of 150-200 nm and a zeta potential of −10 mV, which corresponded to a neutral range (FIGS. 5A and 5B, respectively). Atomic force microscopy (AFM) images demonstrated the spherical morphology and size distribution of the DANP (FIG. 5C). The coating characteristics of chitosan nanoparticles and DANP were studied using Fourier Transform Infrared Spectroscopy analysis, which relies on frustrated total internal reflection (FTIR), a technique used for fingerprint image acquisition. These studies confirmed the presence of PLA on the chitosan nanoparticles.

Figure 5D:
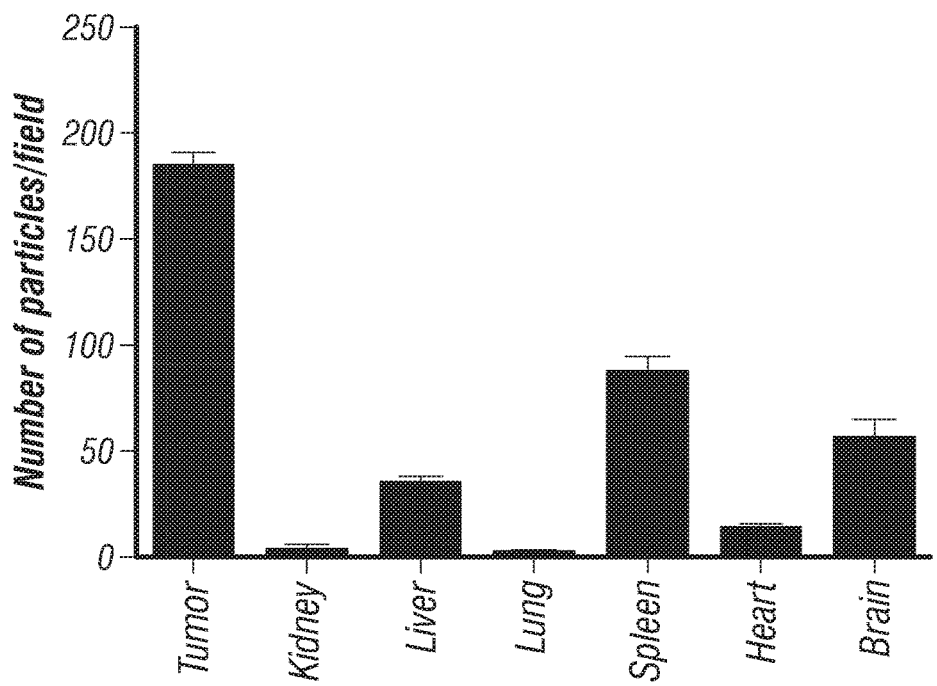

This optimized nanoparticle formulation was used for all subsequent experiments owing to their small size, slight negative charge, and high efficiency at incorporating siRNA. siRNA was incorporated in the chitosan core by using chitosan/tripolyphosphate at a 3:1 ratio, which yielded more than 75% loading efficiency, as previously described (Lu et al., 2010). Next, the tissue distribution of the DANP was determined by labeling the particles with rhodamine 6G and administering these red fluorescence-labeled particles as a single dose intravenously to HeyA8 tumor-bearing mice. Twenty-four hours later, the mice were euthanized, and their major organs and the tumors were removed, processed, and sectioned. The number of particles in each field was assessed by fluorescence microscopy (FIG. 5D). These results demonstrated that DANP were taken up by tumor cells in vivo.

Figure 5E:
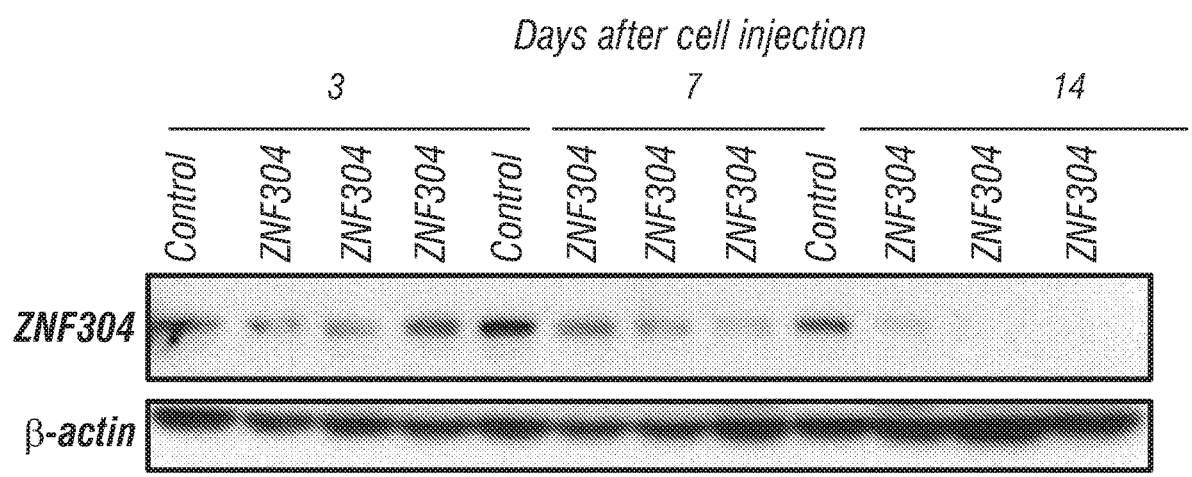

In the first set of experiments, the duration of in vivo DANP-mediated ZNF304 silencing in an orthotopic HeyA8 mouse model was determined. ZNF304-siRNA-DANP (300 µg/kg body weight) was administered as a single intravenous injection two weeks after tumor inoculation. Groups of mice were euthanized on day 3, 7, and 14 after injection. Tumors were collected and analyzed by immunoblotting to determine ZNF304 protein expression levels. ZNF304 protein silencing started at day 3 and continued up to 14 days after a single administration of ZNF304-siRNA-DANP (FIG. 5E).

Figure 5F:
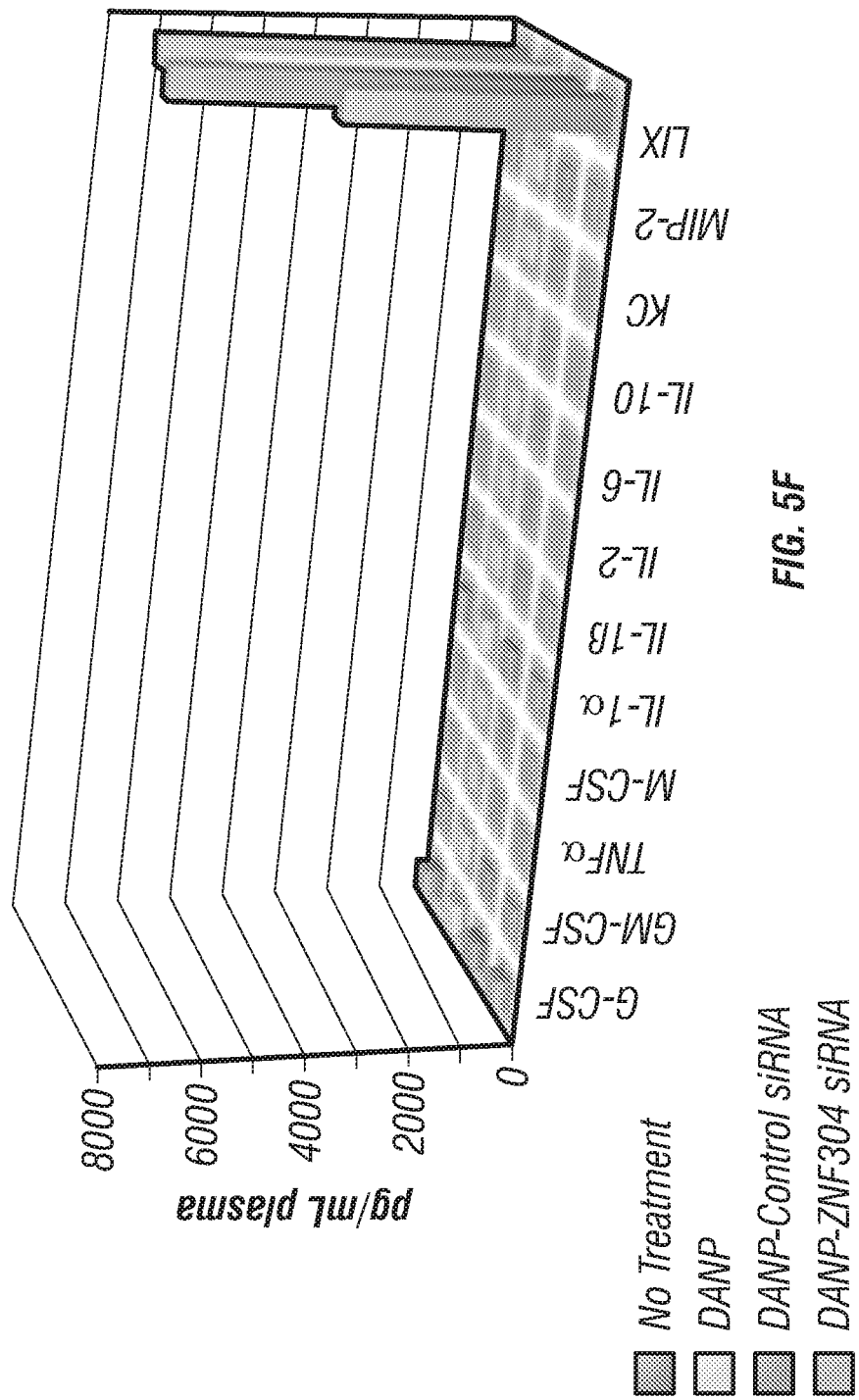

Next, inflammatory cytokine responses were assessed in the serum of C57 black mice. Mice were treated with single i.v. injections of DANP alone (n=6), DANP-Control siRNA (n=6), DANP-ZNF304 siRNA (n=6), or no treatment (n=2) (FIG. 5F) and serum was collected after 72 h using cardiac puncture. A Luminex assay designed to detect 12 pro-inflammatory cytokines (LIX, MIP-2, KC, IL-10, IL-6, IL-2, IL-1β, IL-1α, M-CSF, TNFα, GM-CSF, G-CSF) was used. The results obtained did not show any significant increase in these cytokines. Tissue samples were also obtained for post-mortem histopathology studies (brain, spleen, liver and kidney). H&E staining of the various tissues were analyzed by a veterinary pathologist; no inflammatory changes were observed in the tissues studied. Blood chemistries to assess liver (ALT and Alk Phosp) and kidney function (BUN and S. Creatinine) were also conducted (FIGS. 15A-D); hematologic profile (Complete Blood Counts, with differential and platelets: Hgb, Hct including red blood cell parameters are shown in Table 6). All parameters studies were within normal range (Schnell et al., 2002). Furthermore, tissue assessment using H&E did not disclose any toxicity..

TABLE 6

Summary data of hematology parameters after administration of Empty DANP, DANP-Control siRNA, and DANP-ZNF304 siRNA

| Parameter | Units | NT (n = 1) Mean | Empty DANP (n = 4) | | | | DANP-Control siRNA (n = 4) | | | | DANP-ZNF304 siRNA (n = 4) | | | |
|---|---|---|---|---|---|---|---|---|---|---|---|---|---|---|
| | | | Mean | Min | Max | SD | Mean | Min | Max | SD | Mean | Min | Max | SD |
| White Blood Cell Count | 10.e3/uL | 1.0 | 2.8 | 2.0 | 4.0 | 0.9 | 4.1 | 2.0 | 5.6 | 1.5 | 4.3 | 2.3 | 5.8 | 1.5 |
| Red Blood Cell Count | 10.e6/uL | 10.7 | 10.1 | 9.7 | 10.4 | 0.4 | 10.5 | 10.0 | 11.0 | 0.5 | 10.1 | 9.7 | 10.7 | 0.5 |
| Hemoglobin | g/dL | 15.4 | 14.8 | 14.1 | 15.5 | 0.6 | 15.1 | 14.3 | 15.5 | 0.6 | 14.5 | 14.0 | 15.2 | 0.5 |
| Hematocrit | % | 52.9 | 50.4 | 49.4 | 52.0 | 1.3 | 51.9 | 49.6 | 54.4 | 2.2 | 49.8 | 48.7 | 52.6 | 49.8 |
| MCV | fL | 49.5 | 49.7 | 49.1 | 51.0 | 49.7 | 49.2 | 48.0 | 50.1 | 0.8 | 49.3 | 48.4 | 50.1 | 0.7 |
| MCH | pg | 14.4 | 14.6 | 14.4 | 14.9 | 0.2 | 14.4 | 14.2 | 14.6 | 0.2 | 14.4 | 14.1 | 14.9 | 0.4 |
| MCHC | g/dL | 29.0 | 29.3 | 29.2 | 29.9 | 29.3 | 29.2 | 28.6 | 29.6 | 0.4 | 29.2 | 28.7 | 29.1 | 0.5 |
| RDW | % | 13.3 | 13.5 | 13.0 | 13.9 | 0.5 | 13.0 | 12.7 | 13.2 | 0.2 | 13.4 | 13.2 | 13.6 | 0.2 |
| Platelet Count | 10.e3/uL | 582.0 | 705.0 | 425 | 833 | 188.3 | 889.6 | 834 | 1094 | 889.6 | 981.3 | 990 | 1047 | 60.7 |
| MPV | fL | 6.3 | 6.7 | 6.1 | 7.4 | 0.5 | 6.3 | 6.1 | 6.6 | 0.2 | 6.2 | 6.1 | 6.3 | 0.1 |
| Segs | % | 17.2 | 12.7 | 11.6 | 14.0 | 1.0 | 9.2 | 7.4 | 12.3 | 2.0 | 13.7 | 9.7 | 16.5 | 3.2 |
| Lymphs | % | 71.7 | 78.6 | 72.0 | 83.0 | 4.9 | 86.3 | 83.0 | 88.7 | 2.1 | 82.2 | 79.0 | 86.3 | 3.6 |
| Monos | % | 1.7 | 4.2 | 1.6 | 9.0 | 3.4 | 1.9 | 1.1 | 3.1 | 0.8 | 1.5 | 1.0 | 1.9 | 0.4 |
| Eos | % | 8.3 | 3.5 | 3.0 | 5.0 | 1.1 | 1.5 | 1.6 | 2.6 | 0.7 | 1.4 | 0.9 | 1.8 | 0.5 |
| Basos | % | 0.5 | 0.8 | 0.2 | 2.0 | 1.1 | 0.2 | 0.1 | 0.3 | 0.1 | 0.4 | 0.1 | 0.6 | 0.2 |
| LUC | % | 0.7 | 0.9 | | | 0.0 | 0.8 | 0.5 | 1.0 | 0.2 | 1.0 | 0.6 | 1.6 | 0.4 |

Figure 6A:
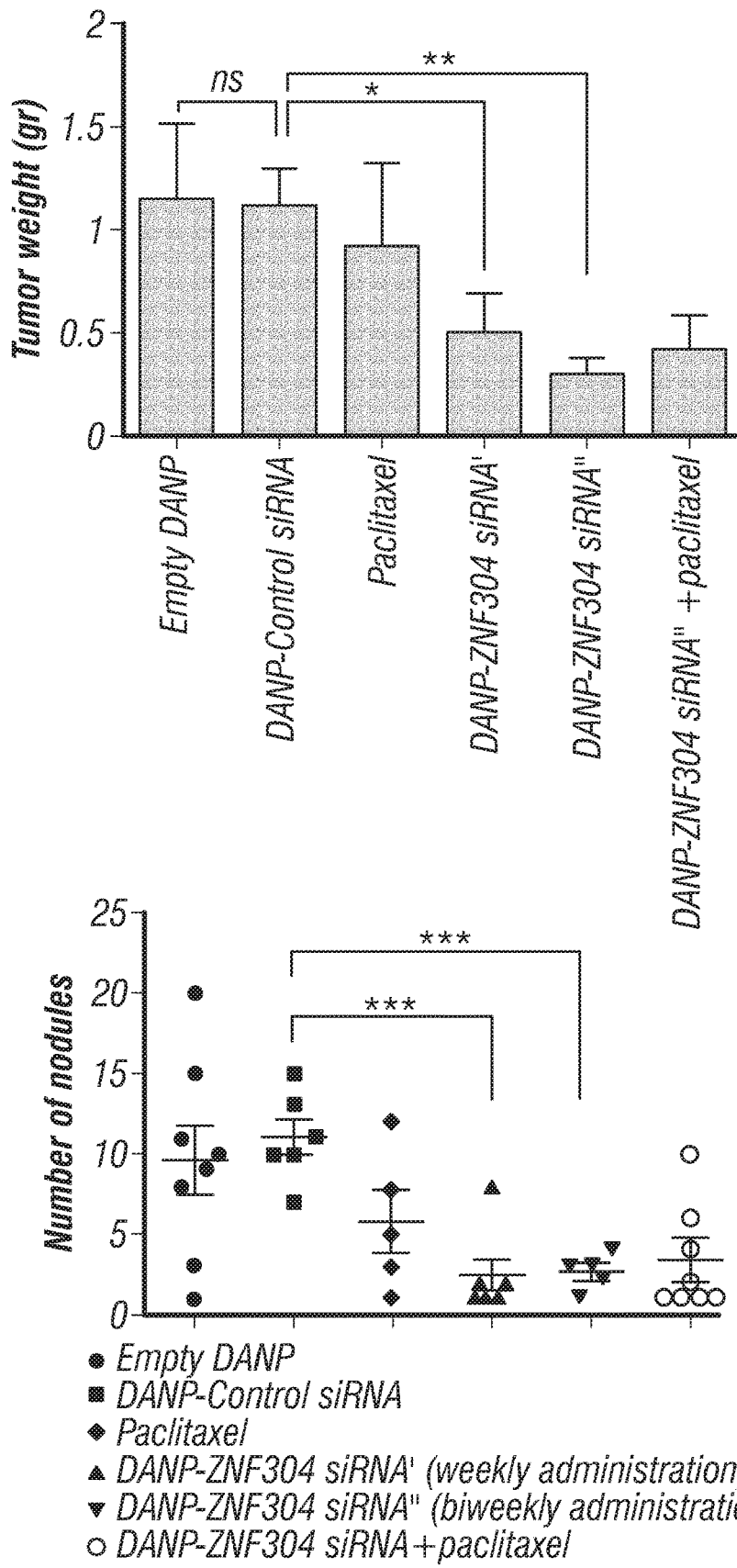
FIGS. 6A-D. Effects of in vivo ZNF304 gene silencing on tumor growth and vasculature. (A) Effect of ZNF304 siRNA-DANP treatment on tumor weight (top panel) and number of nodules (bottom panel) in HeyA8 orthotopic murine model. (P-values obtained with Student's t-test; *P<0.05; P<0.01; *P<0.001; or ****P<0.0001; compared with control siRNA treated group; bars and error bars represent mean values and the corresponding SEM. (B) Knockdown of ZNF304 by ZNF304 siRNA-DANP and the effect of treatment in SKOV3 tumor weight (top panel) and number of nodules (bottom panel). Data are presented as mean±sem (n=10/group). *P<0.05; P<0.01; *P<0.001; or ****P <0.0001 (Student's t-test). (C) Kaplan-Meier survival curve illustrating the effects of DANP-ZNF304 siRNA treatment versus Control siRNA treatment for the in vivo OVCA-432 survival model. Survival curves indicate that biweekly treatment of DANP-ZNF304 siRNA improves survival in vivo [n=8/group, P=0.01 (Control siRNA versus ZNF304 siRNA), Log-rank (Mantel-Cox) test]. Lines at 60 days are, from top to bottom, DANP-ZNF304 siRNA+cisplatin, DANP-ZNF304 siRNA, DANP-Control siRNA+cisplatin, and DANP-Control siRNA. (D) Viability of epithelial cells in ascites of mice. DANP-siRNA was administered intravenously when ascites was detectable. Ascites was removed seven days after a single administration and viability of epitelial cells were detected by FITC-Epcam and PI staining followed by flow cytometry. (n=3, P<0.0001, Student's t-test).

Example 6—ZNF304 Gene Silencing Leads to Antitumor Activity in Orthotopic Models of Ovarian Carcinoma On the basis of these findings, the antitumor activity of weekly or biweekly ZNF304 silencing was examined in two orthotopic ovarian carcinoma mouse models, HeyA8 and SKOV3IP1. In the first model, mice were injected with HeyA8 cells to induce tumors and one week later were randomly assigned to six treatment groups (10 mice in each group): DANP alone, control siRNA-DANP, ZNF304-siRNA-DANP (150 µg/kg body weight) administered weekly, and ZNF304-siRNA-DANP (300 µg/kg body weight) administered biweekly, or, since paclitaxel is commonly used for ovarian carcinoma treatment and combines effectively with many biologically targeted agents, paclitaxel only or a combination of paclitaxel plus ZNF304 siRNA-DANP (300 µg/kg body weight, biweekly administration) (FIG. 6A). Significant reductions in tumor weight were observed in the groups treated with ZNF304 siRNA-DANP weekly or biweekly. Mice treated with ZNF304 siRNA-DANP had a significantly lower tumor burden (62% reduction in tumor weight; P<0.01) (FIG. 6A, left panel) and had 50% fewer nodules than did mice treated with control siRNA-DANP (P<0.05) (FIG. 6A, right panel). Moreover, the ZNF304 siRNA-DANP treatment group had significantly fewer nodules than did the control group (P=0.0001, weekly administration; P=0.0001, biweekly administration; Student's t-test).

Figure 6B:
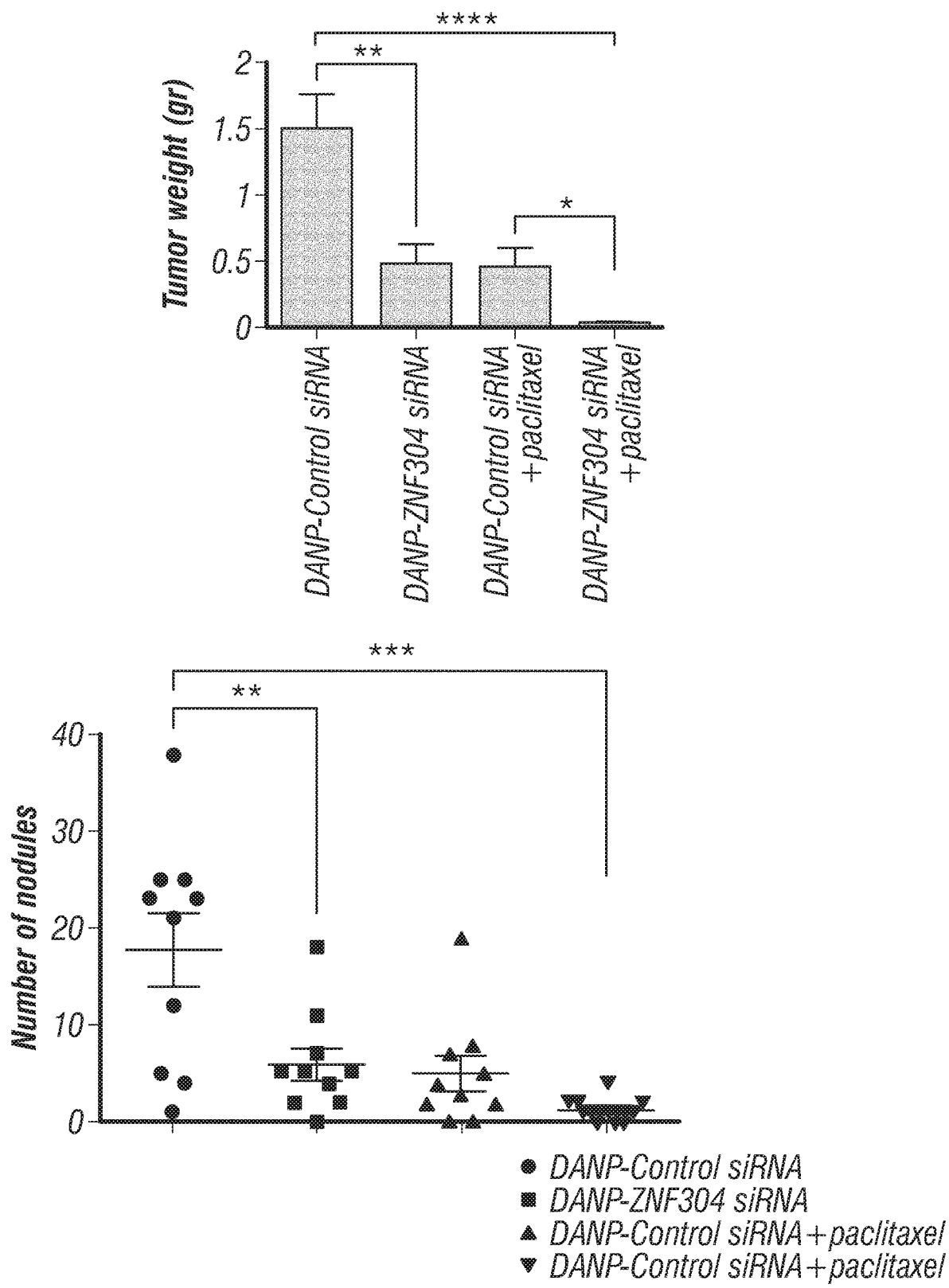
Figure 16B:
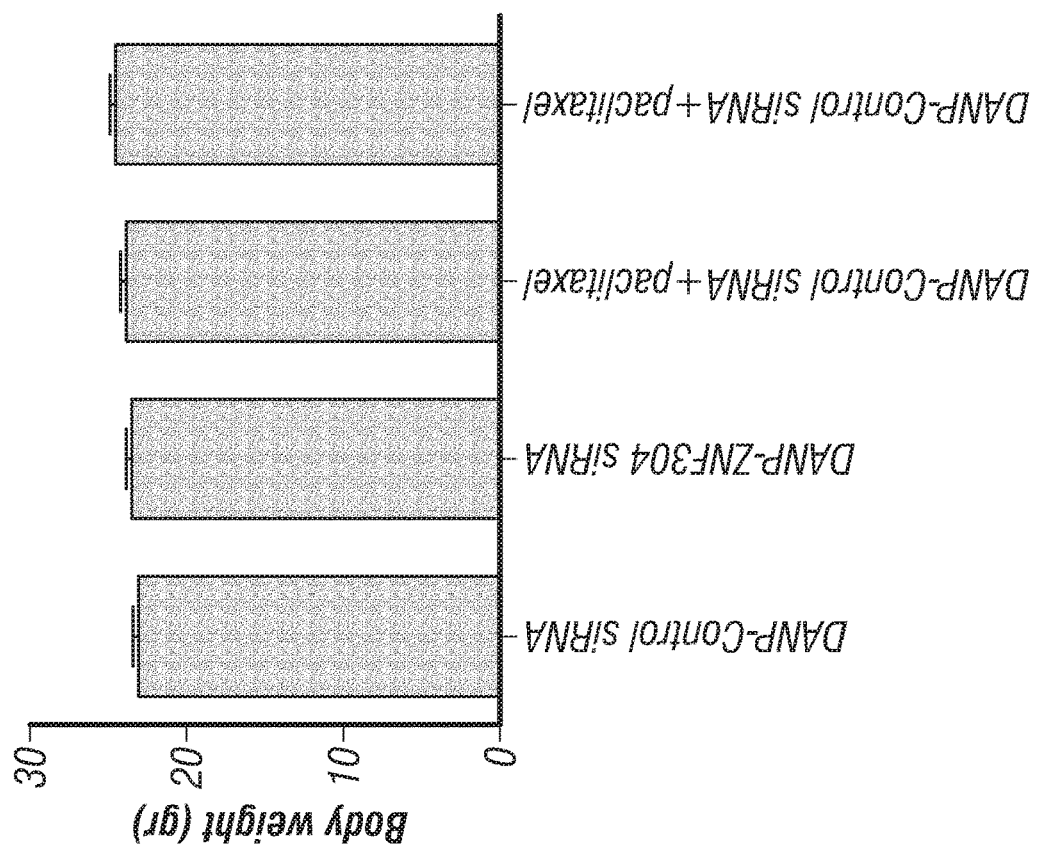
FIGS. 16A-B. Body weight measurements at the end of animal studies. Body weight in (A) HeyA8 and in (B) SKOV3IP1 orthotopic mouse model of OC.
Figure 16A:
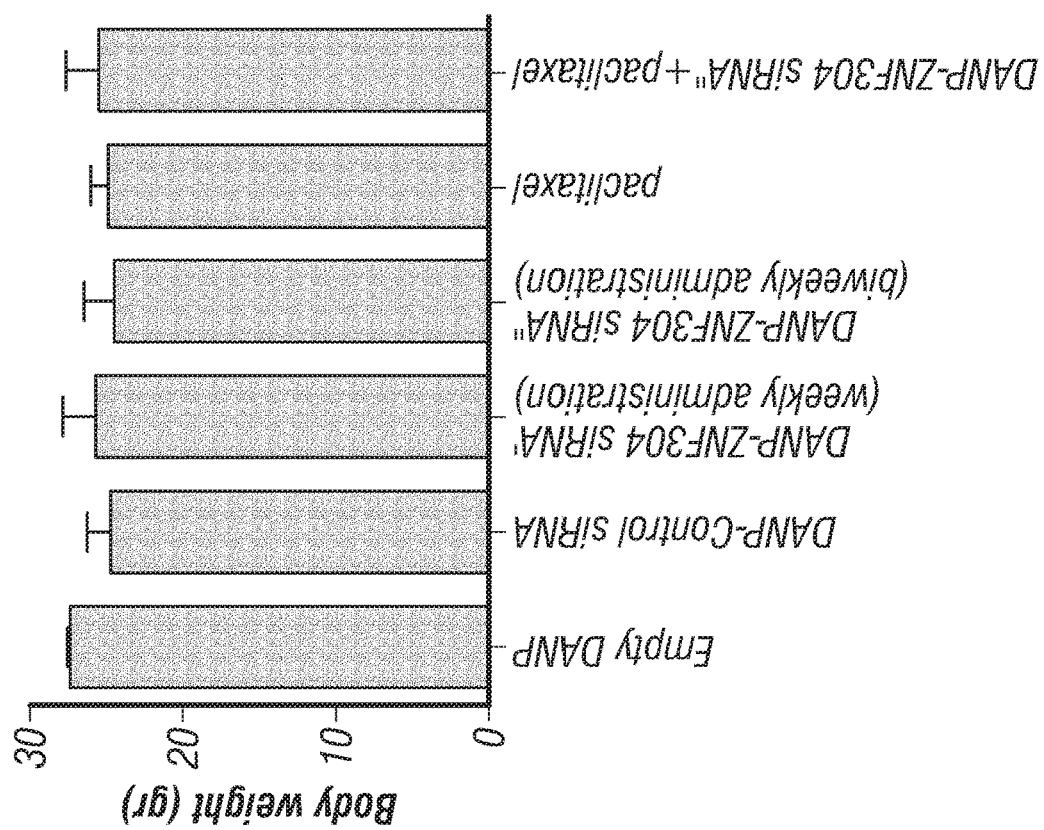

In the second orthotopic model (SKOV3IP1), the treatment groups were (1) control siRNA-DANP, (2) ZNF304 siRNA-DANP, (3) control siRNA-DANP plus paclitaxel, and (4) ZNF304 siRNA-DANP plus paclitaxel (n=10/group). siRNA-DANP was administered intravenously every two weeks in all treatment groups. Tumors removed from mice treated with ZNF304 siRNA-DANP alone weighed 60% less than those of mice treated with DANP-control siRNA (FIG. 6B, left panel). The number of nodules was dramatically reduced in mice treated with either ZNF304 siRNA-DANP or ZNF304 siRNA-DANP plus paclitaxel (FIG. 6B, right panel). The greatest reduction was observed in the group treated with both DANP-ZNF304 siRNA and paclitaxel. None of the groups in either mouse model showed decreased body weight, which indicates that the treatments were not toxic (FIGS. 16A-B). These data indicate that inhibiting ZNF304 results in antitumor activity in mouse models of ovarian carcinoma and that the DANP delivery system is an efficient tool for in vivo gene silencing.

Figure 17A:
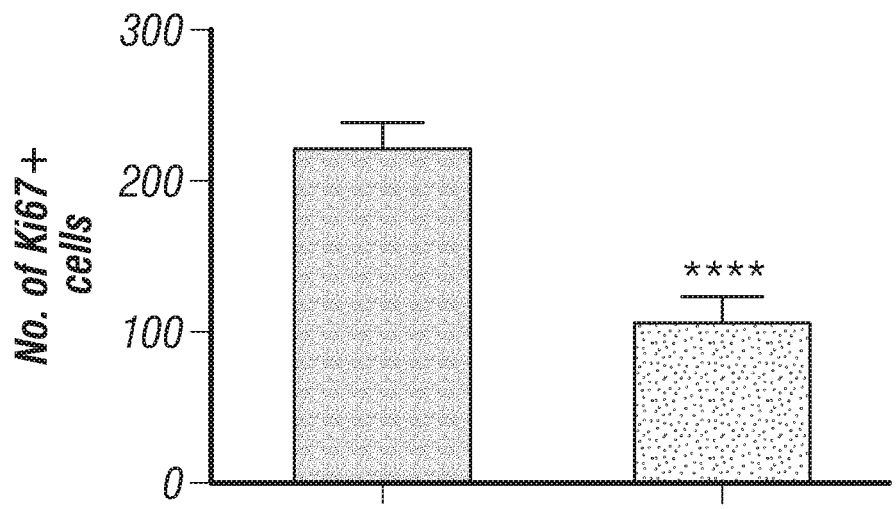
FIGS. 17A-B. Quantification and analysis of immunohistochemistry results. Quantification of (A) tumor proliferation (Ki67) and (B) microvessel density (CD31) in SKOV3 orthotopic murine model of OC. Number of positive cells were counted at 5 fields per slide after immunohistochemistry staining. Data are presented as mean±s.e.m. of n>3 experimental groups.*P>0.05, ****P >0.0001 (Student's t-test).
Figure 17B:
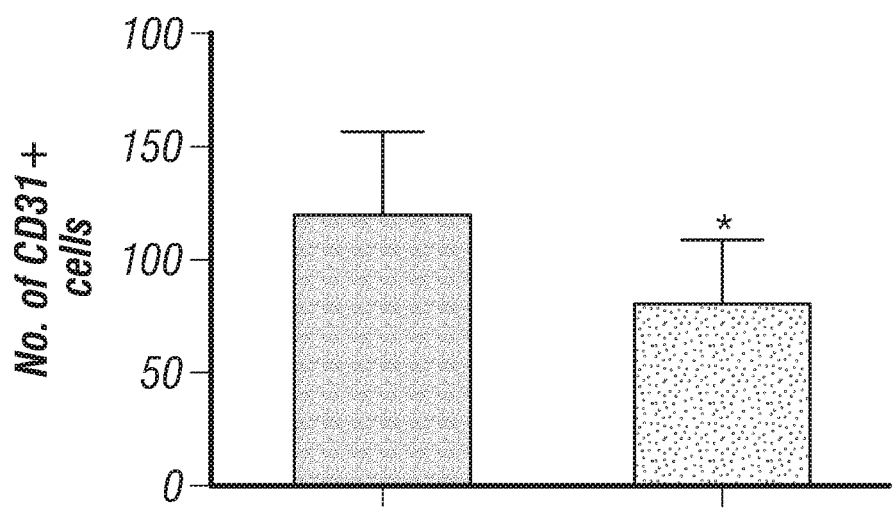

Given the in vitro effects of ZNF304 silencing, Ki67 and CD31 staining were performed to examine the biological effects of silencing ZNF304 on tumor cell proliferation and angiogenesis, respectively. Mice treated with ZNF304 siRNA-DANP showed significant reduction in cell proliferation compared to control group (P<0.0001) (FIGS. 17A-B). Given that ZNF304 transcriptionally regulates β1 integrin, which is required for endothelial cell adhesion, migration, and survival (Carlson et al., 2008; Weis and Cheresh, 2011), the effects of ZNF304 siRNA treatment on angiogenesis were also examined. The ZNF304 siRNA-DANP treatment group had significantly reduced microvessel density compared with the control (P=0.0252, Students's t test) (FIGS. 17A-B). These data showed that downregulation of ZNF304 was highly associated with decreased cell proliferation and decreased microvessel density.

Figure 6C:
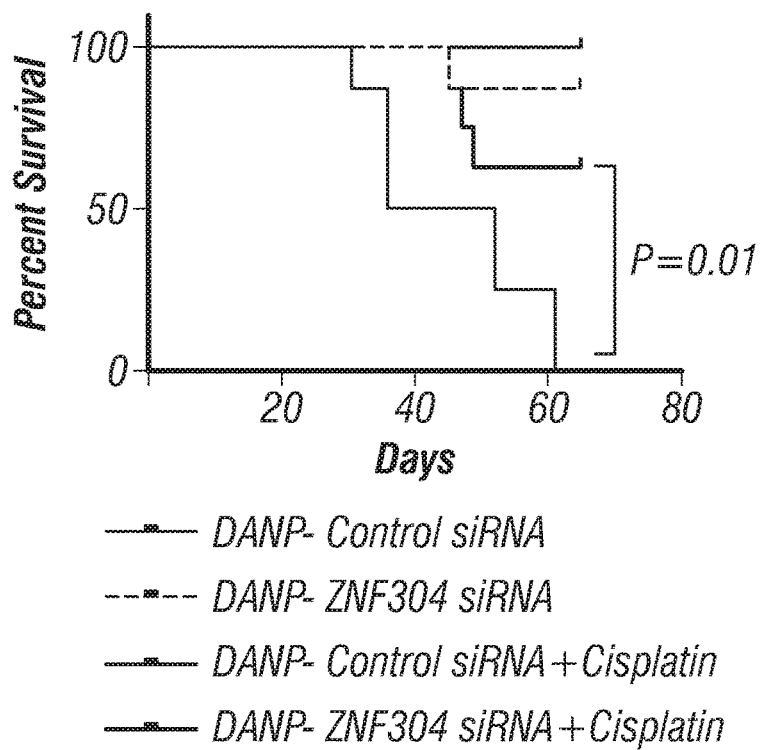

On the basis of efficacy data, the effects of DANP-ZNF304 siRNA treatment on the survival of tumor bearing mice was examined. For these experiments, mice were inoculated with OVCA-432 cells that represent HGSOC (Leung et al., 2014). Luciferase-labeled OVCA-432 cells ($3\times10^6$) were injected intraperitoneally to generate tumors in nude mice. The four groups (n=8/group) were treated with either: 1) DANP-Control siRNA, 2) DANP-ZNF304 siRNA, 3) DANP-Control siRNA+cisplatin, or 4) DANP-ZNF304 siRNA+cisplatin. The treatment started one week after tumor cell inoculation and the mice were monitored daily by three observers. Individual mice were euthanized on the day the core veterinarian recommended, based on moribund status. A Kaplan-Meier curve was generated based on the survival duration of mice (FIG. 6C). DANP-ZNF304 siRNA-based treatment significantly improved survival compared to DANP-Control siRNA treatment (n=8/group, p=0.01, Log-rank test). The analysis showed that the median survival for the DANP-Control siRNA treated group was 44 days, whereas it was not reached for the DANP-ZNF304 siRNA.

Figure 6D:
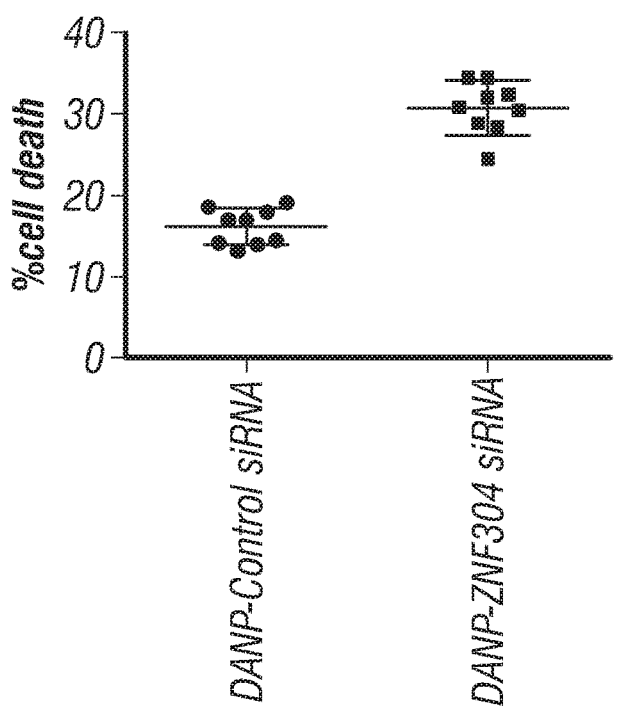
Figure 7:
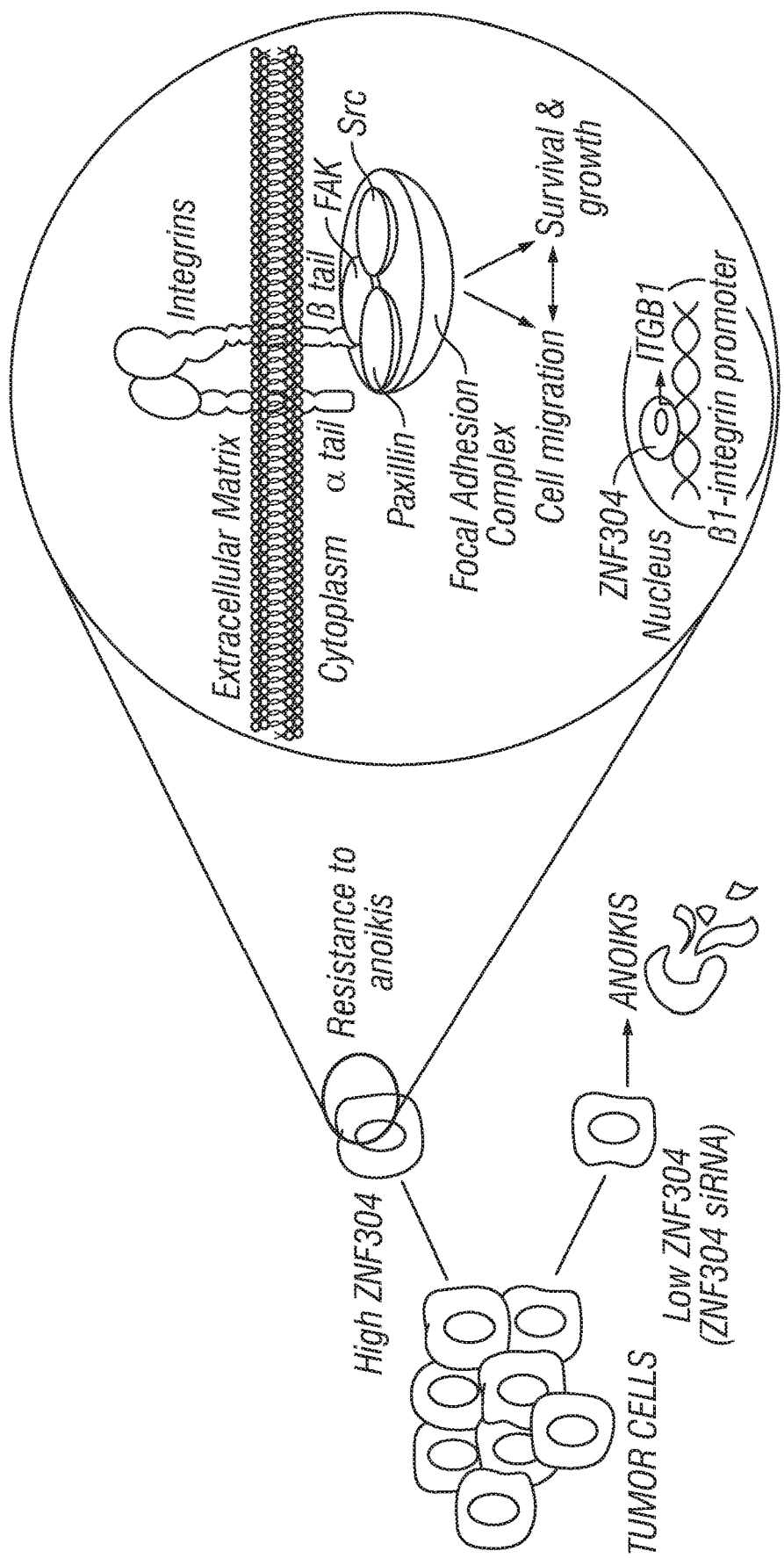
FIG. 7. A schematic representation of mechanisms by which ZNF304 downregulation enhances anoikis in tumor cells. The model illustrates that silencing ZNF304 leads to anoikis in tumor cells while high-ZNF304-expressing cells gain resistance to anoikis through increased integrin β1 expression and activation of focal adhesion complex members.

Next, whether ZNF304 silencing could directly increase the rates of anoikis in vivo was determined. For this question, the ovarian carcinoma MDAH 2774 cell line was used since it induces significant ascites in mice (Sood et al., 2010). MDAH 2774 cells were implanted into the peritoneal cavity of nude mice, and ascites production was observed 4-6 weeks post-inoculation. Next, the ascites for viable tumor epithelial cells was analyzed using fluorescein isothiocyanate (FITC)-labeled anti-epithelial cellular adhesion molecule antibody followed by flow cytometry analysis (FIG. 6D). The control group showed 16% (mean±SEM; 16.08±0.7280, n=3) epithelial cell death in ascites, whereas mice treated with intravenous ZNF304 siRNA-DANP had up to 30% (mean±SEM; 30.77±1.040, n=3) epithelial cell death. These results show that silencing ZNF304 significantly decreased the ability of ovarian carcinoma cells to survive in ascites (P<0.001, Student's t-test).

Example 7—The ZNF304-Integrin Axis Protects Against Anoikis in Cancer

ZNF304 is a novel transcriptional regulator of β1 integrin. Silencing ZNF304 resulted in antitumor activity and the induction of anoikis in malignant cells both in vitro and in vivo through β1 integrin downregulation. High ZNF304 mRNA expression was associated with worse survival in ovarian carcinoma patients. Furthermore, silencing ZNF304 enhanced the anoikis rate through inhibiting inside-out integrin signaling and accordingly blocking outside-in signaling.

Integrins are crucial for normal functions of multicellular organisms and critical at each step of cancer: tumorigenesis, progression, and metastasis (Desgrosellier and Cheresh, 2010). Integrins are regulated and activated by conformational changes, clustering, and trafficking (Margadant et al., 2011). These transmembrane proteins are an essential link between the extracellular matrix (ECM) and cytoplasm, and the signaling can be in two directions: outside-in or inside-out through the cytoplasmic β tail (Margadant et al., 2011). For example, β1 integrin promotes cell survival and regulates focal adhesion, leading to tumor metastasis in many types of cancer including ovarian carcinoma (Caccavari et al., 2010; Guo and Giancotti, 2004; Grzesiak et al., 2011; Mitra et al., 2011). In a recent study, moreover, Schiller and colleagues demonstrated that expression of α5β1 integrins is essential to sense the stiffness of fibronectin-based ECM, which is also critical for tumor metastasis (Minton, 2013; Schiller et al., 2013). Furthermore, several β1 integrin-targeting strategies, such as monoclonal antibodies and peptide inhibitors, showed activity in clinical trials for cancer therapy (Desgrosellier et al., 2010; Barkan and Chambers, 2011; Jahangiri et al., 2014). However, targeting ZNF304—the regulator of β1 integrin expression—may offer greater efficacy than targeting only activation of β1 integrin.

β1 integrin is a subunit of heterodimeric membrane adhesion receptors, and it can form heterodimers with integrin a subunits. For example, α4β1, α8β1, and αvβ1 are fibronectin-binding integrins; α3β1, 60 6β1, and α7β1 interact with laminin and nectin; and α1β1, α2β1, α10β1, and α11β1 bind to collagens (Brakebusch and Fassler, 2005; Giancotti, 2000). The first study showing the inside-out regulation of β1 integrin unraveled the control by R-Ras of the ligand-binding affinity of β1 integrin and fibronectin (Zhang et al., 1996). Thus, the regulation of integrin activation and affinity was known as a transcription-independent function of the Ras-linked mitogen-activated protein kinase pathway (Hughes et al., 1997; Kinbara et al., 2003). However, the transcriptional regulation of β1 integrin remained unknown. Here, it was found that the regulation of β1 integrin expression through ZNF304 is at the transcriptional level.

Previous studies showed that fibronectin and β1 integrin ligation, followed by activation of cytoplasmic 13 subunit, promotes the invasive migration of ovarian carcinoma cells through the ECM (Caswell et al., 2007). Myosin II and FAK mediate the phosphorylation of paxillin, reinforcing the cytoskeletal ECM linkage and driving focal adhesion maturation (Pasapera et al., 2010). Additionally, β1 integrin-FAK signaling directs the initial proliferation of micrometastatic cancer cells disseminated in the lungs, which indicates the role of integrin-FAK signaling in the metastatic cascade (Shibue et al., 2009). Thus, ZNF304 may be a regulator of this metastatic process. Correspondingly, silencing the key regulator ZNF304 decrease nodule formation, tumor growth and prolong survival in orthotopic mouse models of ovarian carcinoma.

The functional crosstalk between cell adhesion receptors and receptor tyrosine kinases contributes to cancer cell survival (Guo and Giancotti, 2004). The interaction between ErbB1 and β1 integrin induces tumor cell detachment, migration, and metastatic potential. β1 integrin was also shown to regulate epidermal growth factor receptor signaling in lung cancer cells (Morello et al., 2011) and to mediate epidermal growth factor-induced cell invasion in ovarian carcinoma cells (Lau et al., 2012). Furthermore, a recent study demonstrated an increased ErbB1-β1 integrin heteroassociation in high-grade astrocytomas and showed that this clinically relevant association can be targeted by molecular therapy (Petras et al., 2013). Therefore silencing ZNF304—the regulator of β1 integrin—may also inhibit epidermal growth factor receptor signaling, inhibiting cancer cell survival and slowing tumor progression.

Anoikis is a form of apoptosis in adherent nonmalignant cells caused by a lack of integrin-mediated survival signals from the ECM (Frisch and Francis, 1994; Kim et al., 2012). However, malignant cells develop resistance to anoikis, leading to increased metastatic potential (Simpson et al., 2008; Jenning et al., 2013). A seminal mechanistic work on anoikis unraveled its contribution to human cancer metastasis in several different malignancies (Sakamoto et al., 2011; Reginato et al., 2003; Sakamoto et al., 2010). Integrins are crucial in anoikis mechanism as major mediators of adhesion between cells and ECM proteins (Frisch and Ruoslahti, 1997; Frisch and Screaton, 2001). A recent study showed that activated integrins enhance the metastatic potential of prostate cancer cells by decreasing their sensitivity to anoikis during tumor dissemination and by increasing their interactions with ECM ligands during extravasation (Lee et al., 2013). This latter study suggested that in prostate cancer cells, β1 integrin is activated through an inside-out signaling, which also enhances its affinity for ligand binding. The interaction of β1 integrin with ECM ligands further activates β1 integrin through outside-in signaling.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,282,351
U.S. Pat. No. 4,806,474
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 6,506,559
U.S. Pat. No. 6,573,099
U.S. Pat. No. 6,673,611
U.S. Patent Appln. Publn. No. 2002/0168707
U.S. Patent Appln. Publn. No. 2002/0170849
U.S. Patent Appln. Publn. No. 2003/0051263
U.S. Patent Appln. Publn. No. 2003/0055020
U.S. Patent Appln. Publn. No. 2003/0129730
U.S. Patent Appln. Publn. No. 2003/0159161
U.S. Patent Appln. Publn. No. 2004/0019001
U.S. Patent Appln. Publn. No. 2004/0064842
U.S. Patent Appln. Publn. No. 2004/0247632
U.S. Patent Appln. Publn. No. 2004/0265839
U.S. Patent Appln. Publn. No. 2005/0042735
U.S. Patent Appln. Publn. No. 2005/0226938
U.S. Patent Appln. Publn. No. 2005/0245482
U.S. Patent Appln. Publn. No. 2006/0094666
U.S. Patent Appln. Publn. No. 2006/0189573
U.S. Patent Appln. Publn. No. 2006/0277632
U.S. Patent Appln. Publn. No. 2007/0116767
U.S. Patent Appln. Publn. No. 2007/0167400
U.S. Patent Appln. Publn. No. 2007/0311468
Abdul Azis, Role of cell adhesion molecules in invasion, anoikis resistance and drug resistance: An in vitro analysis using multiple phenotyping approach. In: Qatar Foundation Annual Research Forum Proceedings, 2013.

Allan and Peyron, Molecular weight manipulation of chitosan. I: Kinetics of depolymerization by nitrous acid, *Carbohydr. Res.*, 277:257-272, 1995.

Austin-Ward and Villaseca, Gene therapy and its applications. *Rev. Med. Chil.*, 126:838-845, 1998.

Barkan and Chambers, β1-integrin: a potential therapeutic target in the battle against cancer recurrence. *Clinical Cancer Research*, 17:7219-7223, 2011.

Benjamini and Hochberg, Controlling the false discovery rate: a practical and powerful approach to multiple testing. *Journal of the Royal Statistical Society Series B (Methodological)*, 57:289-300, 1995.

Bowen et al., Gene expression profiling supports the hypothesis that human ovarian surface epithelia are multipotent and capable of serving as ovarian cancer initiating cells. *BMC Medical Genomics*, 2:71, 2009.

Brakebusch and Fässler, β1 integrin function in vivo: adhesion, migration and more. *Cancer and Metastasis Reviews*, 24:403-411, 2005.

Bukowski et al., Signal transduction abnormalities in T lymphocytes from patients with advanced renal carcinoma: clinical relevance and effects of cytokine therapy. *Clin. Cancer Res.*, 4:2337-2347, 1998.

Caccavari et al., Integrin signaling and lung cancer. *Cell Adhesion & Migration*, 4:124-129, 2010.

Carlson et al., Cell-autonomous requirement for β1 integrin in endothelial cell adhesion, migration and survival during angiogenesis in mice. *Development*, 135:2193-2202, 2008.

Casey et al., Molecular signatures suggest a major role for stromal cells in development of invasive breast cancer. *Breast Cancer Research and Treatment*, 114:47-62, 2009.

Caswell et al., Rab25 associates with α5β1 integrin to promote invasive migration in 3D microenvironments. *Developmental Cell*, 13:496-510, 2007.

Cheema et al., Par-4 transcriptionally regulates Bcl-2 through a WT1-binding site on the bcl-2 promoter. *Journal of Biological Chemistry*, 278:19995-20005, 2003.

Christodoulides et al., Immunization with recombinant class 1 outer-membrane protein from *Neisseria meningitidis*: influence of liposomes and adjuvants on antibody avidity, recognition of native protein and the induction of a bactericidal immune response against meningococci. *Microbiology*, 144:3027-3037, 1998.

Davidson et al., Intralesional cytokine therapy in cancer: a pilot study of GM-CSF infusion in mesothelioma. *J. Immunother.*, 21:389-398, 1998.

Desgrosellier and Cheresh, Integrins in cancer: biological implications and therapeutic opportunities. *Nature Reviews Cancer*, 10:9-22, 2010.

Domard and Cartier, Glucosamine oligomers: 1. Preparation and characterization, *Int. J Biol. Macromol.*, 11:297-302, 1989.

Fire et al., Potent and specific genetic interference by double-stranded RNA in *Caenorhabditis elegans*, *Nature*, 391:806-811, 1998.

Frisch and Francis, Disruption of epithelial cell-matrix interactions induces apoptosis. *The Journal of Cell Biology*, 124:619-626, 1994.

Frisch and Ruoslahti, Integrins and anoikis. *Current Opinion in Cell Biology*, 9:701-706, 1997.

Frisch and Screaton, Anoikis mechanisms. *Current Opinion in Cell Biology*, 13:555-562, 2001.

Giancotti, Complexity and specificity of integrin signalling. *Nature Cell Biology*, 2:E13-E14, 2000.

Grzesiak et al., Knockdown of the β1 integrin subunit reduces primary tumor growth and inhibits pancreatic cancer metastasis. *International Journal of Cancer*, 129:2905-2915, 2011.

Guo and Giancotti, Integrin signalling during tumour progression. *Nature Reviews Molecular Cell Biology*, 5:816-826, 2004.

Halder et al., Focal adhesion kinase targeting using in vivo short interfering RNA delivery in neutral liposomes for ovarian carcinoma therapy. *Clinical Cancer Research*, 12:4916-4924, 2006.

Han et al., Targeted gene silencing using RGD-labeled chitosan nanoparticles. *Clinical Cancer Research*, 16:3910-3922, 2010.

Hanibuchi et al., Therapeutic efficacy of mouse-human chimeric anti-ganglioside GM2 monoclonal antibody against multiple organ micrometastases of human lung cancer in NK cell-depleted SCID mice. *Int. J. Cancer*, 78:480-485, 1998.

Hellstrand et al., Histamine and cytokine therapy. *Acta Oncol.*, 37:347-353, 1998.

Hughes et al., Suppression of integrin activation: a novel function of a Ras/Raf-initiated MAP kinase pathway. *Cell*, 88:521-530, 1997.

Hui and Hashimoto, Pathways for Potentiation of Immunogenicity during Adjuvant-Assisted Immunizations with Plasmodium falciparum Major Merozoite Surface Protein 1. *Infec. Immun.*, 66:5329-5336, 1998.

Jahangiri et al., β1 Integrin: Critical Path to Antiangiogenic Therapy Resistance and Beyond. *Cancer Research*, 74:3-7, 2014.

Jenning et al., Bit1 in anoikis resistance and tumor metastasis. Cancer Letters, 333:147-151, 2013.

Ju et al., Interleukin-18 gene transfer increases antitumor effects of suicide gene therapy through efficient induction of antitumor immunity, *Gene Ther.*, 7:1672-1679, 2000.

Kamat et al., Metronomic chemotherapy enhances the efficacy of antivascular therapy in ovarian cancer. *Cancer Research*, 67:281-288, 2007.

Kim et al., Functional roles of Src and Fgr in ovarian carcinoma. *Clinical Cancer Research*, 17:1713-1721, 2011.

Kim et al., Anoikis resistance: an essential prerequisite for tumor metastasis. International Journal of Cell Biology 2012:306879, 2012.

Kinbara et al., Ras GTPases: integrins' friends or foes? *Nature Reviews Molecular Cell Biology*, 4:767-778, 2003.

Kipps et al., Meeting the challenge of ascites in ovarian cancer: new avenues for therapy and research. *Nature Reviews Cancer*, 13:273-282, 2013.

Landen et al., Therapeutic EphA2 gene targeting in vivo using neutral liposomal small interfering RNA delivery. *Cancer Research*, 65:6910-6918, 2005.

Landen et al., Efficacy and antivascular effects of EphA2 reduction with an agonistic antibody in ovarian cancer. *Journal of the National Cancer Institute*, 98:1558-1570, 2006.

Landen et al., Targeting aldehyde dehydrogenase cancer stem cells in ovarian cancer. *Molecular Cancer Therapeutics*, 9:3186-3199, 2010.

Langley et al., Tissue-specific microvascular endothelial cell lines from H-2Kb-tsA58 mice for studies of angiogenesis and metastasis. *Cancer Research*, 63:2971-2976, 2003.

Lau et al., Integrin β1 mediates epithelial growth factor-induced invasion in human ovarian cancer cells. *Cancer Letters*, 320:198-204, 2012.

Lee et al., Targeting constitutively activated β1 integrins inhibits prostate cancer metastasis. *Molecular Cancer Research*, 11:405-417, 2013.

Leung et al., Calcium-dependent FAK/CREB/TNNC1 signalling mediates the effect of stromal MFAPS on ovarian cancer metastatic potential. *Nature Communications*, 5:5092, 2014.

Li et al., Analysis of 43 kb of the chlorella virus PBCV-1 330-kb genome: map positions 45 to 88, *Virology*, 212: 134-150, 1995.

Lu et al., Dual targeting of endothelial cells and pericytes in antivascular therapy for ovarian carcinoma. *Clinical Cancer Research*, 13:4209-4217, 2007a.

Lu et al., Gene alterations identified by expression profiling in tumor-associated endothelial cells from invasive ovarian carcinoma. *Cancer Research*, 67:1757-1768, 2007b.

Lu et al., Impact of vessel maturation on antiangiogenic therapy in ovarian cancer. *American Journal of Obstetrics and Gynecology*, 198:477, e471-477, e410, 2008.

Lu et al., Regulation of tumor angiogenesis by EZH2. *Cancer Cell*, 18:185-197, 2010.

Margadant et al., Mechanisms of integrin activation and trafficking. *Current Opinion in Cell Biology*, 23:607-614, 2011.

Minton, Cell adhesion: Integrating the integrin response. *Nature Reviews Molecular Cell Biology*, 14:401-401, 2013.

Mitchell et al., Active-specific immunotherapy for melanoma, *J. Clin. Oncol.*, 8:856-869, 1990.

Mitchell et al., Active specific immunotherapy of melanoma with allogeneic cell lysates, *Ann. N.Y. Acad. Sci.*, 690: 153-166, 1993.

Mitra et al., Ligand-independent activation of c-Met by fibronectin and α5β1-integrin regulates ovarian cancer invasion and metastasis. *Oncogene*, 30:1566-1576, 2011.

Morello et al., β1 integrin controls EGFR signaling and tumorigenic properties of lung cancer cells. *Oncogene*, 30:4087-4096, 2011.

Morton et al., Technical details of intraoperative lymphatic mapping for early stage melanoma, *Arch. Surg.*, 127:392-399, 1992.

Naora and Montell, Ovarian cancer metastasis: integrating insights from disparate model organisms. *Nature Reviews Cancer*, 5:355-366, 2005.

Pasapera et al., Myosin II activity regulates vinculin recruitment to focal adhesions through FAK-mediated paxillin phosphorylation. *The Journal of Cell Biology*, 188:877-890, 2010.

Persikov et al., Predicting DNA recognition by Cys2His2 zinc finger proteins. *Bioinformatics*, 25:22-29, 2009.

Petrás et al., Molecular interactions of ErbB1 (EGFR) and integrin-β1 in astrocytoma frozen sections predict clinical outcome and correlate with Akt-mediated in vitro radioresistance. *Neuro-oncology*, 15:1027-1040, 2013.

Pietras et al., Remission of human breast cancer xenografts on therapy with humanized monoclonal antibody to HER-2 receptor and DNA-reactive drugs, *Oncogene*, 17:2235-2249, 1998.

Qin et al., Interferon-beta gene therapy inhibits tumor formation and causes regression of established tumors in immune-deficient mice. *Proc. Natl. Acad. Sci. USA.*, 95:14411-14416, 1998.

Ravindranath and Morton, Role of Gangliosides in Active Immunotherapy with Melanoma Vaccine, *Intern. Rev. Immunol.*, 7:303-329, 1991.

Reginato et al., Integrins and EGFR coordinately regulate the pro-apoptotic protein Bim to prevent anoikis. *Nature Cell Biology*, 5:733-740, 2003.

Remington's Pharmaceutical Sciences, 18th Ed. Mack Printing Company, pp. 1289-1329, 1990.

Rosenberg et al., Use of tumor-infiltrating lymphocytes and IL-2 in the immunotherapy of patients with metastatic melanoma: a preliminary report, *N. Engl. J. Med.*, 319: 1676-1680, 1988.

Rosenberg et al., Experience with the use of high-dose interleukin-2 in the treatment of 652 cancer patients, *Ann. Surg.*, 210:474-548, 1989.

Sakamoto et al., Talin1 promotes tumor invasion and metastasis via focal adhesion signaling and anoikis resistance. *Cancer Research*, 70:1885-1895, 2010.

Sakamoto et al., Anoikis disruption of focal adhesion-Akt signaling impairs renal cell carcinoma. *European Urology*, 59:734-744, 2011.

Schiller et al., β1- and αv-class integrins cooperate to regulate myosin II during rigidity sensing of fibronectin-based microenvironments. *Nature Cell Biology*, 15:625-636, 2013.

Schnell et al., Effect of blood collection technique in mice on clinical pathology parameters. *Human Gene Therapy*, 13:155-161, 2002.

Serra et al., A KRAS-directed transcriptional silencing pathway that mediates the CpG island methylator phenotype. *Elife*, 3:e02313, 2014.

Shibue and Weinberg, Integrin β1-focal adhesion kinase signaling directs the proliferation of metastatic cancer cells disseminated in the lungs. *Proc. Natl. Acad. Sci. USA*, 106:10290-10295, 2009.

Siegel et al., Cancer statistics, 2014. *CA: A Cancer Journal for Clinicians*, 2014.

Simpson et al., Anoikis resistance and tumor metastasis. *Cancer Letters*, 272:177-185, 2008.

Song et al., RNA interference targeting Fas protects mice from fulminant hepatitis, *Nature Med.*, 9:347-351, 2003.

Sood et al., Molecular determinants of ovarian cancer plasticity. *The American Journal of Pathology*, 158:1279-1288, 2001.

Sood et al., Adrenergic modulation of focal adhesion kinase protects human ovarian cancer cells from anoikis. *The Journal of Clinical Investigation*, 120:1515-1523, 2010.

Spannuth et al., Functional significance of VEGFR-2 on ovarian cancer cells. *International Journal of Cancer*, 124:1045-1053, 2009.

Suyama et al., A signaling pathway leading to metastasis is controlled by N-cadherin and the FGF receptor. *Cancer Cell*, 2:301-314, 2002.

Tadepally et al., Evolution of C2H2-zinc finger genes and subfamilies in mammals: species-specific duplication and loss of clusters, genes and effector domains. *BMC Evolutionary Biology*, 8:176, 2008.

Thaker et al., EphA2 expression is associated with aggressive features in ovarian carcinoma. *Clinical Cancer Research*, 10:5145-5150, 2004.

Tibes et al., Reverse phase protein array: validation of a novel proteomic technology and utility for analysis of primary leukemia specimens and hematopoietic stem cells. *Molecular Cancer Therapeutics*, 5:2512-2521, 2006.

Vachon, Integrin signaling, cell survival, and anoikis: distinctions, differences, and differentiation. *Journal of Signal Transduction,* 2011:738137, 2011.

Varum et al., High-field NMR-spectroscopy of partially N-deacetylated chitins (chitosans). 1. Determination of the degree of N-acetylation and the distribution of N-acetyl groups in partially N-deacetylated chitins (chitosans) by high-field NMR-spectroscopy, *Carbohydr. Res.,* 211:17-23, 1991.

Vaughan et al., Rethinking ovarian cancer: recommendations for improving outcomes. *Nature Reviews Cancer,* 11:719-725, 2011.

Weis and Cheresh, Tumor angiogenesis: molecular pathways and therapeutic targets. *Nature Medicine,* 17:1359-1370, 2011.

Zhang et al., Integrin activation by R-ras. *Cell,* 85:61-69, 1996.

---

What is claimed is:

1. A nanoparticle for delivery of a therapeutic agent, comprising:
   (a) an inner core consisting of a chitosan, a polyphosphate anion, and a therapeutic agent; and
   (b) an outer coat comprising polylactic acid,
   wherein the therapeutic agent is an RNA,
   wherein the RNA inhibits the expression of a gene that encodes zinc finger protein 304 (ZNF304) and comprises the sequence of SEQ ID NO: 12 or SEQ ID NO: 14,
   wherein the weight ratio of the chitosan to the polyphosphate anion is about 3,
   wherein the polyphosphate anion is a compound of the formula:

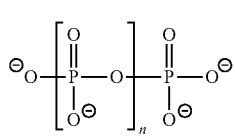

wherein n is an integer ranging from 2-10.

2. The nanoparticle of claim 1, further comprising at least one additional therapeutic agent or diagnostic agent in the outer coat.

3. The nanoparticle of claim 1, wherein the polyphosphate anion is tripolyphosphate.

4. A pharmaceutical composition comprising the nanoparticle of claim 1 and a pharmaceutically acceptable carrier.

* * * * *

SEQUENCE LISTING

<160> NUMBER OF SEQ ID NOS: 41

<210> SEQ ID NO 1
<211> LENGTH: 659
<212> TYPE: PRT
<213> ORGANISM: Homo sapiens

<400> SEQUENCE: 1

```
Met Ala Ala Val Leu Met Asp Arg Val Gln Ser Cys Val Thr Phe
1               5                   10                  15

Glu Asp Val Phe Val Tyr Phe Ser Arg Glu Glu Trp Glu Leu Leu Glu
                20                  25                  30

Glu Ala Gln Arg Phe Leu Tyr Arg Asp Val Met Leu Glu Asn Phe Ala
            35                  40                  45

Leu Val Ala Thr Leu Gly Phe Trp Cys Glu Ala Glu His Glu Ala Pro
    50                  55                  60

Ser Glu Gln Ser Val Ser Val Glu Gly Val Ser Gln Val Arg Thr Ala
65                  70                  75                  80

Glu Ser Gly Leu Phe Gln Lys Ala His Pro Cys Glu Met Cys Asp Pro
                85                  90                  95

Leu Leu Lys Asp Ile Leu His Leu Ala Glu His Gln Gly Ser His Leu
                100                 105                 110

Thr Gln Lys Leu Cys Thr Arg Gly Leu Cys Arg Arg Arg Phe Ser Phe
            115                 120                 125

Ser Ala Asn Phe Tyr Gln His Gln Lys Gln His Asn Gly Glu Asn Cys
    130                 135                 140

Phe Arg Gly Asp Asp Gly Gly Ala Ser Phe Val Lys Ser Cys Thr Val
145                 150                 155                 160

His Met Leu Gly Arg Ser Phe Thr Cys Arg Glu Glu Gly Met Asp Leu
                165                 170                 175

Pro Asp Ser Ser Gly Leu Phe Gln His Gln Thr Thr Tyr Asn Arg Val
            180                 185                 190

Ser Pro Cys Arg Arg Thr Glu Cys Met Glu Ser Phe Pro His Ser Ser
    195                 200                 205

Ser Leu Arg Gln His Gln Gly Asp Tyr Asp Gly Gln Met Leu Phe Ser
    210                 215                 220

Cys Gly Asp Glu Gly Lys Ala Phe Leu Asp Thr Phe Thr Leu Leu Asp
225                 230                 235                 240

Ser Gln Met Thr His Ala Glu Val Arg Pro Phe Arg Cys Leu Pro Cys
                245                 250                 255

Gly Asn Val Phe Lys Glu Lys Ser Ala Leu Ile Asn His Arg Lys Ile
                260                 265                 270

His Ser Gly Glu Ile Ser His Val Cys Lys Glu Cys Gly Lys Ala Phe
            275                 280                 285

Ile His Leu His His Leu Lys Met His Gln Lys Phe His Thr Gly Lys
    290                 295                 300
```

```
Arg His Tyr Thr Cys Ser Glu Cys Gly Lys Ala Phe Ser Arg Lys Asp
305                 310                 315                 320

Thr Leu Val Gln His Gln Arg Val His Thr Gly Glu Arg Ser Tyr Asp
            325                 330                 335

Cys Ser Glu Cys Gly Lys Ala Tyr Ser Arg Ser Ser His Leu Val Gln
            340                 345                 350

His Gln Arg Ile His Thr Gly Glu Arg Pro Tyr Lys Cys Asn Lys Cys
            355                 360                 365

Gly Lys Ala Phe Ser Arg Lys Asp Thr Leu Val Gln His Gln Arg Phe
            370                 375                 380

His Thr Gly Glu Arg Pro Tyr Glu Cys Ser Glu Cys Gly Lys Phe Phe
385                 390                 395                 400

Ser Gln Ser Ser His Leu Ile Glu His Trp Arg Ile His Thr Gly Ala
            405                 410                 415

Arg Pro Tyr Glu Cys Ile Glu Cys Gly Lys Phe Phe Ser His Asn Ser
            420                 425                 430

Ser Leu Ile Lys His Arg Arg Val His Thr Gly Ala Arg Ser Tyr Val
            435                 440                 445

Cys Ser Lys Cys Gly Lys Ala Phe Gly Cys Lys Asp Thr Leu Val Gln
450                 455                 460

His Gln Ile Ile His Thr Gly Ala Arg Pro Tyr Glu Cys Ser Glu Cys
465                 470                 475                 480

Gly Lys Ala Phe Ser Arg Lys Asp Thr Leu Val Gln His Gln Lys Ile
            485                 490                 495

His Thr Gly Glu Arg Pro Tyr Glu Cys Gly Glu Cys Gly Lys Phe Phe
            500                 505                 510

Ser His Ser Ser Asn Leu Ile Val His Gln Arg Ile His Thr Gly Ala
515                 520                 525

Lys Pro Tyr Glu Cys Asn Glu Cys Gly Lys Cys Phe Ser His Asn Ser
530                 535                 540

Ser Leu Ile Leu His Gln Arg Val His Thr Gly Ala Arg Pro Tyr Val
545                 550                 555                 560

Cys Ser Glu Cys Gly Lys Ala Tyr Ile Ser Ser Ser His Leu Val Gln
            565                 570                 575

His Lys Lys Val His Thr Gly Ala Arg Pro Tyr Glu Cys Ser Glu Cys
            580                 585                 590

Gly Lys Phe Phe Ser Arg Asn Ser Gly Leu Ile Leu His Gln Arg Val
            595                 600                 605

His Thr Gly Glu Lys Pro Tyr Val Cys Ser Glu Cys Gly Lys Ala Tyr
610                 615                 620

Ser Arg Ser Ser His Leu Val Arg His Gln Lys Ala His Thr Gly Glu
625                 630                 635                 640

Arg Ala His Glu Cys Asn Ser Phe Gly Gly Pro Leu Ala Ala Ser Leu
                    645                 650                 655

Lys Leu Val
```

<210> SEQ ID NO 2
<211> LENGTH: 50
<212> TYPE: DNA
<213> ORGANISM: Homo sapiens

<400> SEQUENCE: 2
agttctcctg cctcagcctc cggagtagct gggactacag gcacccacga            50

<210> SEQ ID NO 3
<211> LENGTH: 50
<212> TYPE: DNA
<213> ORGANISM: Homo sapiens

<400> SEQUENCE: 3
agaccagtgt agacaactgt ttctaggtct ttgaccgtga agaggagaca             50

<210> SEQ ID NO 4
<211> LENGTH: 50
<212> TYPE: DNA
<213> ORGANISM: Homo sapiens

<400> SEQUENCE: 4
tcgcctgctt ccgggtttgg agctcttccg gaggcacaag ggtttcagaa             50

<210> SEQ ID NO 5
<211> LENGTH: 50
<212> TYPE: DNA
<213> ORGANISM: Homo sapiens

<400> SEQUENCE: 5
tggcttgctt ccctcaggcc acttctaact gtggtctcct ctccgccccc             50

<210> SEQ ID NO 6
<211> LENGTH: 50
<212> TYPE: DNA
<213> ORGANISM: Homo sapiens

<400> SEQUENCE: 6
cttgtttcgc ctgcttccgg gtttggagct cttccggagg cacaagggtt             50

<210> SEQ ID NO 7
<211> LENGTH: 50
<212> TYPE: DNA
<213> ORGANISM: Homo sapiens

<400> SEQUENCE: 7
tcaggtgatc tgcctgcctc agcctcccaa agtgctgaga ttccaggcgt             50

<210> SEQ ID NO 8
<211> LENGTH: 50
<212> TYPE: DNA
<213> ORGANISM: Homo sapiens

<400> SEQUENCE: 8
agtctcgctc tttcgccagg ctagagtaca gtggcgcgat cttggctcac             50

<210> SEQ ID NO 9
<211> LENGTH: 50
<212> TYPE: DNA
<213> ORGANISM: Homo sapiens

<400> SEQUENCE: 9
gtcgcaggat cgttgacatc tgtcattaaa ctgtttccag ctgctggcct             50

<210> SEQ ID NO 10
<211> LENGTH: 50
<212> TYPE: DNA
<213> ORGANISM: Homo sapiens

<400> SEQUENCE: 10
gaggctccct ggccctctgc ctctcctttc ctgtccgggt ctctgtggct             50

<210> SEQ ID NO 11
<211> LENGTH: 50
<212> TYPE: DNA
<213> ORGANISM: Homo sapiens

<400> SEQUENCE: 11
atttaagtat ttccttaggg taaattccca gtagctggat tattagaggg    50

<210> SEQ ID NO 12
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 12
gaucacaccu uacacagaa    19

<210> SEQ ID NO 13
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 13
cuuauugagc acuggagaa    19

<210> SEQ ID NO 14
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 14
gcaacauaau ggagagaau    19

<210> SEQ ID NO 15
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 15
uucuccgaac gugucacguu u    21

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 16
gcacagagat tcctgtaccg t    21

<210> SEQ ID NO 17
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 17
tttcaagagt gggtcacaca tc                                            22

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 18
gtgtgaccca ctcttgaaag ac                                            22

<210> SEQ ID NO 19
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 19
ccctctgaag caattctctc cat                                           23

<210> SEQ ID NO 20
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 20
tggaggggcc tcatttgtg                                                19

<210> SEQ ID NO 21
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 21
ctccctgcac gtaaaggatc t                                             21

<210> SEQ ID NO 22
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 22
cctacttctg cacgatgtga tg                                            22

<210> SEQ ID NO 23
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 23
cctttgctac ggttggttac att                                           23

<210> SEQ ID NO 24
<211> LENGTH: 21
<212> TYPE: DNA

-continued

<213> ORGANISM: Artificial Sequence
<220> FEATURE:
<223> OTHER INFORMATION: Synthetic polynucleotide

<400> SEQUENCE: 24
gtaaccaacc gtagcaaagg a                                              21

<210> SEQ ID NO 25
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 25
tcccctgatc ttaatcgcaa aac                                            23

<210> SEQ ID NO 26
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 26
caagagagct gaagactatc cca                                            23

<210> SEQ ID NO 27
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 27
tgaagtccga agtaatcctc ct                                             22

<210> SEQ ID NO 28
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 28
gaacaccagg gatcacacag aaactgtgca cacg                                34

<210> SEQ ID NO 29
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 29
cgtgtgcaca gtttctgtgt gatccctggt gttc                                34

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
gggttgagga gagggaagta                                                20

<210> SEQ ID NO 31
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 31
tgcctttcag ttgctgtcct aa    22

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
aaggccagca gcattgaaag    20

<210> SEQ ID NO 33
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 33
agaacacaga agagctacag gac    23

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
tctgtttctt gccagtgccc    20

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
ccttctgaaa cccttgtgcc    20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
tttgccttga gaaagtcacg    20

<210> SEQ ID NO 37
<211> LENGTH: 21
<212> TYPE: DNA
<213> ORGANISM: Artificial Sequence
<220> FEATURE:

```
<223> OTHER INFORMATION: Synthetic polynucleotide

<400> SEQUENCE: 37
tcctgtaatc ccagcttctc a                                              21

<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38
tgtgtgtgta tatgtgtgtc acctt                                          25

<210> SEQ ID NO 39
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 39
tgcgagaaac caactggtag                                                20

<210> SEQ ID NO 40
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40
tcccaggttc aagcagttct c                                              21

<210> SEQ ID NO 41
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 41
gctcacgcct ggaatctca                                                 19
```